(12) United States Patent
Grossman

(10) Patent No.: US 6,923,320 B2
(45) Date of Patent: Aug. 2, 2005

(54) BANDAGE PACKAGE AND DISPENSER

(76) Inventor: Victor A. Grossman, 91 Rupert Ave., Staten Island, NY (US) 10314

( * ) Notice: Subject to any disclaimer, the term of this patent is extended or adjusted under 35 U.S.C. 154(b) by 256 days.

(21) Appl. No.: 10/190,195

(22) Filed: Jul. 6, 2002

(65) Prior Publication Data

US 2004/0004014 A1 Jan. 8, 2004

(51) Int. Cl.$^7$ ................................................ A61F 13/00
(52) U.S. Cl. .......................... 206/440; 602/57; 206/441
(58) Field of Search ................................. 206/440, 441, 206/447, 469; 602/41, 42, 43, 57, 900, 904

(56) References Cited

U.S. PATENT DOCUMENTS

| | | |
|---|---|---|
| 3,835,992 A | 9/1974 | Adams ........................ 206/390 |
| 3,874,581 A | 4/1975 | Fox et al. ................... 206/268 |
| 4,182,449 A | 1/1980 | Lozlow ....................... 206/441 |
| 4,310,509 A | 1/1982 | Berglund et al. ........... 424/448 |
| 4,323,557 A | 4/1982 | Rosso et al. ................ 424/448 |
| 4,418,822 A | 12/1983 | Dotta ........................ 206/441 |

(Continued)

OTHER PUBLICATIONS

3M Tegaderm and Tegaderm HP Transparent Dressings, 3M Product Catalog, 2000.
D. Satas, Handbook of Pressure–Sensitive Adhesive Technology, Van Nostrand Reinhold, pp. 585–642, 1989.
3M Foam Tapes, Transdermal Drug Delivery Components, 3M Product Catalog, 1999.
Industrial Laser Processes–An Introduction, The Association For Manufacturing Technology.

*Primary Examiner*—David T. Fidei
(74) *Attorney, Agent, or Firm*—Zaretsky & Associates PC; Howard Zaretsky

(57) ABSTRACT

An element dispensing package suitable for dispensing adhesive strips or bandages. Each element is contained within an envelope formed by opposed upper and lower sheets. The lower sheet has a release liner secured thereto to protect the element while it is within the dispenser. The element is releasably secured to a pull cover and is separated from the lower sheet and release liner when the envelope is opened. The pull cover has one or more gripping means to facilitate dispensing of the element contained within the package. Additionally, the lower sheet and upper sheet have optional gripping means to facilitate dispensing of the element contained within the package.

10 Claims, 37 Drawing Sheets

U.S. PATENT DOCUMENTS

| | | | |
|---|---|---|---|
| 4,728,323 A | 3/1988 | Matson | 604/304 |
| 4,781,293 A | 11/1988 | Johns | 206/441 |
| 4,851,076 A | 7/1989 | Manusch | 156/577 |
| 4,852,734 A | 8/1989 | Allen et al. | 206/273 |
| 4,913,138 A | 4/1990 | Yoshida et al. | 128/155 |
| 4,993,586 A | 2/1991 | Taulbee et al. | 221/25 |
| 5,080,227 A | 1/1992 | Focke | 206/273 |
| 5,133,477 A | 7/1992 | Etheredge et al. | 221/25 |
| 5,160,315 A | 11/1992 | Heinecke et al. | 602/57 |
| 5,275,284 A | 1/1994 | Onotsky | 206/441 |
| 5,333,753 A | 8/1994 | Etheredge | 221/33 |
| 5,397,297 A | 3/1995 | Hunter | 602/54 |
| 5,435,459 A | 7/1995 | Huck et al. | 221/70 |
| 5,499,740 A | 3/1996 | Huck et al. | 221/70 |
| 5,511,689 A | 4/1996 | Frank | 221/73 |
| 5,685,833 A | 11/1997 | Turngren | 602/58 |
| 5,738,642 A | 4/1998 | Heinecke et al. | 602/58 |
| 5,782,786 A | 7/1998 | Tomaiuolo | 602/41 |
| 5,792,092 A | 8/1998 | Turngren | 602/58 |
| 5,891,078 A | 4/1999 | Turngren et al. | 602/58 |
| 5,902,260 A | 5/1999 | Gilman et al. | 602/57 |
| 5,947,998 A | 9/1999 | Cartmell et al. | 606/213 |
| 5,976,117 A | 11/1999 | Dunshee et al. | 604/307 |
| 6,010,002 A | 1/2000 | Petterson | 206/441 |
| 6,018,092 A | 1/2000 | Dunshee | 602/54 |
| 6,050,413 A | 4/2000 | Benedetti | 206/440 |
| 6,053,318 A | 4/2000 | Petterson | 206/440 |
| 6,079,190 A | 6/2000 | Simpson | 53/492 |
| 6,124,522 A | 9/2000 | Schroeder | 602/57 |
| 6,140,549 A | 10/2000 | Pompei | 602/57 |
| 6,169,224 B1 | 1/2001 | Heinecke et al. | 602/58 |
| 6,225,522 B1 | 5/2001 | Schroeder | 602/57 |
| 6,503,855 B1 | 1/2003 | Menzies et al. | 442/328 |
| 6,700,033 B1 * | 3/2004 | Marcussen et al. | 602/57 |
| 6,719,137 B2 * | 4/2004 | Dotta | 206/441 |

* cited by examiner

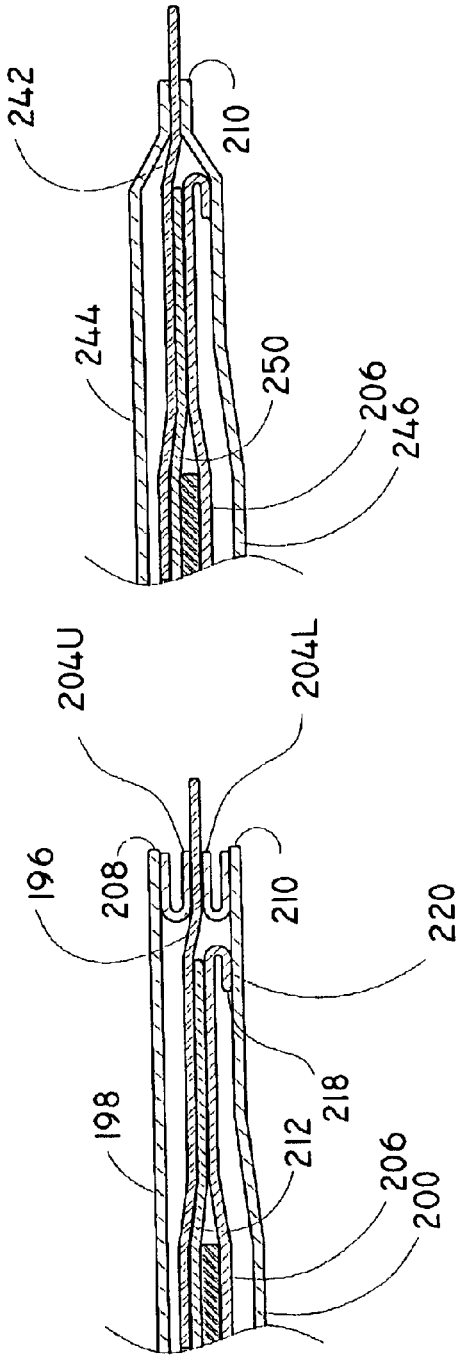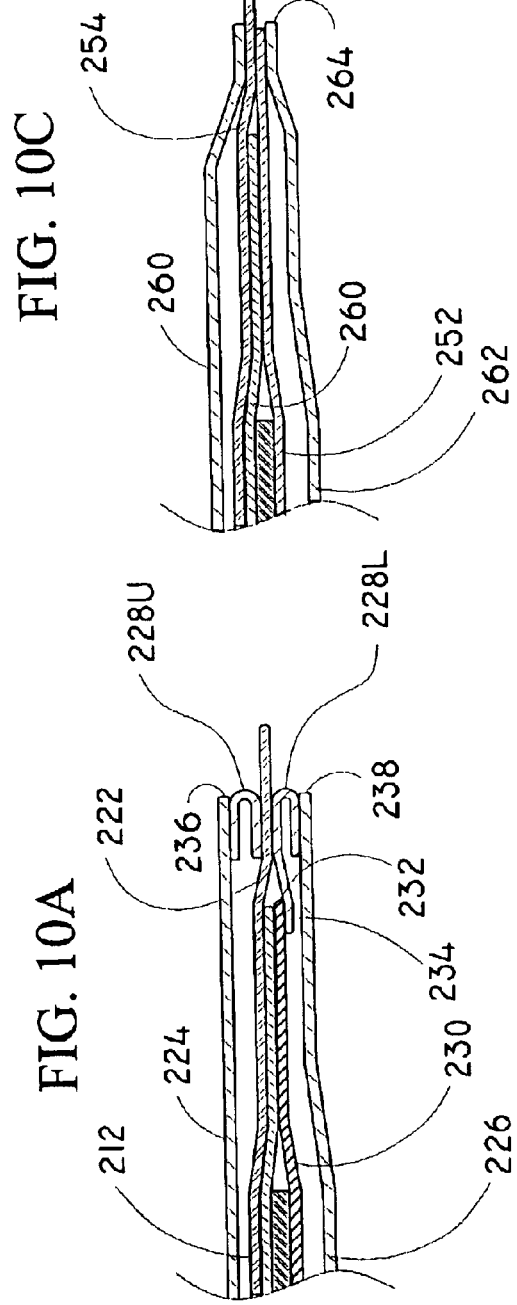
FIG. 10A  FIG. 10C
FIG. 10B  FIG. 10D

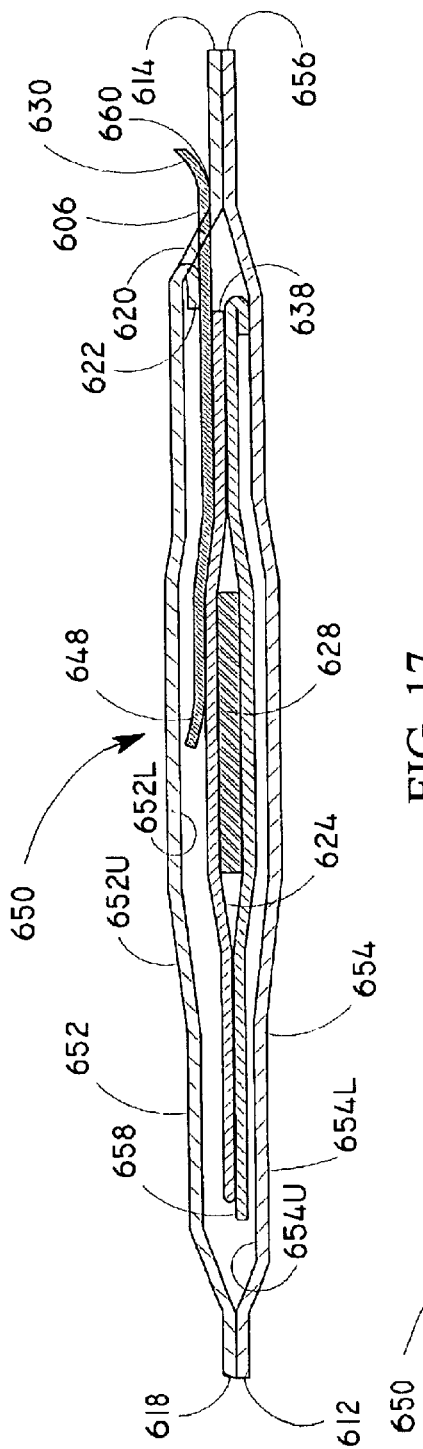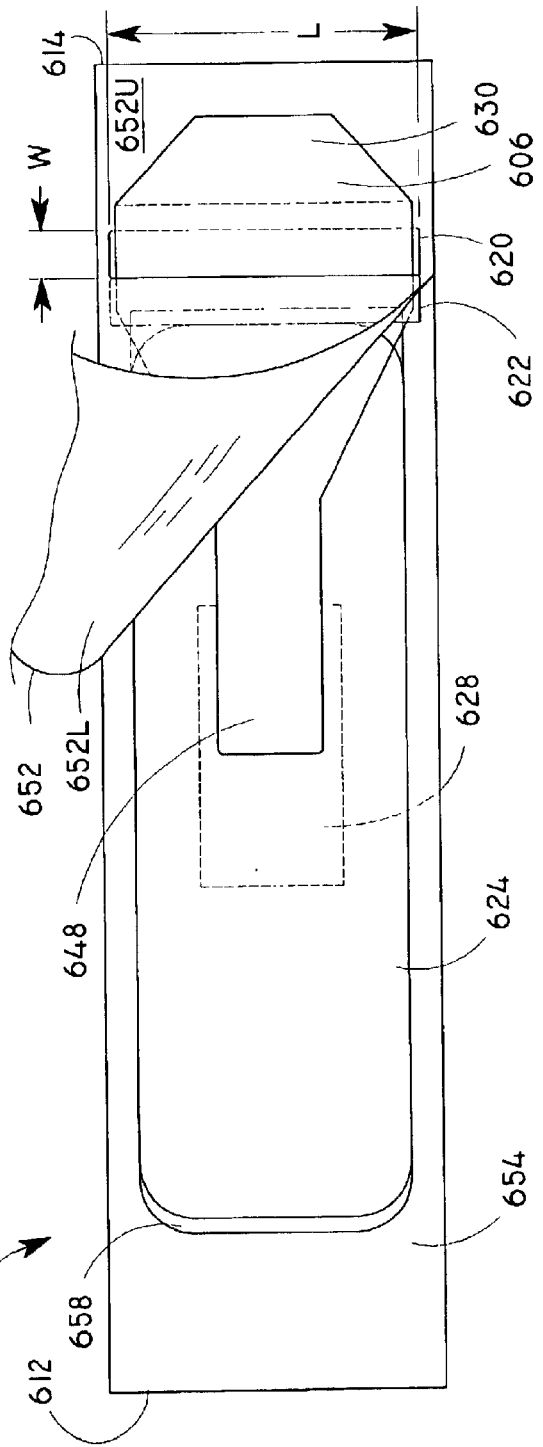
FIG. 17
FIG. 18

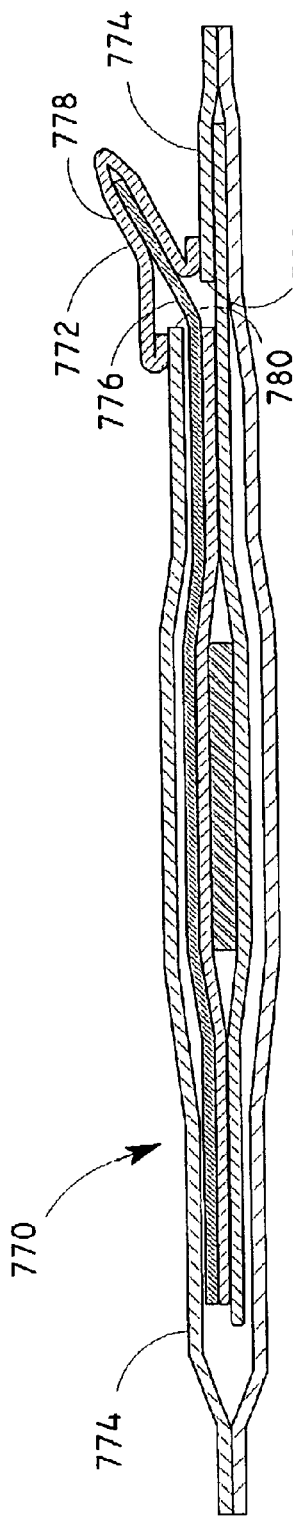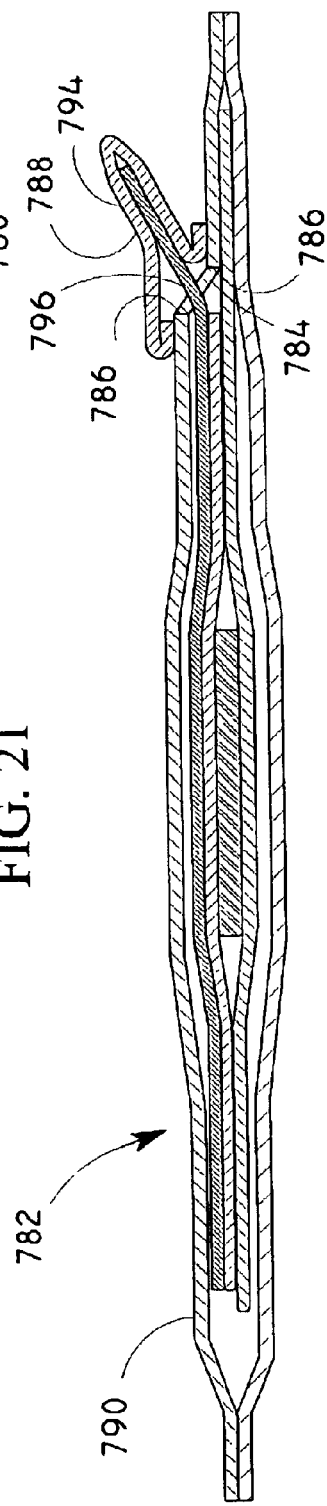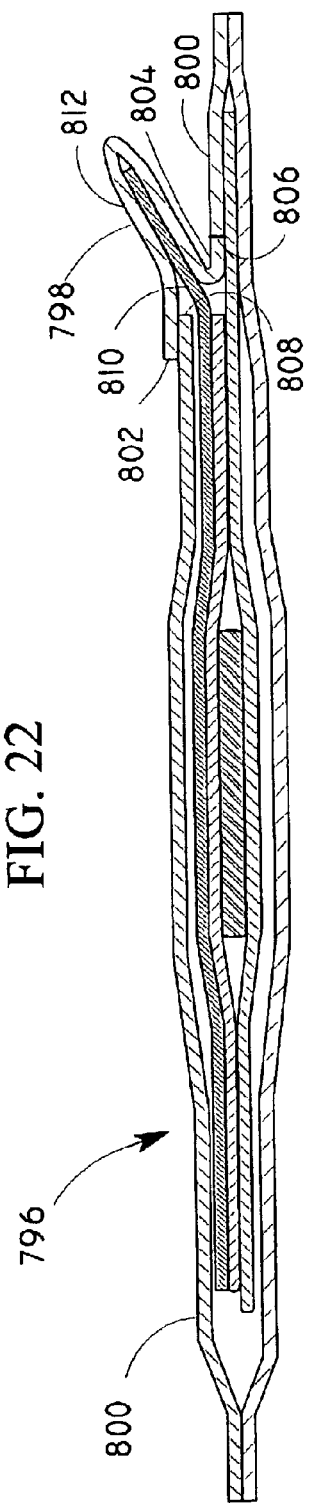

BANDAGE PACKAGE AND DISPENSER

FIELD OF THE INVENTION

The present invention relates generally to packaging and dispensing systems for elements such as bandages, strips, and the like, and more particularly to a single-step dispensing system for the elements therein.

BACKGROUND OF THE INVENTION

Packaging and dispensing systems for commonly-known adhesive bandages are known in the art and described below. Adhesive bandages, commonly called finger bandages, strip bandages, and first-aid bandages, are well known in the prior art. Commercially available adhesive bandages such as the Band-Aid™ brand bandages are for the most part individually packaged. The most widely used packaging means comprises outer wrappers which must be stripped apart to remove the bandage. The bandage typically consists of a backing on which an adhesive layer is applied to one side, and on which a sterile pad suitable for covering wounds is centrally placed. Two removable liners are placed upon the adhesive-coated side of the backing (or adhesive-backed flexible strip) covering both the pad and the adhesive layer.

Typical prior art adhesive bandages and wrappers require one to open an envelope or package containing the bandage, remove the bandage, peel off the removable liners to expose the adhesive layer and pad and then apply the bandage to the body. Such packaging, however, has certain disadvantages, chief of which are: (a) the possibility of touching the sterile pad before application, which may result in loss of sterility; (b) awkwardness and difficulty in applying the bandage to the body, especially with one hand; (c) having the adhesive surface stick to itself while in the process of applying the bandage to the body, thus requiring either the removal of the bandage and an additional application attempt or discarding the bandage entirely and starting the entire process over with a new bandage; and (d) having to dispose of individual wrapping components, which typically consist of the two removable liners and one or two pieces of outer wrapping.

These disadvantages are exacerbated by the conditions under which bandages are often applied. For example, opening of the package is often done under urgent conditions, which increases the likelihood that the bandage will accidentally fall out of the outer wrapper, resulting in loss of sterility of the bandage.

While some prior designs have simplified the process of application of the bandage, they have several disadvantages. One such prior art approach described in U.S. Pat. No. 4,182,449, to Kozlow, entitled "Adhesive bandage and package" discloses a bandage wherein the user is required to place his fingers near the sterile pad to remove the lining, thus increasing the likelihood of inadvertently touching and contaminating the sterile pad.

There have been other attempts to improve the bandage dispensing and application process, such as by folding the bandage over itself and providing for an automatic removal of the liner, as in U.S. Pat. No. 5,333,753 to Etheredge, entitled "Finger bandage package and dispenser." While this design does provide for removal of the bandage and liner, it requires skill in application, as the opened package is cumbersome and typically requires the use of both hands during application of the bandage. Additionally, as the package is folded over itself, it is difficult for the user to determine the size of the bandage contained therein before the package is opened and the bandage unfolded.

Various adhesive bandage dispensing package systems have been described that aid the user in removing the bandage from the package or device with a single hand. One such system is described in U.S. Pat. No. 5,133,477, to Etheredge, et al., entitled "Package or adhesive dressing," which discloses an adhesive bandage dispensing package wherein the adhesive side of the bandage is placed against a continuous carrier strip. One segment (i.e. the trailing edge of the adhesive-coated side of the bandage) is in direct contact with the release-coated continuous carrier strip, while the opposite segment (i.e., the leading adhesive segment) is covered by a release sheet which facilitates removal of the bandage from the continuous carrier strip, but is not otherwise secured to it.

Disadvantages of this design include bulkiness, the possibility of jamming caused by the bandages becoming stuck within the outer containing package as the bandages pass through the slit, and contamination of the bandage and pad caused by the user's touching the pad during removal of the release liner. Additionally, since the design does not enclose each individual bandage within a sealed envelope, the likelihood that the bandage will become contaminated before use is increased. Furthermore, the design does not allow for single bandages to be temporarily stored for application at a later time.

U.S. Pat. No. 4,993,586, to Taulbee, et al., entitled "Adhesive Bandage Dispensing Device and Associated Method," discloses an adhesive bandage dispensing system in which an adhesive bandage is placed between an upper and lower continuous strip. The adhesive side of the bandage is mounted facing downward on the continuous strip and has a releasable liner attached to one segment of the adhesive-coated side of the bandage, which facilitates removal of the bandage from the continuous strip. Additionally, the dispensing system includes a slicer and other components which increase the cost and size of the unit and require one to become familiar with the operation of the system before use. Other disadvantages include the likely contamination of the bandage and pad during the application process, jamming of the unit, and increased environmental waste when the unit is disposed of.

U.S. Pat. No. 3,835,992, to Adams, entitled "Bandage Dispensing Package," discloses a bandage dispensing system using a continuous carrier strip that is rolled or folded upon itself. Bandages are attached to the continuous carrier strip by placing the adhesive surface of the bandages upon the continuous carrier strip. This design requires a carrier strip that is made from a material having the desired release characteristics and that is able to form a side seal in order to form a secure packaging element for a multitude of sterile bandages. Therefore, this design suffers from increased cost, non-standardized operation which requires the user to become familiar with the operation of the system, increased size caused by forming the continuous carrier strip into a roll, and increased likelihood of contamination if the continuous carrier strip roll is dropped, as well as an increased likelihood of contamination during application.

U.S. Pat. No. 5,891,078, to Turngren, et al., entitled "Sterile Adhesive Bandage and Associated Methods," discloses a sterile system for delivery of an adhesive strip or bandage using a single hand. In general, the patent discloses a flexible strip, at least one pull tab, and an optional wound pad sandwiched between a carrier member and a release backing. The invention may also have an optional blocking member. The adhesive strip is removed from the release backing and remains attached to the pull-tab and full-length carrier strip until the last step of the application process.

Disadvantages of this system include difficulty of application and high manufacturing costs. Moreover, as the full-length carrier member may confuse users during application as to which side must be pulled first, it is possible that the user will inadvertently destroy the bandage before he has completed the process of applying it. Furthermore, the full carrier member is larger than the adhesive strip and therefore may complicate handling and positioning of the adhesive strip upon the desired object. In addition, some form of indicia may be needed to help the user identify the proper sequence of pulling on the tabs. Further, one end of the full-length carrier sheet may become bonded to the adhesive on the opposite end of the adhesive strip or bandage, which may result in the destruction of the adhesive strip or bandage before application is complete. Furthermore, as an opaque full-length carrier sheet would conceal the bandage located on its underside, the carrier sheet should be made of transparent materials, which may increase manufacturing costs. Another disadvantage resulting from the separation of the carrier sheet at an edge (such as the leading edge) of the adhesive strip is the difficulty in separating the carrier sheet and/or the optional blocking member from the adhesive strip or bandage member without separating the adhesive strip or bandage from application surfaces, especially low cohesion surfaces.

U.S. Pat. No. 5,511,689, to Frank, entitled "Dispensing Package for Adhesive-Backed Articles," discloses an adhesive-backed article dispensing system suitable for dispensing bandages. This design uses a support layer to remove the article or bandage from the backing layer. The process of applying the article or bandage to the wound, however, is cumbersome because the support layer, which is longer and wider than the bandage itself, remains attached to or dangles from the bandage while the bandage is being applied. Thus, when applying the bandage to the wound, especially in difficult-to-reach areas of the fingers or toes, one or both support strips or sheets obscure the user's view of the wound and get in the way as the user attempts to place the bandage on the wound. Therefore, the user might not precisely place the bandage upon the wound, resulting in further injury when the bandage adhesive (rather than the gauze) is placed on the wound, or contamination of the wound caused by the gauze not being placed directly over the wound. Other disadvantages include the possibility of destruction of the bandage as a result of the user's attempt to remove and reapply a misplaced bandage.

With the advent of so called "thin-film" bandages and wound dressings (also known as "Transparent film dressings") there has developed a need to provide sufficient rigidity to the adhesive strip or bandage using a carrier strip, also referred to as a carrier member, outer frame, blocking member, frame style carrier or other means, until the bandage is successfully applied to the desired object. The carrier strip also prevents the thin-film bandage from stretching excessively when the bandage is removed from the package. One commonly used design to impart rigidity to the thin-film strip or bandage is the partial carrier (or frame-style carrier), which is essentially a ring-like structure removably attached to the strip. This design is used in commercially available bandages such as 3M™ NEXCARE™ WATERPROOF BANDAGES. This design, however, requires that the partial carrier be removed upon application of the bandage. Many users, especially those unfamiliar with the design, tend to pull the carrier strip off the bandage before the bandage is removed from the release liner attached to the lower sheet of the package, thus destroying the bandage. Additionally, users often pull the carrier strip off the bandage at the wrong location, and/or try to pull the carrier strip off in the wrong direction, before or after application of the bandage, both of which result in destruction of the bandage. Additionally, this design has the drawback of requiring the user to pull off the carrier sheet after the bandage is applied to the desired object.

Another known thin-film type bandage is the commercially available 3M™ TEGADERM™ TRANSPARENT DRESSING. This bandage uses a frame style carrier and for the most part is similar to the 3M™ NEXCARE™ bandage. One significant difference is that some TEGADERM™ products have a "window" that must be removed before the bandage is applied to a desired surface. This design has the drawback of requiring the user to pull off the "window" section before the bandage is applied to the desired object.

Another known thin-film bandage is the ADVANCED CURAD™ AQUA-PROTECT™ bandage distributed by FUTURO Inc., which uses a full carrier sheet which superposes the adhesive strip or bandage. In this bandage, the carrier sheet is releasably attached to the adhesive strip or bandage so that it can be removed by pulling on an attached pull tab (also called a blue flap) once the adhesive strip or bandage is applied to the desired object. A disadvantage, however, is that many users, especially those unfamiliar with the operation of the design, remove the full-length carrier sheet before applying the bandage, resulting in the destruction of the bandage or try to remove the carrier sheet by pulling on a corner of the bandage thereby inadvertently pulling the bandage off the desired object. Moreover, many users, while trying to determine how to remove the carrier sheet, attempt to pull some part of the bandage but not knowing what or where to pull, they attempt to grasp the pull tab at the interior edge rather than the exterior edge and not being able to grasp it at that point, they give up and do not remove the carrier sheet and therefore do not benefit from the use of the thin-film materials.

Thus, there is a need for an easy to use one-handed bandage package and dispensing system that is capable of dispensing bandages, adhesive strips, flexible strips, or other elements from a dispenser that avoids the problems and disadvantages of prior art systems.

SUMMARY OF THE INVENTION

The present invention is a bandage packaging and dispensing system particularly suited for dispensing adhesive-backed elements such as bandages and the like. The bandage packages comprise a backing of suitable material on one surface of which a pressure-sensitive adhesive is applied and an optional pad suitable for covering wounds is centrally placed. In one embodiment the adhesive-coated surface of the flexible strip or bandage is placed in contact with and superimposes a release liner. A surface of the release liner is in contact with a lower sheet having an optional gripping means so as to facilitate opening. A multi-part top sheet comprised of at least two sheets (an upper sheet and a pull cover) is in contact with the upper surface of the adhesive strip or bandage. The pull cover is releasably attached to the upper sheet and comprises a gripping means on the exterior end. The interior end of the pull cover has an optional gripping means. The pull cover and upper sheet combination superposes the lower sheet and is releasably attached thereto along the outer perimeter of the package formed by the said combination and the lower sheet.

One or more optional blocking members are placed along the perimeter of the package to equalize the exterior thickness of the package in desired areas. The blocking member or members are placed at selected locations or continuously along the perimeter of the package.

The upper sheet and the lower sheet are fixably attached or releasably attached to each other except at those points where the blocking member intervenes between them, at which points the upper and/or lower sheets may be fixably attached or releasably attached to the blocking member. Moreover, the blocking member may intervene between the pull cover and either the upper sheet or the lower sheet, in which case the pull cover is releasably attached to the blocking member. Optionally, the upper sheet and the lower sheet are formed integrally from the same sheet of material.

The strip or bandage is placed in an envelope within the package formed by the pull cover, upper sheet and lower sheet and is releasably attached to the pull cover.

In alternative embodiments, the package and dispenser is incorporated into a larger assembly by attaching the upper sheet or the lower sheet to additional upper sheets or lower sheets, respectively, along their transverse ends or lateral ends or both so as to form a continuous sheet packaging and dispensing mechanism.

In another embodiment, a plurality of packages is stacked upon each other to form a dispensing pack suitable for dispensing a plurality of elements. Additionally, a box stores a plurality of individual packages or a containing-pack and dispenses elements such as bandages or flexible strips as needed.

The present invention provides a sterile package dispensing mechanism for flexible strips, bandages or the like which can be easily removed from the dispenser with minimal effort and which can be applied with a single hand thus minimizing the possibility of contaminating the adhesive strip or the absorbent pad or diminishing the adhesive properties of the adhesive strip.

An advantage of the present invention is that it simplifies and expedites the bandage application process by eliminating the need to separate a release liner from the bandage or adhesive strip once the package and dispenser are opened. Furthermore, the present invention obviates the need to dispose of removed release liners. Moreover, as only a small segment of the pull cover (and/or the optional carrier sheet) remains attached to the bandage during application to the wound, the pull cover does not obscure the user's view of the wound or get in the way during the application process. This facilitates precise and convenient one-handed application of the bandage to the wound. Furthermore, the attached pull cover operates as a handle and enhances the user's grip on the bandage during application. Thus, use of the present invention significantly increases the likelihood of successful, precise application of the bandage.

Additional advantages of the present invention include the incorporation of features that reduce the complexity and cost of manufacturing; providing a system for dispensing a plurality of adhesive strips wherein the system comprises a minimum number of moving parts. Note that one skilled in the art can easily adapt the packaging and dispensing mechanism of the present invention to package and dispense numerous items such as surgical drapes, nasal strips, non-flexible items such as matches, syringes, microscope slides or slide covers, surgical instruments, thermometers, medical testing devices, etc.

There is thus provided in accordance with the present invention a bandage package apparatus comprising a lower sheet having an upper surface and a lower surface, a release liner attached to the lower sheet, an adhesive strip having an upper surface and a lower surface, the lower surface being releasably attached to the release liner, an upper sheet having an upper surface and a lower surface, the upper sheet being attached to the lower sheet, a pull cover releasably attached to the adhesive strip, the pull cover being shaped and sized such that it covers those areas of the adhesive strip and the lower sheet that are not covered by the upper sheet, the pull cover being releasably attached to the upper sheet and to the lower sheet and a first tab suitable for grasping attached to the pull cover, wherein the act of pulling the first tab causes the separation of the release liner from the adhesive strip and also causes the removal of the adhesive strip from the package.

There is also provided in accordance with the present invention a bandage package apparatus comprising a lower sheet having an upper surface and a lower surface, an upper sheet having an upper surface and a lower surface, the upper sheet substantially superposing and being attached to the lower sheet to form an enclosure, an opening located on the upper sheet such that a majority of the upper sheet lies on one side of the opening, a release liner attached to the upper surface of the lower sheet such that a portion of the release liner is situated within the enclosure, a bandage releasably attached to the release liner, the bandage being located within the enclosure and a pull cover having a first tab, the pull cover being releasably attached to both the bandage and the upper sheet, the pull cover extending through the opening far enough so that the first tab can be readily grasped, the pull cover further including a pull tab, wherein the act of pulling the pull tab causes the separation of the pull cover from the upper sheet, the separation of the release liner from the adhesive strip and the removal of the adhesive strip from the package.

There is further provided in accordance with the present invention a bandage package apparatus comprising a lower sheet having an upper surface, a lower surface and an appendage, a release liner attached to the lower sheet, a bandage having an upper surface and a lower surface, the lower surface being releasably attached to the release liner, an upper sheet having an upper surface, a lower surface and an appendage, the upper sheet being attached to the lower sheet, a pull cover releaseably attached to the appendage of the upper sheet, the appendage of the lower sheet and the bandage, the pull cover adapted to cover at least that area of the bandage and the lower sheet that are not covered by the upper sheet so as to form an envelope for enclosing and retaining the bandage within the package, the pull cover further including a first tab suitable for grasping, a pull tab suitable for grasping, the pull tab being associated with the pull cover and wherein the act of pulling the first tab causes the separation of pull cover from the upper sheet and the lower sheet, and also causes the separation of the release liner from the bandage and the consequent removal of the adhesive strip from the package.

There is also provided in accordance with the present invention a bandage package and dispensing apparatus comprising a roll of bandage packages wherein bandage packages are connected end to end in a continuous manner, a container adapted to store the roll of bandage packages whereby bandage packages can be removed from the container, wherein each bandage package comprises a lower sheet having an upper surface and a lower surface, a release liner attached to the lower sheet, an adhesive strip having an upper surface and a lower surface, the lower surface being releasably attached to the release liner, an upper sheet having an upper surface and lower surface, the upper sheet being attached to the lower sheet, a pull cover releasably attached to the adhesive strip, the pull cover being shaped and sized such that it covers those areas of the adhesive strip and the lower sheet that are not covered by the upper sheet, the pull cover being releasably attached to the upper sheet and to the lower sheet and a first tab suitable for grasping attached to the pull cover, wherein the act of pulling the first tab causes the separation of the release liner from the adhesive strip and also causes the removal of the adhesive strip from the package.

There is further provided in accordance with the present invention a bandage package and dispensing apparatus comprising a stack of bandage packages, a substantially rectangular container openable on one end and adapted to protect and store the stack of bandage packages, wherein each the bandage package comprises a lower sheet having an upper surface and a lower surface, a release liner attached to the lower sheet, an adhesive strip having an upper surface and a lower surface, the lower surface being releasably attached to the release liner, an upper sheet having an upper surface and a lower surface, the upper sheet being attached to the lower sheet, a pull cover releasably attached to the adhesive strip, the pull cover being shaped and sized such that it covers those areas of the adhesive strip and the lower sheet that are not covered by the upper sheet, the pull cover being releasably attached to the upper sheet and to the lower sheet and a first tab suitable for grasping attached to the pull cover, wherein the act of pulling the first tab causes the separation of the release liner from the adhesive strip and also causes the removal of the adhesive strip from the package.

BRIEF DESCRIPTION OF THE DRAWINGS

The invention is herein described, by way of example only, with reference to the accompanying drawings, wherein:

FIG. 10A is a cross-sectional view illustration of a third alternative embodiment of the present invention, which shows the attachment of the release liner to the lower sheet as well as the attachment of the pull cover to both the upper sheet and the lower sheet;

FIG. 10B is a cross-sectional view illustration of a fourth alternative embodiment of the present invention which shows the attachment of the release liner to the attachment tab as well as the attachment of the pull cover to both the upper sheet and the lower sheet;

FIG. 10C is a cross-sectional view illustration of a fifth alternative embodiment of the present invention, which shows the attachment of the release liner to the lower sheet as well as the attachment of the pull cover to both the upper sheet and the lower sheet using an adhesive;

FIG. 10D is a cross-sectional view illustration of a sixth alternative embodiment of the present invention, which shows the attachment of the pull cover to the upper sheet as well as to the release liner using an adhesive;

FIG. 17 is a cross-sectional view illustration of a seventh alternative embodiment of the present invention, showing a pull cover extending through an opening in the upper sheet;

FIG. 18 is a detailed top-view illustration of the adhesive strip or bandage and dispenser package of FIG. 17 with the upper sheet peeled back;

FIG. 21 is a detailed cross sectional view illustration of the adhesive strip or bandage and dispenser package of FIG. 19 having a first alternative embodiment of the pull cover;

FIG. 22 is a detailed cross sectional view illustration of the adhesive strip or bandage and dispenser package of FIG. 19 having a second alternative embodiment of the pull cover;

FIG. 23 is a detailed cross sectional view illustration of the adhesive strip or bandage and dispenser package of FIG. 19 having a third alternative embodiment of the pull cover;

DETAILED DESCRIPTION OF THE INVENTION

The following terms and definitions apply throughout this document.

The term flexible strip is used to denote a strip, spot, patch, eye occlusion, testing strip, wound dressing of various shapes and materials (such as commonly-known foam wound dressings), or like device which flexes easily and which has two surfaces, including an upper surface and a lower surface.

The term adhesive strip denotes a flexible strip upon which an adhesive coating is applied to a surface thereof.

The term bandage denotes a flexible strip with an adhesive coating applied to a surface thereof, upon which an absorbent pad is placed.

In all embodiments of this invention, cohesives may be used rather than adhesives to join or bond surfaces together, except, of course, where practical considerations require otherwise.

Note that throughout the present invention, interchangeability of components is contemplated and the corresponding terms throughout this specification including the claims may therefore be substituted for one another as desired as would be reasonable to one skilled in the art. For example, a bandage may be substituted for a flexible strip, in which case a release means must be included, whereas if a flexible strip is used rather than a bandage or an adhesive strip, the release means may be excluded depending upon implementation.

The term package refers to the combination formed for the most part by an upper sheet, a lower sheet, a pull cover and an optional release means. However, when the pull cover is separated from the other elements, the term "package" refers to the combination formed by the upper sheet, the lower sheet, and the release means.

The term bond denotes bonds, seams and seals unless the context indicates otherwise.

Throughout this invention, when using a blocking member that is placed between and attached to both the upper sheet and the lower sheet it will be assumed that the upper sheet is attached to the lower sheet.

The present invention is applicable to medical dressings and the like and is characterized by a flexible strip interposed between at least one upper sheet and a lower sheet with an attached pull cover included to remove the flexible strip from the package and an attached release liner included far adhesive-strip or bandage applications. It will be appreciated that the flexible strip is completely contained between the upper sheet or sheets, the pull cover and the lower sheet. The package thus formed constitutes a sterile enclosure without the need for additional packaging.

It will be further appreciated by one skilled in the art that the embodiments of the present invention may be constructed using different materials, such as polymers, which include polyurethane, polyolefin, polyester, polyethylene, polyethylene/EVA, polyvinyl, polyvinyl-chloride, plastic, paper, treated paper, cloth, and other materials of suitable construction.

Figure 1:
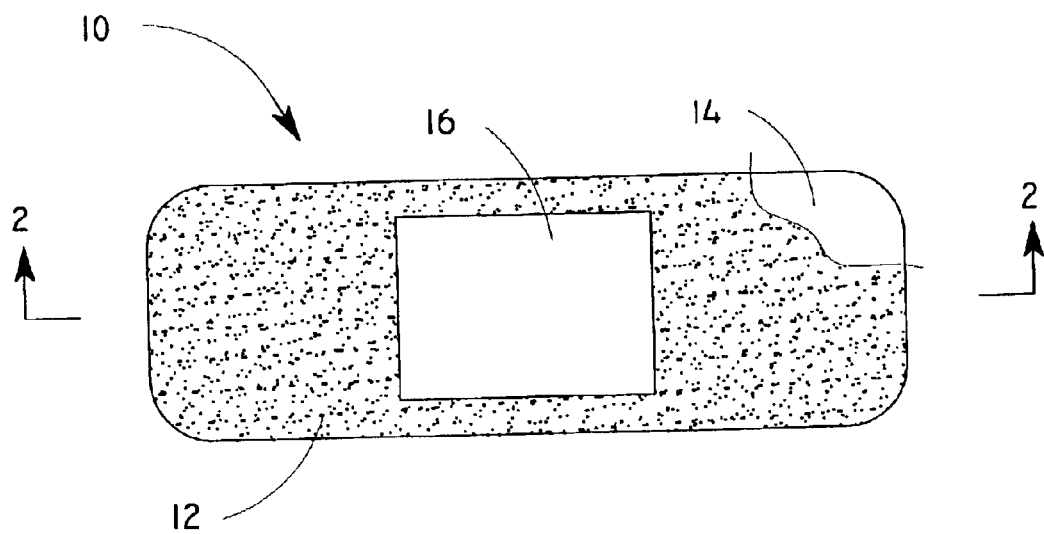
FIG. 1 is a bottom planar view illustration of the flexible strip of the present invention with an adhesive layer and an absorbent pad affixed thereon.

A bottom planar view illustration of the flexible strip of the present invention with an adhesive layer and an absorbent pad affixed thereon is shown in FIG. 1. A flexible strip 10 comprises a pressure-sensitive adhesive surface 12 applied to a lower surface 14 (to produce an adhesive strip) and an absorbent pad 16 suitable for use on wounds, centrally disposed upon the adhesive-coated lower surface, leaving exposed adhesive for securing the flexible strip to a desired object. Although the flexible strip is depicted in a rectangular shape, it will be appreciated that other shapes, such as circular, square, "X," "H," "clover," "star," are also possible with minimal modifications.

Figure 2:
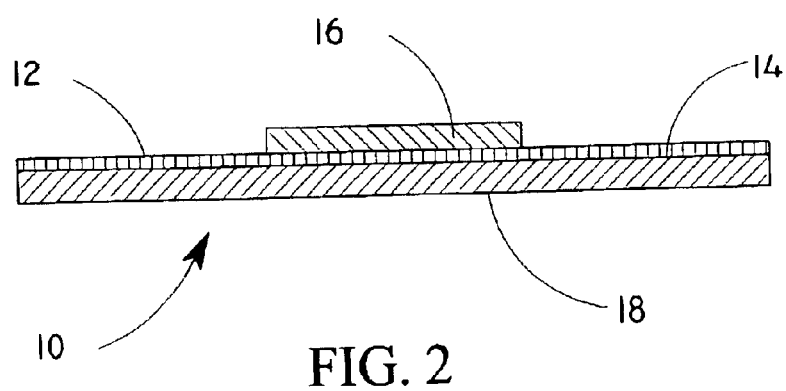
FIG. 2 is a cross section view illustration of the flexible strip shown in FIG. 1 with an adhesive layer and an absorbent pad attached thereto.

A cross section view illustration of the flexible strip of FIG. 1 is shown in FIG. 2. The flexible strip 10 has an upper surface 18 and an opposed lower surface 14. A pressure-sensitive adhesive surface 12 is applied upon the lower surface. An absorbent pad 16, suitable for use on wounds, is centrally disposed upon the adhesive-coated lower surface, leaving exposed adhesive for securing the adhesive strip to a desired object. Note that for illustration purposes the adhesive surface is depicted as separate from the surface upon which it rests. In other figures which include the adhesive surface the adhesive surface is omitted from the drawings for clarity purposes but is assumed to be present.

The flexible strip is constructed from any suitable flexible material rigid enough such that the flexible strip does not fold upon itself during application. Alternatively, if the flexible strip is not constructed from a material of such rigidity, it can be reinforced by using a rigidity-enhancing carrier as described infra.

Figure 3:
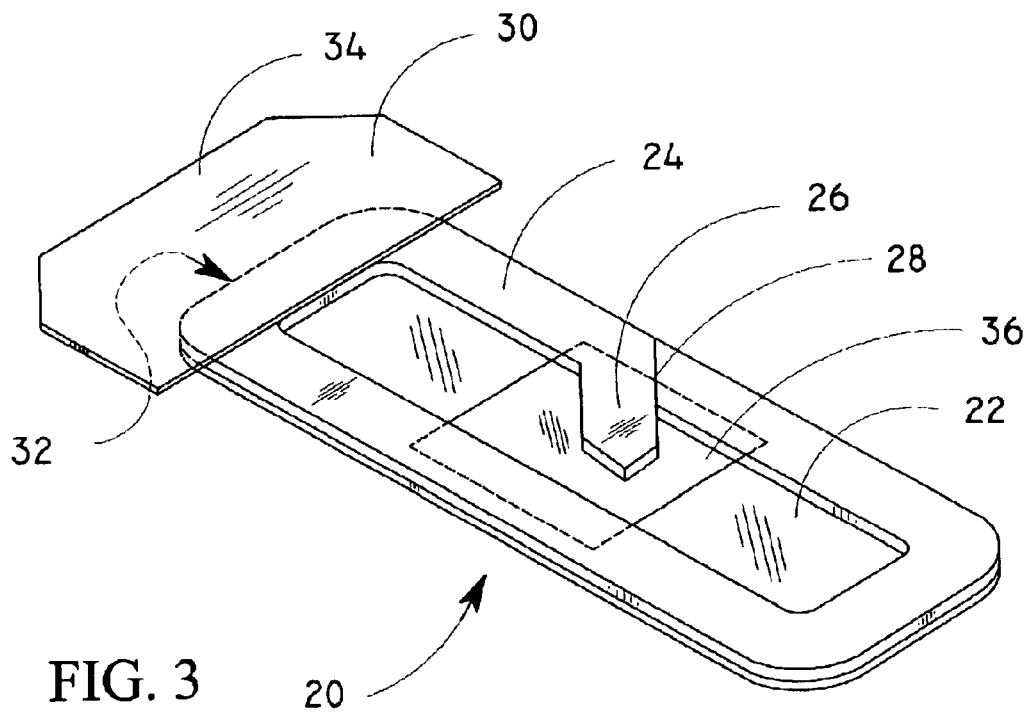
FIG. 3 is a perspective view illustration of an adhesive strip constructed in accordance with the present invention including a partial carrier and a pull cover.

A perspective view illustration of an adhesive strip constructed in accordance with the present invention comprising a partial carrier and a pull cover is shown in FIG. 3. A carrier 24 is releasably laminated upon the upper surface 22 of the adhesive strip 20. The adhesive strip 20 is preferably constructed from thin films (or other types of polymers) of suitable known construction, such as polyurethane or polyethylene, which are commercially available from the 3M Corporation, St. Paul, Minn. The carrier is preferably manufactured from a material rigid enough to prevent curling of the adhesive strip before it is applied to the desired surface and is releasably laminated using a suitable means such as cold bonding.

Suitable means for attaching the carrier to the adhesive strip depend upon the type of materials used to construct the adhesive strip and may comprise pressure bonding, thermal bonding, pressure-sensitive adhesives or combinations of these, or other means which are commonly known in the art. The bond between the carrier and the adhesive strip should be sufficiently strong so that the carrier does not separate from the adhesive strip before the adhesive strip is applied to a desired surface, but should not be so strong that the carrier, when removed from the adhesive strip, damages the adhesive bond between the adhesive strip and the desired surface. Such carriers are well known in the art.

The outer perimeter of the carrier is shaped and sized similarly to or identically to the adhesive strip so that it is substantially or fully congruent with the outer perimeter of the adhesive strip to which it is attached. In alternative embodiments, the carrier is shaped and sized so that the outer perimeter of the carrier may be located either inside or outside the outer perimeter of the adhesive strip. In other alternative embodiments, the carrier may be die cut from the same sheet of material as the adhesive strip and may therefore lie in the same plane as the adhesive strip and may surround the perimeter of the adhesive strip.

The carrier has an opening termed a window in its center section, which enables the user to observe the surface to which it is intended to apply the adhesive strip, thereby allowing for application of the adhesive strip at the precise location desired. Furthermore, the carrier is shaped so that it generally forms a ring-like structure or frame (which may be broken in certain areas) adjacent to the outer perimeter of the adhesive strip which is rigid enough to prevent curling of the adhesive strip during the process of dispensing and applying the adhesive strip. Alternatively, the carrier may be formed to have other shapes, such as described infra.

The carrier may be constructed using any suitable material such as treated paper or kraft paper. Alternatively, the carrier may be made from other suitable materials as are commonly known in the art and which include without limitation, polymers, etc. Examples of suitable materials include, without limitation, (1) 60BKG-157 super calendrated kraft paper with a water based silicon surface or (2) 80BKG-15799AM two sided silicone coated bleached kraft glassine 80 lb/ream basis weight with an easy release on one side and a tighter release on the other side, emulsion tin silicone technology material. Both of these materials are commercially available from DCP-LOHJA, Inc., Willowbrook, Ill. Other types of carriers, such as those which are commonly known in the arts, are also contemplated by the invention.

The user is also directed to U.S. Pat. No. 5,160,315, to Heinecke, et al., entitled "Combined adhesive strip and transparent dressing delivery system," U.S. Pat. Nos. 5,738, 642 and 6,169,224, both issued to Heinecke, et al., and entitled "Carrier delivered dressing and method of manufacture," all of which describe transparent dressings with carrier layers in more detail and are incorporated herein by reference in their entirety.

The carrier has at least one removal means, such as a pull tab 26, to assist the user in removing the carrier from the adhesive strip. Preferably, the pull tab is located within the interior portion of the carrier. Alternatively, however, the pull tab may extend beyond the outer perimeter of the carrier. A slit 28 is located adjacent to the pull tab. The slit is preferably angled in a direction not parallel with the line of separation between the adhesive strip and a release liner, so that it reduces shear stress upon and stretching of the adhesive strip during removal of the adhesive strip from the package and also helps keeps the adhesive strip rigid so that it does not fold upon itself after it is removed from the package. In a preferred embodiment, the placement of the pull tab and the slit causes the separation of the carrier from the adhesive strip to start at the interior portion of the adhesive strip and work around the outer perimeter of the adhesive strip (preferably using peel stress as opposed to shear stress) in a direction which would be less likely to disturb the bond between the adhesive strip and the surface to which it is attached.

The pull cover 30 is constructed from a flexible material and is attached to the carrier 24 adjacent to the leading edge 32 of the adhesive strip 20. Alternatively, the pull cover may be formed integrally with the carrier from the same sheet of material. The removal of the carrier from the adhesive strip also removes the attached pull cover. Alternatively, the carrier is not attached to the pull cover and is removed separately from it.

The carrier comprises one or more holding means. The holding means functions to enable the user to grasp and hold the carrier and the attached adhesive strip. The pull cover functions as a suitable holding means. An alternative holding means comprises a tab that projects beyond the outer perimeter of the adhesive strip and which is large enough for a user to grasp.

The pull cover extends beyond the perimeter of the adhesive strip so as to form tab 34. The tab 34 preferably extends far enough so that a user can easily grasp and pull it.

Figure 4:
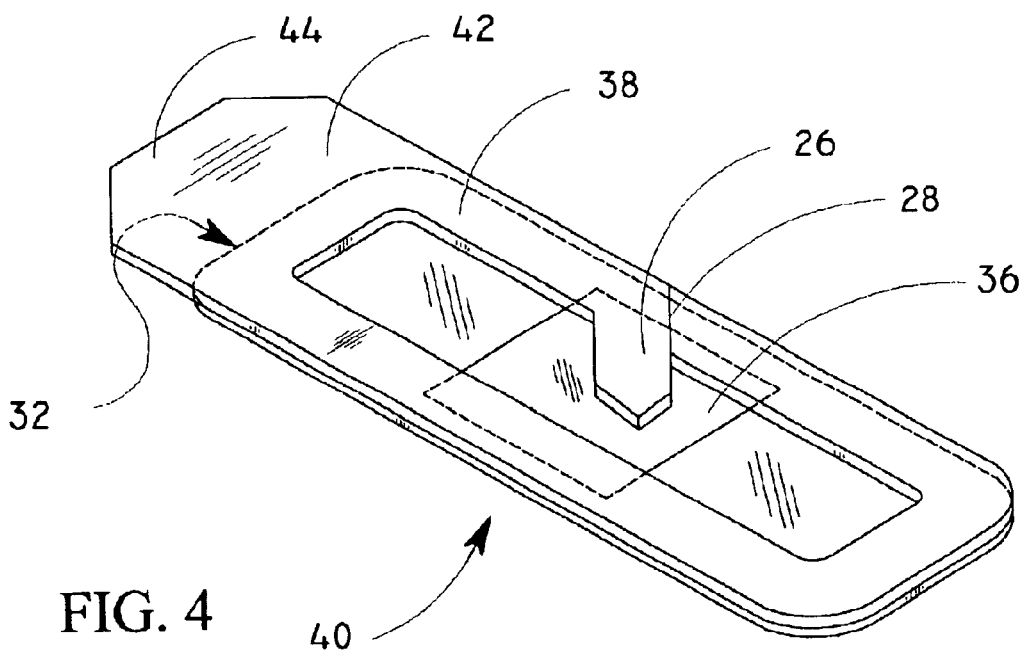
FIG. 4 is a perspective view illustration of an adhesive strip constructed in accordance with the present invention including a partial carrier with an integrally formed pull cover.

A perspective view illustration of an adhesive strip constructed in accordance with the present invention including a partial carrier with an integrally formed pull cover is shown in FIG. 4. A wound pad 36 is attached to the lower planar surface of the adhesive strip 40. The adhesive strip and carrier 38 are constructed similarly to the adhesive strip and carrier of the embodiment shown in FIG. 3. The pull cover 42, however, is formed integrally from the same sheet of material as the carrier 38. The pull cover extends beyond the perimeter of the adhesive strip so as to form tab 44. The tab preferably extends far enough so that a user can easily grasp and pull it.

Figure 5:
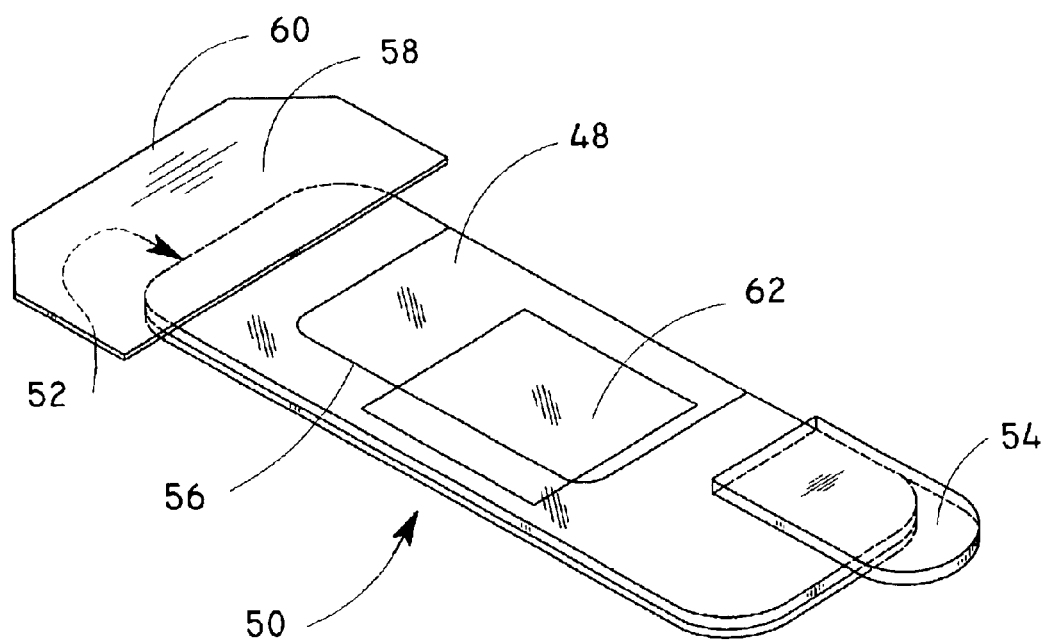
FIG. 5 is a perspective view illustration of an adhesive strip with a full carrier sheet, a pull tab, and a pull cover.

A perspective view illustration of an adhesive strip with a full carrier sheet, a pull tab, and a pull cover is shown in FIG. 5. The carrier 48 is shaped and sized similarly to the adhesive strip 50 so that it is substantially or fully congruent with the adhesive strip. The carrier is preferably bonded to the adhesive strip using a low tactile adhesive. Alternatively, the carrier is attached to the adhesive strip using pressure bonding, thermal bonding, cold bonding or any other suitable means such as is commonly known in the arts. The carrier is bonded more aggressively in the area that lies adjacent to the leading edge 52 of the adhesive strip than in other areas of the adhesive strip in order to prevent the carrier from separating from the adhesive strip during removal of the adhesive strip from the package. In an alternative embodiment, the carrier is bonded to the adhesive strip uniformly.

A pull tab 54 is attached to the carrier thus providing a means for grasping the carrier to remove it from the adhesive strip once the adhesive strip is applied to a desired surface.

In an alternative embodiment, the pull tab is formed integrally from the same sheet of material as the carrier. The pull tab is preferably located substantially opposite the leading edge of the adhesive strip at a point where it will easily separate the carrier from the adhesive strip. The pull tab is folded over itself and may be releasably bonded to a part of the package so that the pull tab unfolds and is easy to grasp once the adhesive strip is removed from the package and applied to the desired surface. In alternative embodiments, the pull tab is not folded. Optionally, the pull tab may be colored permitting the user to readily notice if the carrier has not been removed from the adhesive strip after the adhesive strip has been applied to a desired surface.

A slit 56 is made in the carrier in order to reduce the effort required to remove the carrier from the adhesive strip. The slit is used to direct the progression of separation of the carrier from the adhesive strip so that it will be perpendicular to the more aggressively-bonded area that lies adjacent to the leading edge of the adhesive strip, thereby reducing the width of the bond at the point of separation. This design is less likely to disturb the bond between the adhesive strip and the surface to which it is attached. In an alternative embodiment, the slit may be omitted.

A pull cover 58 is attached to the carrier. The pull cover extends beyond the perimeter of the adhesive strip so as to form a tab 60. The tab should extend far enough so that a user can easily grasp and pull it. An optional wound pad 62 is attached to the lower planar surface of the adhesive strip.

Suitable materials for construction of the carrier comprise without limitation polyethylene, polyester, or any other transparent material and/or polymeric material that is suitable for use with the adhesive strip. Such materials are commercially available and include a 1-2.5RLSF-6000 liner available from the DCP-LOHJA Corp. or a heatsealable polyethylene film no. 9966 available from the 3M Corporation Medical Specialties Division, St. Paul, Minn.

Figure 6A:
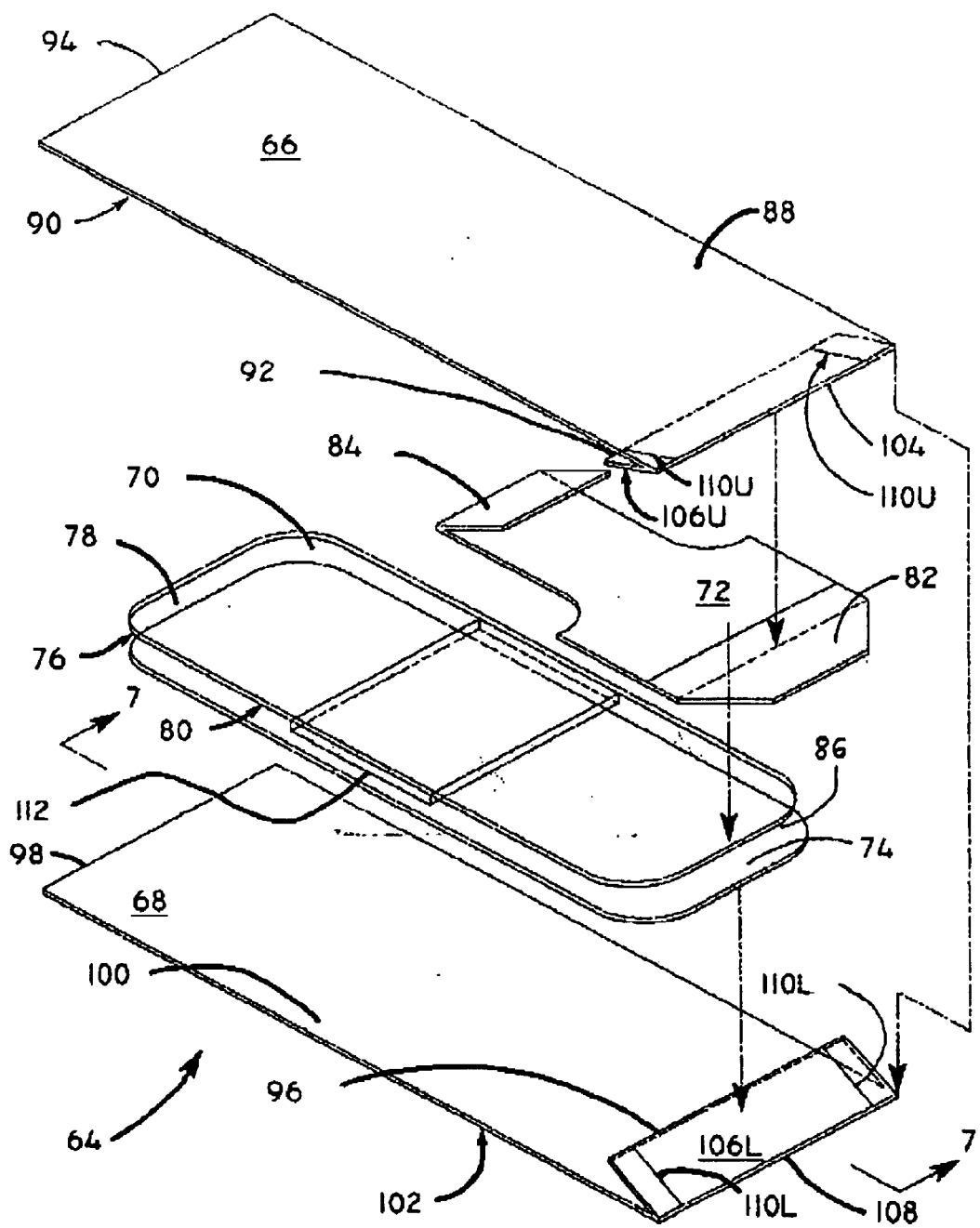
FIG. 6A is an exploded perspective view illustration of the adhesive strip or bandage and dispenser package constructed in accordance with the present invention.

An exploded perspective view illustration of the adhesive strip or bandage and dispenser package constructed in accordance with the present invention is shown in FIG. 6A. The dispenser package comprises a package 64 in which an adhesive strip 70 is incorporated. The package comprises an upper sheet 66, a lower sheet 68, a pull cover 72 and a release liner 74. The adhesive strip can be suitable for medical applications but the invention is not limited to such. The lower surface 76 of the adhesive strip is in direct contact with and is protected by at least one release liner. An adhesive surface 80 is applied to the lower surface of the adhesive strip. The upper surface 78 of the adhesive strip is covered by at least a part of both the upper sheet and the pull cover. Alternatively, the upper surface of the adhesive strip is covered by either the upper sheet or the pull cover.

The release liner preferably has a low coefficient of cohesion so that it is easy to remove from the adhesive strip. Additionally, the release liner is flexible enough so that the flexible strip is easily removed from the package. Release liners are well known in the art, and may comprise, for example, a silicone-coated treated paper such as is available from DCP-LOHJA, Inc. or LOPAREX, Inc., Willowbrook, Ill.

The pull cover has a first tab 82 which is located at an exterior end of the pull cover and an optional pull tab 84 located on the end of the pull cover adjacent to the adhesive strip. The first tab as well as the pull tab (if present) should be sized such that a user may easily grasp it during use. The pull cover is releasably attached to the upper surface of the adhesive strip at a location which is proximate to the leading edge 86 of the adhesive strip using any suitable means which would enable the pull cover to separate the adhesive strip from the release liner when the package is opened. Optionally, the pull cover is also releasably attached to other areas of the adhesive strip. A suitable means of attaching the pull cover to the adhesive strip is by using a low-tactile pressure-sensitive adhesive applied to the pull cover so that the pull cover is releasably attached to the leading edge of the adhesive strip. Other means of attaching the pull cover to the adhesive strip include heat, pressure, cold-bonding, emulsion bonding, cold sealing or any combination of these or other suitable methods as are common and well known in the art. The tenacity of the bond between the adhesive strip and the pull cover should be great enough such that the adhesive strip remains attached to the pull cover until the adhesive strip is applied to a desired object. Care must be taken so that the strength of the bond between the pull cover and the adhesive strip allows the pull cover to be removed from the adhesive strip with minimal effort and without damaging the bond formed by the adhesive surface on the lower surface of the adhesive strip once the adhesive strip has been applied to the desired surface. Alternatively, the pull cover is attached to a carrier (such as is shown in FIGS. 3 through 5 described supra) which is attached to the adhesive strip or is releasably attached to the adhesive surface of the adhesive strip.

The upper sheet 66, has an upper surface 88, a lower surface 90, an interior end 92 and a trailing end 94. Likewise, the lower sheet 68, has an upper surface 100, a lower surface 102, an interior end 96 and a trailing end 98.

The pull cover is releasably attached to the upper sheet 66. Although the pull cover may be attached to the upper sheet at any point along the surface of the pull cover, it is preferred that the pull cover be releasably attached to the upper sheet at a location proximate to the first tab 82 of the pull cover. The pull cover is releasably attached to the upper sheet using a suitable bond that requires minimal effort to separate, and, preferably, employs a low-tactile pressure-sensitive adhesive that is capable of maintaining a sterile seal. Other suitable methods for bonding include heat, pressure, cold-bonding, emulsion bonding, etc. It is preferred that the bond use peel stress to separate. A suitable peel-stress-type bond is formed by folding the upper sheet across its width at fold 104, so as to form an appendage 106U which terminates at an interior end 92 of the upper sheet, wherein the appendage is releasably attached to the pull cover.

In an alternative embodiment, the pull cover is formed from the same sheet of material as the upper sheet using a weakened line to separate the pull cover portion from the upper sheet portion, as is described infra.

The lower sheet 68 is shaped similarly to the adhesive strip 70 but is larger, so as to be capable of forming a seam around the perimeter of the package formed by the combination of the lower sheet 68, the upper sheet 66 and the pull cover. The lower sheet is preferably folded across its width at fold 108, so as to form an appendage 106L which terminates at the interior end of the lower sheet. The appendage is preferably long enough to be capable of forming a releasable bond or seal between the lower sheet and the pull cover and, in certain embodiments (such as the one shown), the upper sheet. This bond or seal is similar to the bond or seal between the upper sheet and the pull cover, as described supra. The upper sheet has one or more scores 110U. Likewise, the lower sheet has one or more scores 110L.

The portion of the appendage 106L that lies between scores 110L and the adjacent outer perimeter of the package is either removed, folded back upon itself or folded back and bonded upon itself in order to reduce or eliminate shear-type forces when the pull cover is removed from the package. This will reduce the force necessary to remove the pull cover from the package. Likewise, depending upon the configuration used, the corresponding area of the upper cover has the same or similar configuration.

In a preferred embodiment, the pull cover is slightly narrower than the package so as to avoid a shear-type bond between the pull cover and both the upper sheet and lower sheet.

The upper sheet and the lower sheet are releasably attached to each other along their outer perimeter except for that portion where they are attached to the pull cover. One suitable method of attaching the upper sheet to the lower sheet comprises a low-tactile pressure-sensitive adhesive. In alternative embodiments, cold bonding, thermal bonding, pressure bonding, or other suitable bonds, which are common in the art, may also be used. Care should be taken so that the upper sheet and the lower sheet can separate far enough from each other so as to allow the adhesive strip to be easily removed from the package. An optional wound pad 112 is attached to the lower planar surface 76 of the adhesive strip.

In alternative embodiments, a blocking member (such as that shown in FIG. 6B infra), which is well known in the art, is used to attach the upper sheet to the lower sheet. The upper sheet and the lower sheet are attached to the adjacent side of the blocking member.

Figure 6B:
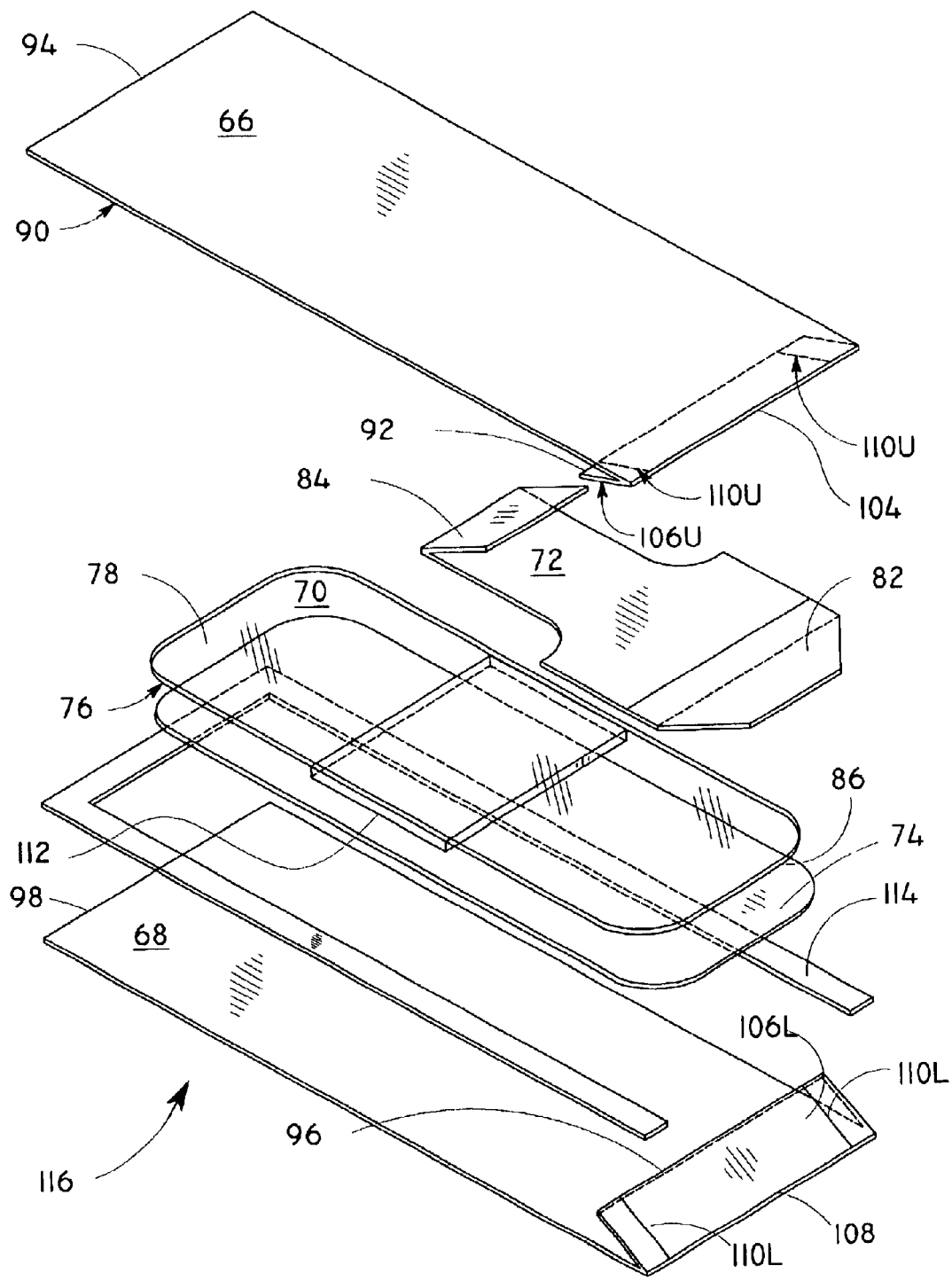
FIG. 6B is an exploded perspective view illustration of the adhesive strip or bandage and dispenser package using a blocking member constructed in accordance with an alternate embodiment of the present invention.

An exploded perspective view illustration of the adhesive strip or bandage and dispenser package using a carrier and blocking member according to an alternative embodiment of the current invention is shown in FIG. 6B. This embodiment (package 116) is similar to the embodiment illustrated in FIG. 6A, the difference being the inclusion of a blocking member 114 which is placed between and attached to both the upper sheet and the lower sheet.

Figure 6C:
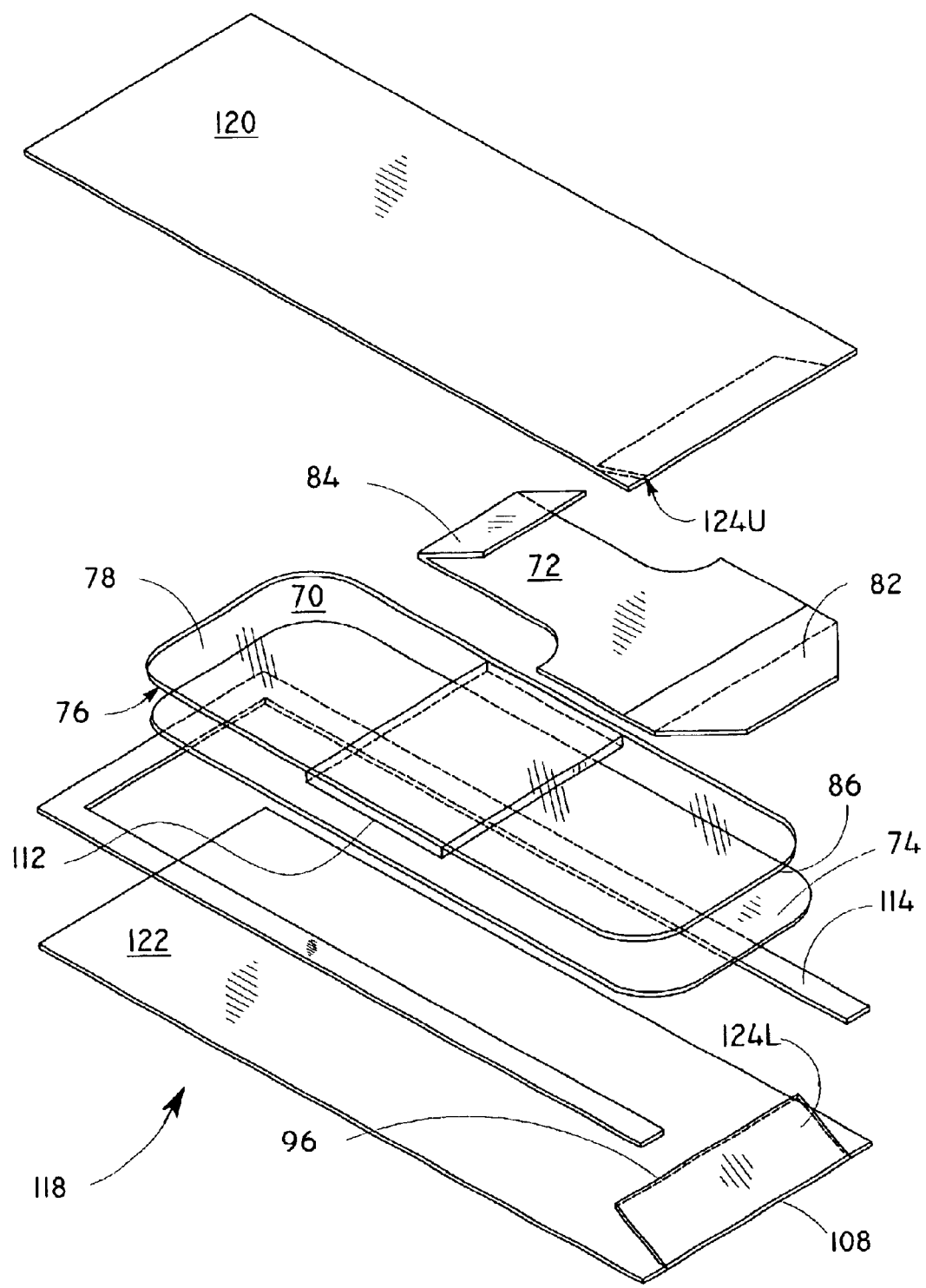
FIG. 6C is an exploded perspective view illustration of the adhesive strip or bandage and dispenser package using a blocking member constructed in accordance with an alternative embodiment of the present invention.

An exploded perspective view illustration of the adhesive strip or bandage and dispenser package using a carrier and blocking member according to an alternative embodiment of the current invention is shown in FIG. 6C. This embodiment is similar to the embodiment illustrated in FIG. 6B, with a difference being the elimination of that portion of the lower sheet's appendage 106L that lies between scores 110L (as shown in FIG. 6B) and the adjacent outer perimeter of the lower sheet, as well as that portion of the upper sheet's appendage 106U that lies between scores 110U (as shown in FIG. 6B) and the adjacent outer perimeter of the upper sheet, so as to form appendages 124L and 124U (as shown in FIG. 6C). Appendages 124L and 124U are located on the lower sheet 122 and the upper sheet 120 of the package 118, respectively.

Figure 7A:
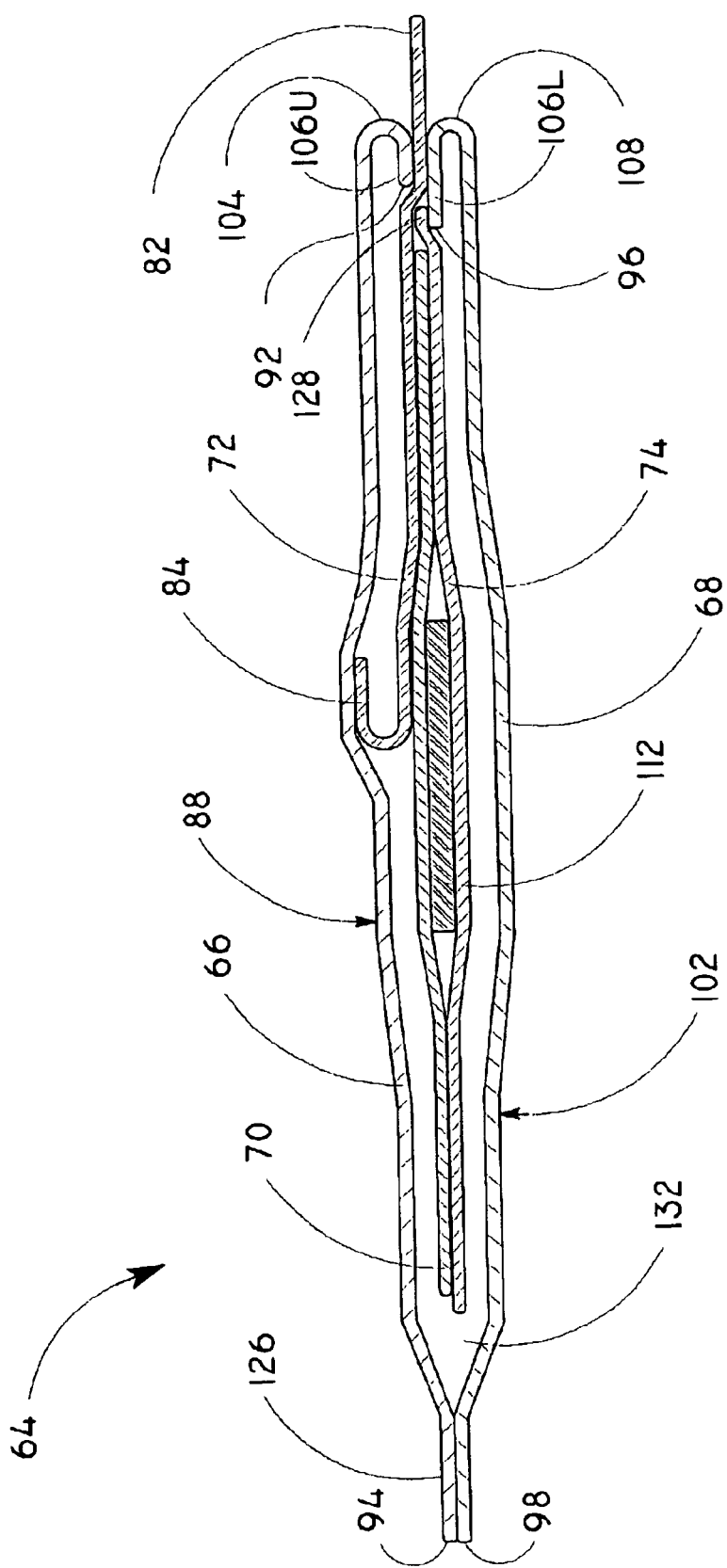
FIG. 7A is cross-sectional view illustration of the adhesive strip or bandage and dispenser package according to the present invention, taken along line 7—7 of FIG. 6A.

A cross-sectional view illustration of the adhesive strip or bandage and dispenser package according to the present invention, taken along line 7—7 of FIG. 6A, is shown in FIG. 7A. The release liner 74 is attached to the appendage 106L of the lower sheet 68 adjacent to the interior end 96 of the lower sheet 68. The bond between the release liner and the lower sheet preferably does not separate in use, and should be able to flex sufficiently in order to facilitate the separation of any bonds adjacent to this bond and so that the adhesive strip 70 can easily be separated from the release liner. The preferred method of joining the release liner to the lower sheet is by overlapping and bonding the leading end 128 of the release liner with the interior end of the lower sheet. Extra material is provided on either or both the lower sheet and the release liner so as to allow the release liner to be bonded to the lower sheet as required. One suitable method of bonding the release liner to the interior end of the lower sheet is by using a high-tactile pressure-sensitive adhesive. Other suitable methods include but are not limited to cold bonding, thermal bonding, pressure bonding, or other methods of bonding which are well known in the arts. In alternative embodiments the release liner may be formed from the same sheet of material as the lower sheet.

The adhesive strip is releasably attached to, and protected by, all or a part of the release liner. The adhesive strip is retained within the package by either or both the release liner and the pull cover. Additionally, the upper sheet 66 and/or the lower sheet 68 may also have a light adhesive to retain the adhesive strip within the package and also provide for a desired amount of friction when removing the adhesive strip from the package.

A second tab 126 is formed by attaching the upper sheet 66 and the lower sheet 68 to each other at a location proximate to either the trailing end 94 of the upper sheet or the trailing end 98 of the lower sheet. The bond between the upper sheet and the lower sheet at this location should be sufficiently aggressive so that these sheets do not substantially pull apart from each other when opening the package 64. Additionally, the second tab 126 should be of sufficient size so that the user can easily grab it during use. In an alternative embodiment, the upper sheet and the lower sheet are formed from one sheet of material by folding the lower sheet across its width (transverse axis) at a location that is adjacent to the trailing end of the lower sheet. Some adhesive is preferably applied between the two sheets so as to bond the two sheets together in the area of the second tab, thus better defining the second tab. Alternatively, the upper sheet and the lower sheet are formed from a single sheet of material which is folded across its longitudinal axis so as to form both the upper sheet and the lower sheet. Additionally, the sheets are bonded together so as to form the package and the second tab. Alternatively, the second tab may be omitted.

Preferably, the upper sheet and the lower sheet are constructed from flexible treated paper as is common in the art. Additionally, the pull cover is preferably constructed from a similar material. Alternatively, other material may be used. In alternate embodiments the second tab may be deleted.

An optional wound pad 112 is attached to the lower surface of the adhesive strip 70. Alternatively, a plurality of wound pads may be used.

Figure 7B:
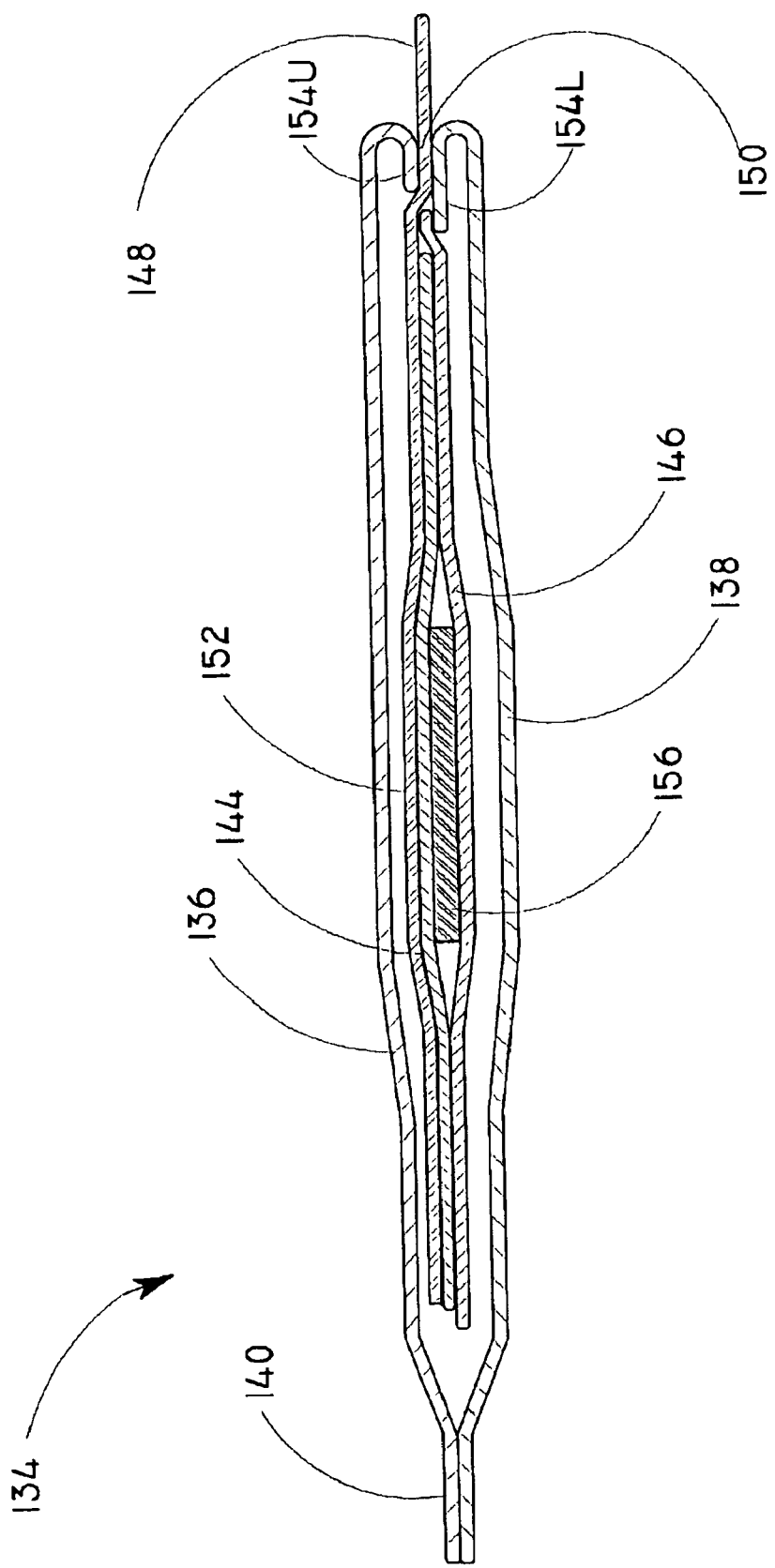
FIG. 7B is a cross-sectional view illustration of an alternative embodiment of the adhesive strip or bandage and dispenser package incorporating a carrier sheet.

A cross-sectional view illustration of an alternative embodiment of the adhesive strip or bandage and dispenser package incorporating a carrier sheet is shown in FIG. 7B. This embodiment, generally referenced 134, is similar to the embodiment shown in FIG. 7A, described hereinabove, a difference being that it uses a full carrier 152 which is formed integrally with the pull cover 150 as shown. The carrier 152 is releasably laminated to the adhesive strip 144 which is releasably attached to the release liner 146.

The adhesive strip 144 is located within the package 134 and held in place by either or both the release liner and/or the pull cover. A low-tack adhesive is optionally applied to either or both the upper sheet 136 and/or the lower sheet 138 in the area where it contacts the adhesive strip 144, the carrier 152 and/or release liner 146, so as to maintain the desired amount of friction when removing the adhesive strip from the package.

The pull cover is releasably attached to the appendage 154U of the upper sheet and the appendage 154L of the lower sheet. A second tab 140 is located opposite the first tab 148. An optional wound pad 156 is attached to the adhesive strip.

Figure 8:
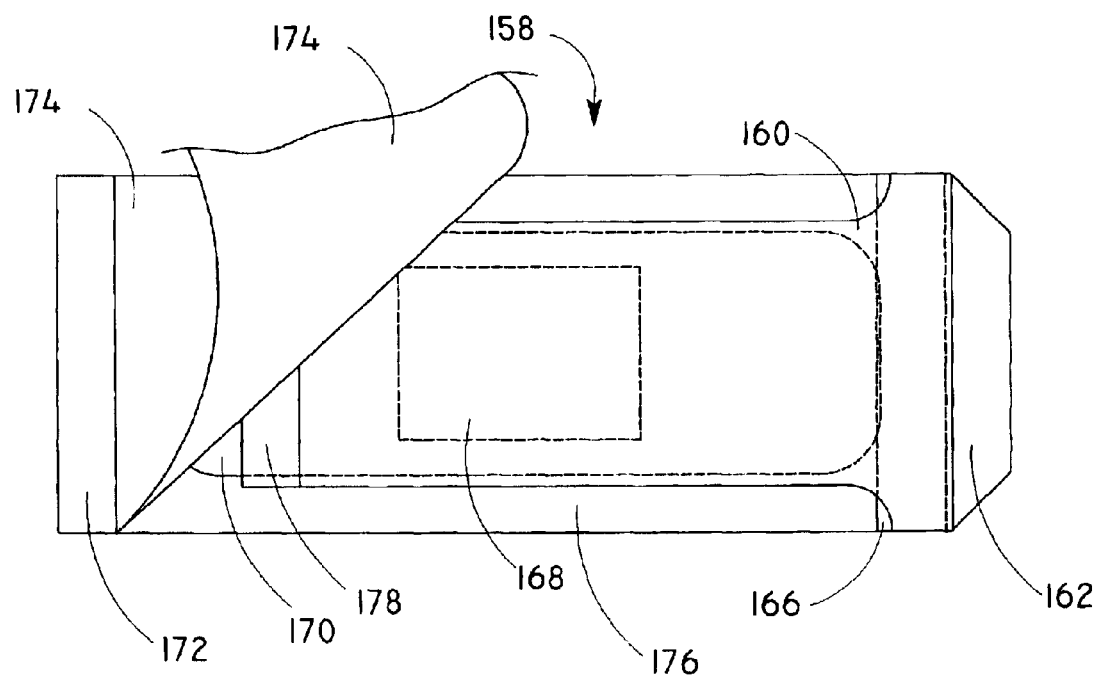
FIG. 8 is a detailed top view illustration of a first alternative embodiment of the pull cover of the present invention with the upper sheet partially peeled away.

A detailed top view illustration of a first alternative embodiment of the pull cover of the present invention with the upper sheet partially peeled away is shown in FIG. 8. The pull cover 160 is as wide as (or wider than) the package 158 in the area where the pull cover is attached to the upper sheet 174 and the lower sheet 176. Scores (as shown in FIGS. 6A and 6B) are eliminated from both the upper sheet appendage (not shown) and the lower sheet appendage 166. The pull cover is releasably attached to the appendages of the upper sheet and lower sheet 176, as described supra. The portion of the pull cover which lies in the interior portion of the package is narrower than the seam that seals the package. The second tab 172 is located opposite the first tab 162. The pull tab 178 is located opposite the first tab 162. The adhesive strip 170 comprises an optional wound pad 168.

Figure 9:
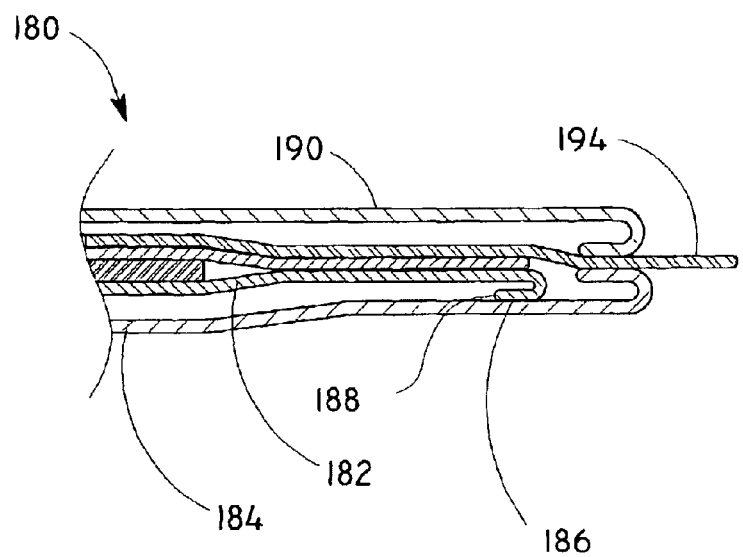
FIG. 9 is a cross-sectional view illustration of a second alternative embodiment of the present invention, which shows the attachment of the release liner to the lower sheet as well as the attachment of the pull cover to both the upper and the lower sheets.

A cross-sectional view illustration of a second alternative embodiment of the present invention, which shows the attachment of the release liner to the lower sheet as well as the attachment of the pull cover to both the upper and the lower sheet, is shown in FIG. 9. The release liner 182 is folded over itself and its leading end 188 is attached to the lower sheet 184 at attachment 186. Alternatively, the release liner is attached to the lower sheet at attachment without the fold. The pull cover 194 is releasably attached to the upper sheet 190 and the lower sheet. It is appreciated that the packaging structure 180 shown here may be used in many embodiments of the present invention. Moreover, these designs may be required in certain embodiments which dispense a plurality of flexible strips from a dispensing pack such as is shown and described hereinbelow.

In alternative embodiments, the release liner is provided with a release means so that at least a major portion of it may be separated from the lower sheet. Without limitation, suitable release means comprises a releasable bond or a weakened line (e.g., either a scored or perforated line) on the lower sheet or on the release liner so as to enable the release liner to be separated from the package 180 after the package is opened.

A cross-sectional view illustration of a third alternative embodiment of the present invention, which shows the attachment of the release liner to the lower sheet as well as the attachment of the pull cover to both the upper sheet and the lower sheet, is shown in FIG. 10A. The pull cover 196 is releasably attached to both the upper sheet 198 and the lower sheet 200 using attachment tabs 204U and 204L. The upper attachment tab 204U is attached to the pull cover and releasably attached to the adjacent upper sheet. Likewise, the lower attachment tab 204L is attached to the pull cover and releasably attached to the adjacent lower sheet 200. Moving the pull cover away from the upper sheet and the lower sheet causes a peel-stress type separation of the bond between the attachment tabs 204U and 204L and the adjacent upper sheet and the lower sheet. The release liner 206 is attached (adjacent to its leading end 218) to the lower sheet at attachment 220. The release liner is releasably attached to the adhesive strip 212 as described elsewhere in this document. Attachment tabs 204 may be reversed if desired (see FIG. 10B). Attachment tab 204U is preferably located proximate to the leading end 208 of the upper sheet. Likewise, attachment tab 204L is preferably located proximate to the leading end 210 of the lower sheet. Alternatively, the upper attachment tab 204U and/or the lower attachment tab 204L may be releasably attached to the pull cover.

A cross-sectional view illustration of a fourth alternative embodiment of the present invention which shows the attachment of the release liner to the attachment tab as well as the attachment or the pull cover to both the upper sheet and the lower sheet, is shown in FIG. 10B. The pull cover 222 is releasably attached to both the upper sheet 224 and the lower sheet 226 using attachment tabs 228U and 228L. The upper attachment tab 228U is attached to the pull cover and releasably attached to the adjacent upper sheet. Likewise, the lower attachment tab 228L is attached to the pull cover and releasably attached to the adjacent lower sheet. Moving the pull cover away from the upper sheet and the lower sheet causes at peel-stress type separation of the bond between the attachment tabs 228U and 228L and the adjacent upper sheet 224 and the lower sheet 226. The release liner 230 is attached (adjacent to its leading end 232) to the lower attachment tab 228L at attachment 234. The release liner is releasably attached to the adhesive strip 212 as described elsewhere in this document. Attachment tab 228U is preferably located proximate to the leading end 236 of the upper sheet. Likewise, attachment tab 228L is preferably located proximate to the leading end 238 of the lower sheet. Alternatively, the upper attachment tab 228U and/or the lower attachment tab 228L may be releasably attached to the pull cover. In alternative embodiments, the lower attachment tab 228L is formed from the same sheet of material as the release liner.

A cross-sectional view illustration, or a fifth alternative embodiment of the present invention, which shows the attachment of the release line to the lower sheet us well as the attachment of the pull cover to both the upper sheet and the lower sheet using an adhesive, is shown in FIG. 10C. The pull cover 242 is attached to the upper sheet 244 and the lower sheet 246 using an adhesive with a low shear-stress component (such as pressure sensitive adhesive with a low shear-stress component) so that the adhesive shears apart when the pull cover is separated from the upper sheet and the lower sheet. The release liner 206 is releasably attached to the adhesive strip 250 and is attached to the lower sheet 246 us described elsewhere in this document. The bond between the pull cover and the upper sheet and the bond between the pull cover and the release liner should be strong enough to hold the pull cover and the A cross-sectional view illustration of a sixth alternative embodiment of the present invention, which shows the attachment of the pull cover to the upper sheet as well as to the release liner using an adhesive, is shown in FIG. 10D. This embodiment is similar to the embodiment shown in FIG. 10C and described supra, a difference being that this embodiment comprises a release liner 252 attached to the lower sheet 262 proximate to the leading end 264 of the lower sheet such that the pull cover 254 is releasably attached to at least a part of the release liner. The pull cover is attached to the upper sheet 260 as described hereinabove. Likewise, the pull cover is attached to either or both the lower sheet and/or the release liner as described hereinabove.

Figure 11:
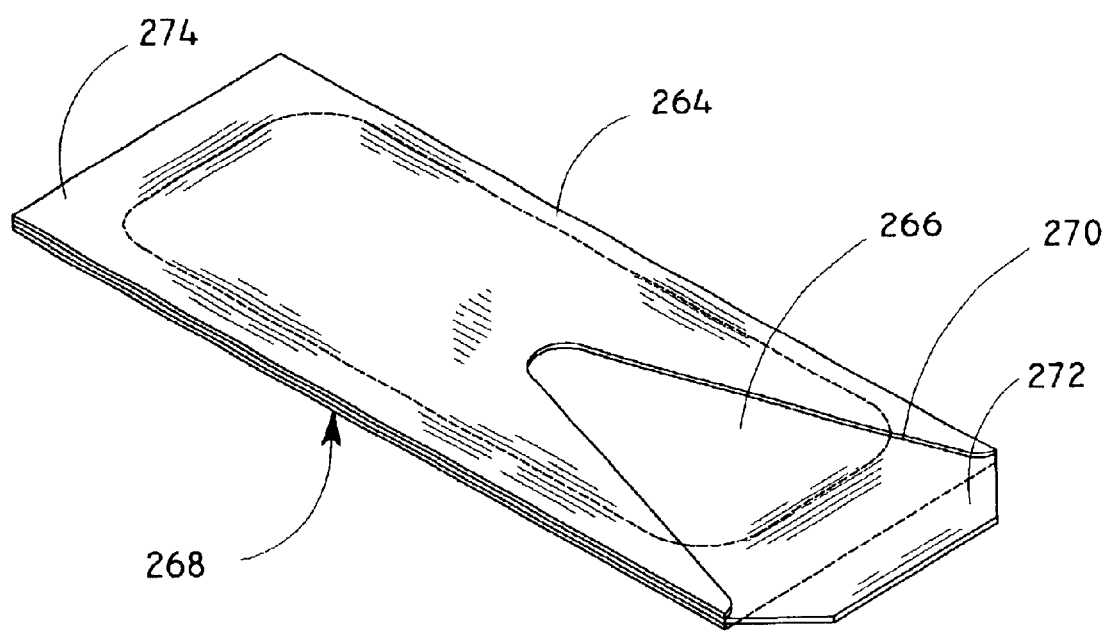
FIG. 11 is a top perspective view illustration of an alternative embodiment of a package of the present invention with a shaped upper sheet.

A top perspective view illustration of an alternative embodiment of the package of the present invention having a shaped upper sheet is shown in FIG. 11. The seam 270 between the upper sheet 264 and the pull cover 266 employs a shear-type bond (e.g., an adhesive). The shape of the upper sheet and the pull cover is such as to indicate which side the pull cover (and the correct top-side) is on. The first tab 272 is opposite the second tab 274. The lower sheet 268 is releasably attached to the pull cover using an appendage. A blocking member (as described elsewhere in this document) is inserted between the upper sheet and the lower sheet. In an alternative embodiment, the pull cover is releasably attached to the lower sheet in a manner similar to that in which the pull cover is attached to the upper sheet, as described in other embodiments of the present invention.

Figures 12A, 12B:
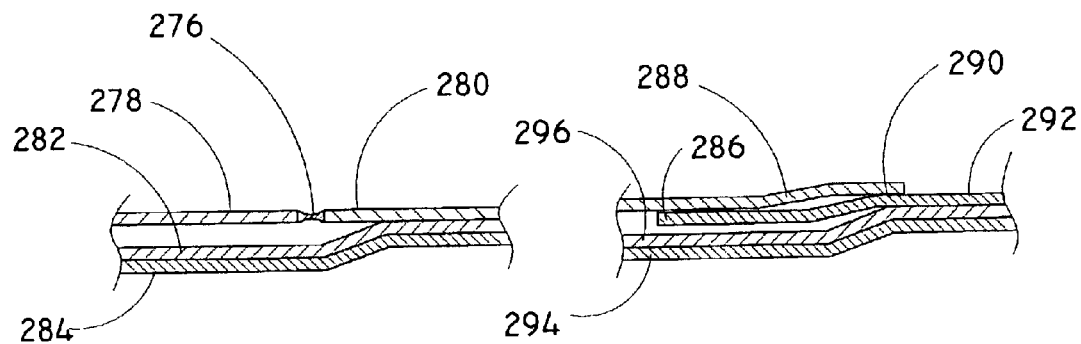
FIG. 12A is a detailed cross-sectional view illustration of a first alternative embodiment of a seam between the pull cover and the upper sheet.
FIG. 12B is a detailed cross-sectional view illustration of a second alternative embodiment of a seam between the pull cover and the upper sheet.

A detailed cross-sectional view illustration of a first alternative embodiment of a seam between the pull cover and the upper sheet bond is shown in FIG. 12A. The seam 276 employs a shear-type bond. The upper sheet 278 and the pull cover 280 are preferably formed from the same sheet of material. The seam is formed by a weakened line in the material that forms the upper sheet and the pull cover. This weakened line is formed by perforating, thinning, or scoring the material. When the pull cover is pulled away from the upper sheet, the weakened line will break, thus separating the pull cover from the upper sheet. The adhesive strip 282 and the release liner 284 are shown for the sake of clarity and are not necessarily attached to the pull cover as indicated. In an alternative embodiment, the pull cover is attached to the lower sheet (not shown) in a similar fashion.

A detailed cross-sectional view illustration of a second alternative embodiment of a seam between the pull cover and the upper sheet bond is shown in FIG. 12B. The seam uses a shear-stress-type bond. The pull cover 292 is releasably attached to the upper sheet 288 at seam 290 using a shear-stress-type bond formed using an adhesive with a low shear-stress type component (or other suitable means as are known in the art). The adhesive strip 296 is shown for purposes of clarity, and is releasably attached to a release liner 294. The pull cover may, if desired, be similarly attached to the lower sheet (not shown). The pull cover 292 includes second tab 286 located adjacent to the trailing end of the pull cover.

Figure 12C:
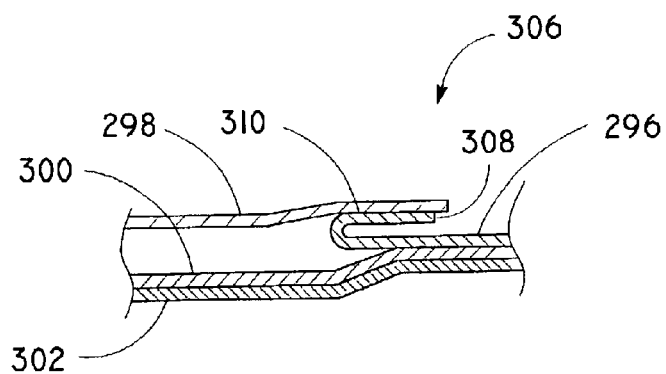
FIG. 12C is a detailed cross-sectional view illustration of a third alternative embodiment of a seam between the pull cover and the upper sheet.

A detailed cross-sectional view illustration of a third alternative embodiment of a seam between the pull cover and the upper sheet bond is shown in FIG. 12C. The seam 306 uses a peel-stress-type bond. The pull cover 296 is attached to the upper sheet 298 using a peel-stress-type bond. The pull cover is folded back over itself and releasably attached to the upper sheet as shown. The adhesive strip layer 300 is shown for purposes of clarity and is releasably attached to a release liner 302. The pull cover may, if desired, be similarly attached to the lower sheet (not shown). The pull cover includes a second tab 310 which is located adjacent to the trailing end 308 of the pull cover.

Figure 13:
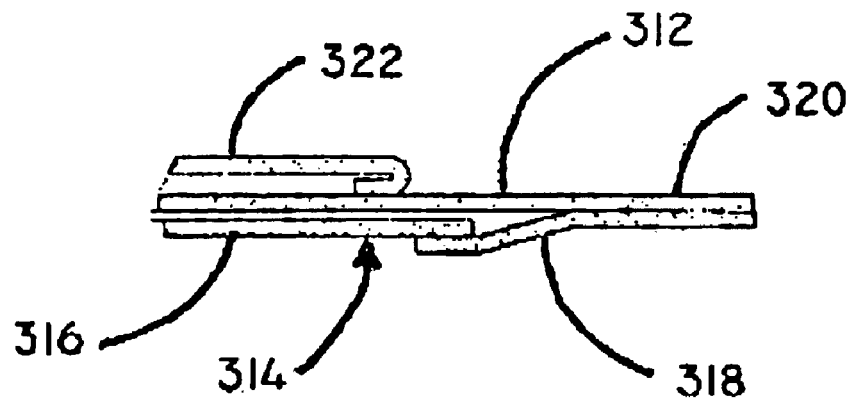
FIG. 13 is a detailed cross-sectional view illustration of a first alternative embodiment of a method of attaching a pull cover to the adhesive strip or bandage.

A detailed cross-sectional view illustration of a first alternative embodiment of a method of attaching a pull cover to an adhesive strip or bandage is shown in FIG. 13. The pull cover 312 is releasably attached to the adhesive surface 314 of the adhesive strip 316 using a tab 318. One end of the tab is attached to the pull cover so as to form the first tab 320. The other end of tab 318 is releasably attached to the adhesive surface of the adhesive strip. Tab 318 is adapted to have a desired coefficient of adhesion in order that it remain attached to the adhesive strip until the adhesive strip is attached to the desired object. The aggressiveness of the attachment is preferably such that the tab 318 remains attached to the adhesive strip until the adhesive strip is applied to a desired object, at which time the tab 318 is able to separate from the adhesive strip without damaging the bond between the adhesive strip and the desired object to which it is attached. In alternative embodiments tab 318 and the pull cover are formed integrally from the same sheet of material. The upper sheet 322 is attached to the pull cover (and/or the combination formed by the pull cover and the attached tab 318) as described in other embodiments of the invention. Likewise, the lower sheet (not shown) is also attached to the combination formed by the pull cover and the attached tab 318 in a similar fashion as discussed elsewhere in this document.

Figure 14:
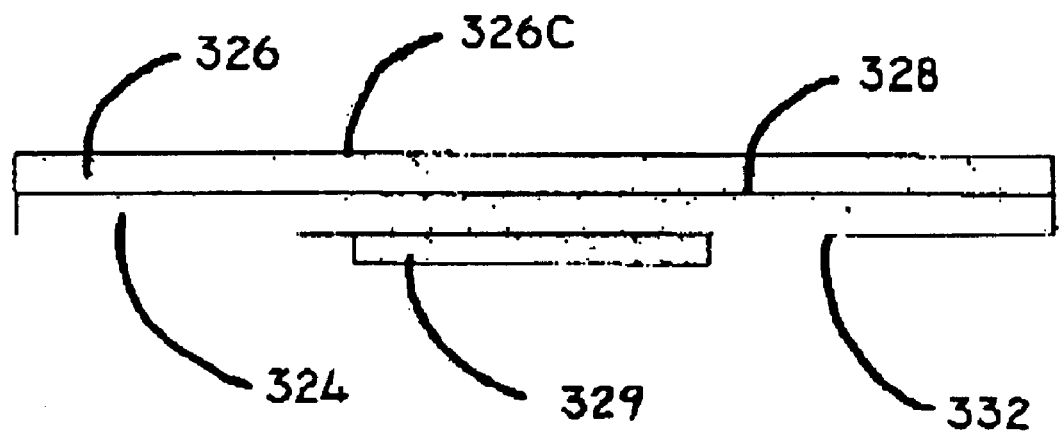
FIG. 14 is a cross sectional view illustration of an alternative embodiment of the adhesive strip having a carrier sheet laminated upon the adhesive strip.

A cross sectional view illustration of an alternative embodiment of the adhesive, strip having a carrier sheet laminated upon the adhesive strip is shown in FIG. 14. The adhesive strip, as used in previous embodiments, is replaced by the combination formed by the adhesive strip 324 and the carrier 326 which is laminated thereto. Depending on the application, the upper surface 328 of the adhesive strip is replaced by the upper surface 324C of the carrier. This structure is described in more detail supra. An optional wound pad 329 may be attached to the lower surface 332 of the adhesive strip.

In various embodiments of the present invention, without limitation, the first tab and the second tab (if present) may he modified to enable the user to more easily use the present invention. Modifications include, for example, (1) colored to contrast with the rest of the package, (2) embossed to enhance user touch, feel, and sight, (3) cut in a way to indicate direction, (4) numbered, embellished with arrows or printed with directions to indicate proper use.

It will be appreciated that the invention is not limited solely to the pull cover designs which are described herein. Any pull cover which functions to meet the requirements as described herein can be used. Thus, a pull cover which can maintain a desired seal between the upper sheet and the lower sheet and releasably hold the adhesive strip so that the adhesive strip may be applied to a desired surface is acceptable regardless of its shape, size, material or other attributes.

In alternative embodiments, either or both the upper sheet and the lower sheet can extend slightly beyond the pull tab so that the pull tab is either partially or fully enclosed and therefore protected from accidental withdrawal. It will also be appreciated that various embodiments of the present invention can also be used to dispense items other than adhesive strips or bandages such as surgical drapes, transdermal patches or the like. In an alternative embodiment, the package or adhesive strip may be inverted so that the adhesive strip emerges with the adhesive surface facing up.

Figure 15:
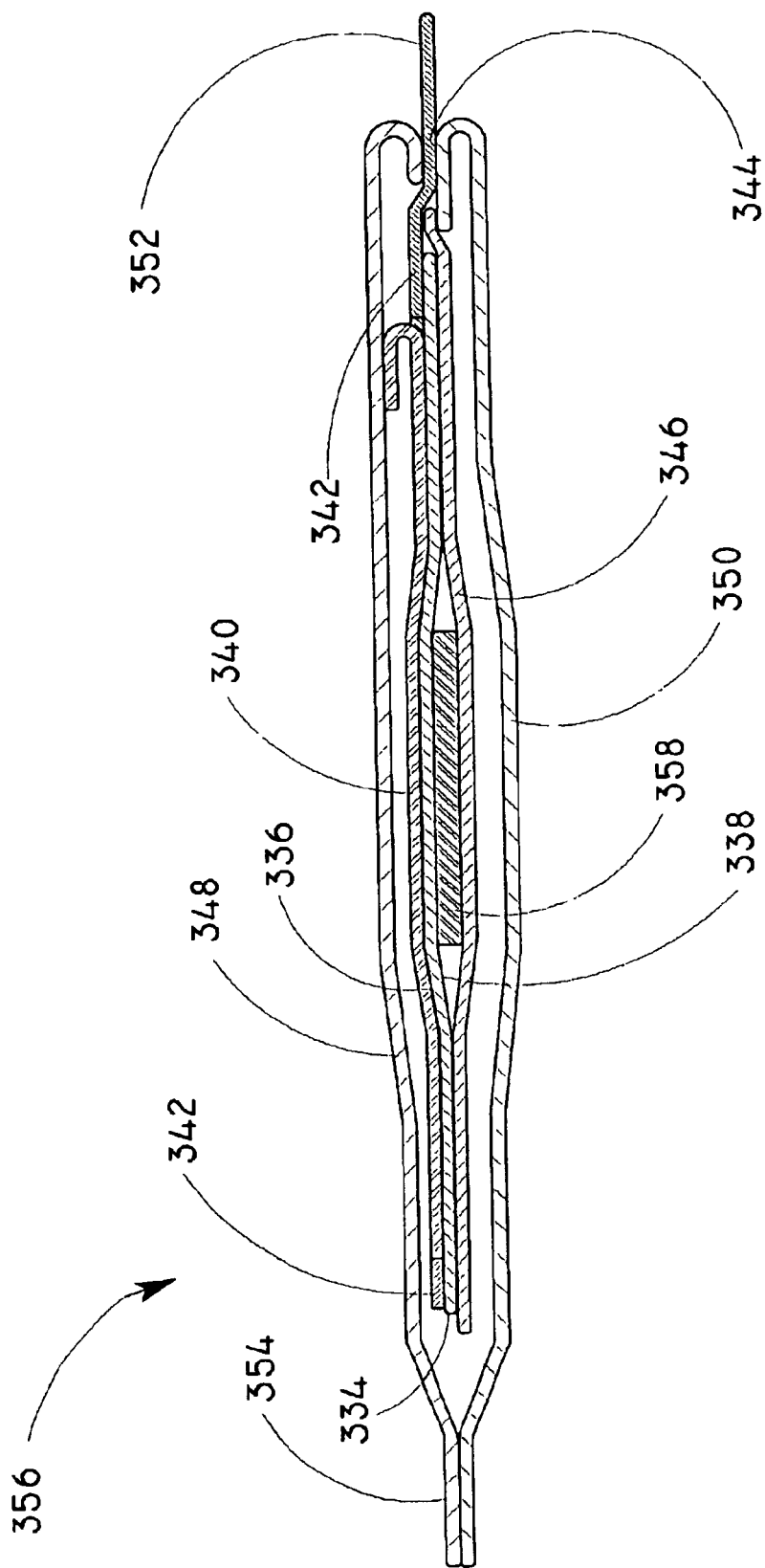
FIG. 15 is a cross-sectional view illustration of an alternative embodiment of the present invention having an adhesive applied to both the upper and lower surfaces of the adhesive strip and including a carrier.

A cross sectional view illustration of an alternative embodiment of the present invention having an adhesive applied to both the upper and lower surfaces of the adhesive strip and including a carrier is shown in FIG. 15. The package 356 is similar to other packages described elsewhere in this document. The package comprises a first tab 352 and a second tab 354. The release liner 346 is attached to the lower sheet 350 and is releasably attached to the adhesive strip 334. The adhesive strip is held in place within the package by the pull cover 344 and/or release liner 346 and/or upper release liner 340.

The adhesive strip has an adhesive applied to both the upper surface 336 and the lower surface 338. A wound pad 358 is optionally attached to the adhesive strip as shown in this example. For example, a carrier 342 (with a window) is attached to the adhesive strip. The upper release liner (which in this example is also a carrier window section) fits within the window formed by the carrier sheet and is releasably attached to the adhesive strip. The upper release liner is removed either (1) automatically during the removal of the pull cover and the adhesive strip from the package in a manner similar to the removal of the release liner or (2) manually after the pull cover and the adhesive strip are removed from the package. If it is desired that the upper release liner be removed during the removal of the pull cover and the adhesive strip from the package, then the upper release liner should be constructed similarly to the release liner and should be attached to the upper sheet 348 in a manner similar to that whereby the release liner is attached to the lower sheet as described elsewhere in this document. Alternatively, if it is desired that the upper release liner be removed from the adhesive strip after the package is opened, then the upper release liner should be shaped and sized similar to or larger than, that upper portion of the adhesive strip which has adhesive applied to it to protect the adhesive which is applied to the upper surface of the adhesive strip and should not hinder the operation of the invention. Additionally, the upper release liner should include a means (e.g., a tab) to aid the user in removing it from the adhesive strip.

Additionally, if the adhesive strip or bandage comprises a carrier "window" (e.g., such as that which is used in 3M TEGADERM™ Transparent Dressings, Original Frame Style, numbers 1634, 1626, 1628, and 1629, see 3M product catalog) (which is similar to the upper release liner 340 as shown and will henceforth also be called a carrier window section) which must be removed before application of the adhesive strip or bandage to the desired surface, then the carrier window section may be attached to either the upper sheet or the lower sheet in a manner similar to that by which the release liner is attached to the lower sheet as described hereinabove. This would allow for the removal of the carrier "window" section during the removal of the adhesive strip or bandage from the package while leaving the carrier (if present) attached to the adhesive strip until after the adhesive strip is attached to a desired object. It is noted that the upper surface of adhesive strips which use carrier window sections, generally have either no adhesive applied or have an adhesive which is not noticeable.

Figure 16:
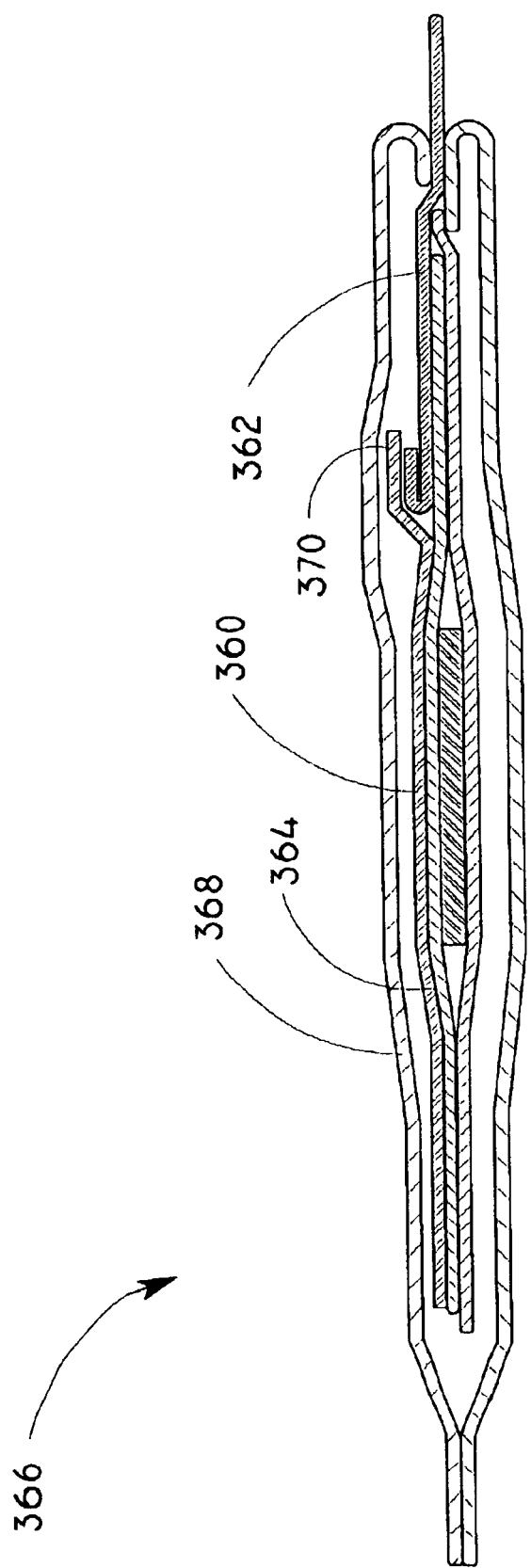
FIG. 16 is a cross sectional view illustration of an alternative embodiment of the present invention having an adhesive applied to both the upper and lower surfaces of the adhesive strip.

A cross sectional view illustration of an alternative embodiment of the present invention having an adhesive applied to both the upper and lower surfaces of the adhesive strip is shown in FIG. 16. This embodiment is similar to the embodiment illustrated in FIG. 15, with a difference being the elimination of the carrier sheet. The upper release liner 360 is removed manually after the pull cover 362 and the adhesive strip 364 are removed from the package 366. Alternatively, the leading end 370 of the upper release liner is attached to the adjacent upper sheet 368 so that the upper release liner is removed automatically during the removal of the pull cover and the adhesive strip from the package, in a manner similar to that whereby the release liner is removed, as described elsewhere in this document.

A cross-sectional view illustration of a seventh alternative embodiment of the present invention, showing a pull cover extending through an opening in the upper sheet is shown in FIG. 17. The package 650 comprises an upper sheet 652, a lower sheet 654, a pull cover 606 and a release liner 658. An adhesive strip 624 is contained within the package. The lower sheet 654 has an upper surface 654U, a lower surface 654L, a leading end 656 and a trailing end 612. The upper sheet 652 has an upper surface 652U, a lower surface 652L, a leading end 614, a trailing end 618, an opening 620 and an appendage 622. The opening is located proximate to the leading edge 638 of the adhesive strip so that the adhesive on the lower surface of the adhesive strip does not come into contact with either the upper sheet or the lower sheet during removal of the adhesive strip from the package. It should be noted that for the sake of clarity, the drawings depict the leading edge of the adhesive strip as set back from the opening. The adhesive strip is releasably attached to the release liner. The adhesive strip is held within the package by the pull cover and/or the release liner. The adhesive strip is preferably suitable for medical applications, but is not limited to such, and has an optional wound pad 628 attached thereto.

The pull cover 606 has a first tab 630, which is suitable for grasping. The pull cover is partially inserted through the opening 620 of the upper sheet 652 so that the first tab extends beyond the exterior of the package 650, such that the pull cover and/or the first tab may be grasped by a user. The pull cover is releasably attached to the adhesive strip 624 proximate to the leading edge 638 of the adhesive strip so that the leading edge of the adhesive strip peels away from the release liner when the pull cover is slidably displaced relative to the package. A pull tab 648 suitable for grasping is attached to the pull cover and is located in the interior of the package opposite the first tab. In alternative embodiments, the adhesive strip includes a carrier sheet. In yet other alternative embodiments, the pull cover is formed integrally with the optional carrier.

The pull cover is releasably attached to the upper sheet's appendage 622 using an low-tactile adhesive so as to form a peel stress type bond. The pull cover is also attached to the upper surface 652U of the upper sheet at the exterior bond 660 using a low-tactile adhesive as described elsewhere in this document. Depending upon application, the exterior bond may be broken using either or both peel or shear-type stress. For example, when opening the package, the exterior portion of the pull cover may be peeled away from the upper sheet before the pull cover is slidably removed from the package or the pull cover may be slidably pulled in a direction opposite that of the second tab, thus breaking the exterior bond using a shear-type force. An optional lower attachment tab (not shown) can be used to secure the pull cover to the lower sheet. If used, the lower attachment tab (as shown elsewhere in this invention) can overlap the opening so as to seal the interior of the package, but, should be carefully positioned so that it has enough room to move as it releases itself from either the lower sheet or the pull cover. Additionally, if the lower attachment tab is used, it should be placed accordingly so that it does not contact the adhesive on the lower surface of the flexible strip.

A detailed top-view illustration of the adhesive strip or bandage and dispenser package of FIG. 17 with the upper sheet peeled back is shown in FIG. 18. Those portions of the pull cover 606 which must pass through the opening 620 are as wide as, or narrower than, the length L of the opening so that the pull cover can pass through the opening without undue force. Likewise, the carrier 626 (if present), the adhesive strip 624 and the release liner 658 should be as wide as or narrower than the length L of the opening so that they can pass through the opening without undue force. Alternatively, if the upper sheet 652 is made from a material which can yield or rip easily, then the pull cover, the adhesive strip 624 and/or the release liner 658 may be wider than the length L of the opening but not so wide as to require undue force when the package is opened. The length L of the opening should be sized sufficiently so that the adhesive strip, the interior portions of the pull cover and the release liner can pass through the opening without requiring undue force. In alternative embodiments, the exterior portion of the pull cover (which does not pass through the opening when the adhesive strips are dispensed), may be wider than the length L of the opening and releasably attached to upper sheet so that it seals the interior cavity of the package. In yet other alternative embodiments, the exterior portion of the pull cover can be folded over itself and releasably attached to the upper surface of the upper sheet so that the pull cover completely seals the opening of the package.

An optional weakened line (e.g., a scored or perforated line) is placed transversely across the release liner so that all, or part of, the release liner may be removed from the lower sheet 654 after the adhesive strip is removed from the release liner. In an alternative embodiment, the release liner can be releasably attached to the lower sheet using a releasable adhesive which would keep the release liner attached to the lower sheet until after the adhesive strip is removed from the package after which the release liner can be separated from the lower sheet.

The appendage 622 is formed by cutting the upper sheet on three sides along the perimeter at the opening and then folding the excess material back upon itself so as to form the appendage. Alternatively, an attachment tab, as described elsewhere in the invention can be used. The methods used to attach the pull cover to the upper sheet and the lower sheet, the upper sheet to the lower sheer, and the release liner to the lower sheet, arc similar to those described elsewhere in this invention.

In alternative embodiments the side exterior portions of the pull cover extend over the sides or the opening for sealing the interior of the package. The pull cover superposes and is releasably attached to those portions of the upper sheet around the circumference of the opening. For example, the exterior portion of the pull cover is wider than the opening and is extended, folded over itself, and releasably attached to the upper sheet so as to seal the interior of the package. In optional embodiments, either or both the upper sheet and/or the lower sheet can be extended so as to form a plurality of packages.

Figure 19:
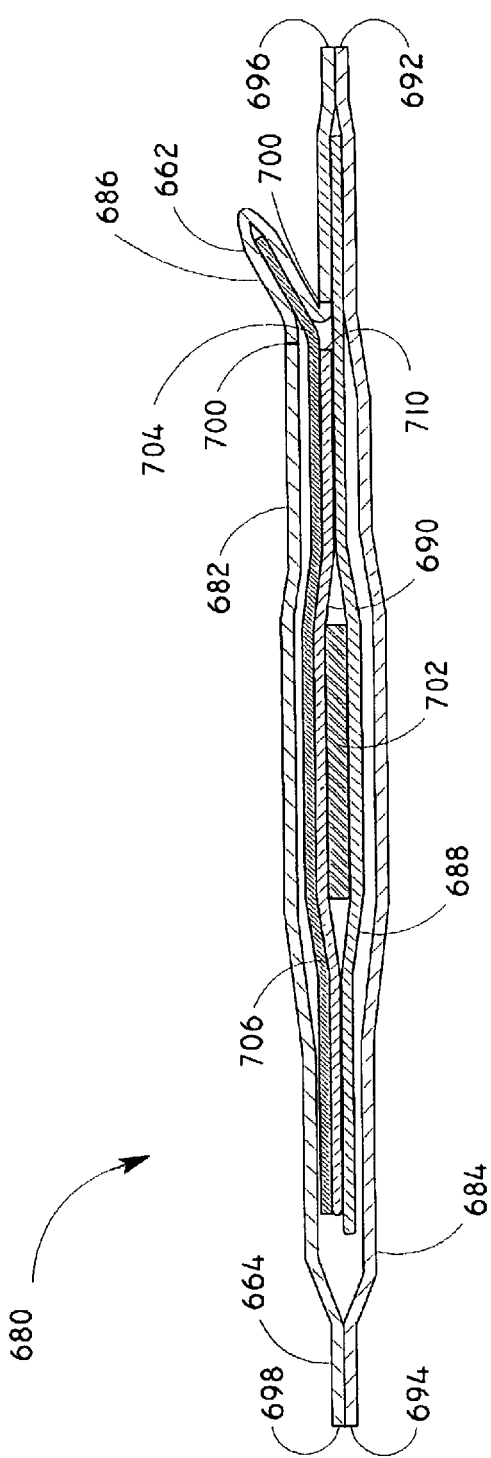
FIG. 19 is a cross-sectional view illustration of the adhesive strip or bandage and dispenser package according to an eighth alternative embodiment of the present invention using an integral upper sheet and pull cover.

A cross-sectional view illustration of the adhesive strip or bandage and dispenser package according to an eighth alternative embodiment of the present invention using an integral upper sheet and pull cover is shown in FIG. 19. The package 680 comprises an upper sheet 682, a lower sheet 684, a pull cover 686, and a release liner 688. An adhesive strip 690 is contained within the package 680. The lower sheet 684 has a leading end 692, and a trailing end 694. The upper sheet 682 has a leading end 696, a trailing end 698, weakened lines 700 which define the two longitudinal sides of an opening.

The adhesive strip 690 is releasably attached to the release liner 688. A carrier 706 is releasably laminated upon the adhesive strip. An inner pull cover 704 (which is similar to the pull covers as described elsewhere in this document) is formed integrally with a carrier from the same sheet of material, and is releasably attached to the adhesive strip (as described elsewhere in this invention). The inner pull cover should not be as wide as the upper sheet 682 so that the upper sheet can be sealed to itself around the outer perimeter of the pull cover as shown. The release liner is attached to the lower sheet. An optional wound pad 702 can be attached to the adhesive strip.

The upper sheet superposes, and is attached to, the lower sheet so as to form a cavity for enclosing the adhesive strip and an optional second tab 664. The pull cover 686 is formed by folding an area of the upper sheet between the weakened lines 700 (3 (e.g., scoring, perforating, etc.) around the inner pull cover and laminating it thereto using any suitable means (e.g., pressure or adhesive, etc.) to form a pull cover which extends so as to form a fist tab 662 suitable for grasping. The opening is defined by the weakened lines 700 which are placed proximate to the leading edge 710 of the adhesive strip and extend transversely across the width of the upper sheet. The opening should be large enough so that the inner pull cover, the adhesive strip, the release liner, the wound pad and the carrier 706 can pass through it without undue force. Depending upon the flexibility of the release liner, it may be desirable to provide a fold or weakened line (e.g., a score or perforation) in the release liner, at a location that is somewhere between the leading edge of the adhesive strip and where the release Liner is attached to either or both the lower sheet and/or the upper sheet so that the release liner can fold easily over itself when the bandage is removed from the package. The upper sheet is optionally attached to the release liner.

Although the pull cover is shown extending outward at an angle from the upper sheet, the pull cover can also lie flat against the upper sheet, be folded over itself, etc. as desired. The methods used to attach the lower sheet to the upper sheet and the release liner; the adhesive strip to the release liner and carrier and/or pull cover combination; are similar to those described elsewhere in this invention. In alternative embodiments, the release liner can be folded proximate to the leading edge of the adhesive strip and is attached to the lower sheet, as shown and described elsewhere in this document; the pull cover may not be formed integrally with the optional carrier; the bandage may not have a carrier laminated upon it; and the upper sheet may be folded around the pull cover and not bonded to it.

Figure 20:
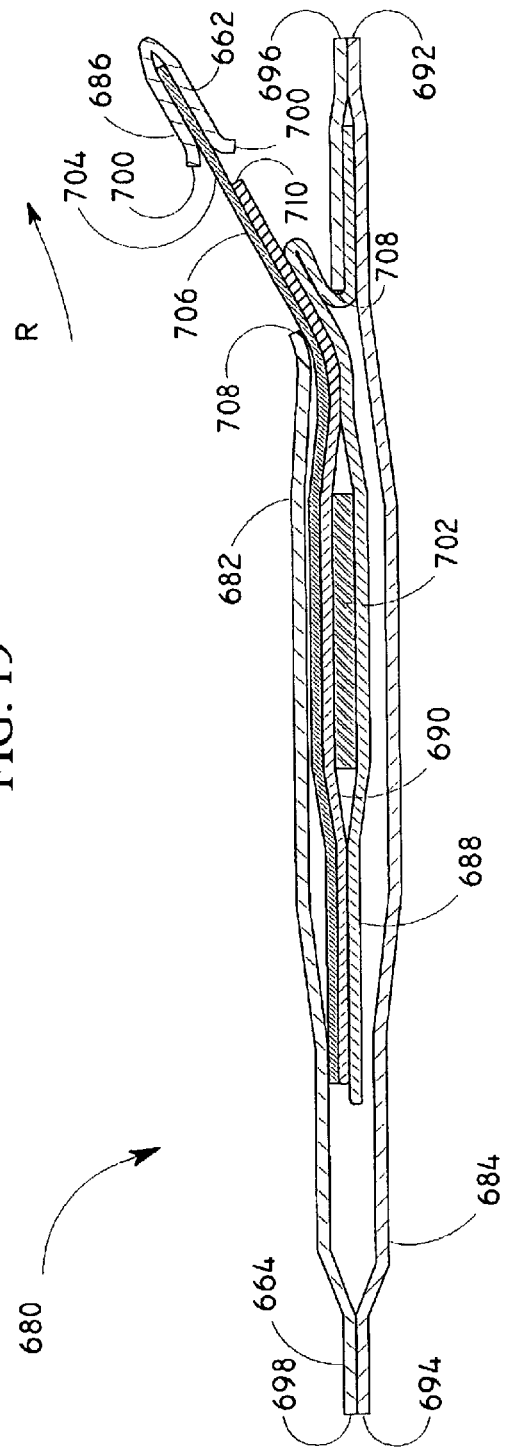
FIG. 20 is a cross-sectional view illustration of the adhesive strip or bandage and dispenser package of FIG. 19 as it is being opened and the bandage contained within is removed.

A cross-sectional view illustration of the adhesive strip or bandage and dispenser package of FIG. 19 as it is being opened and the bandage contained within is removed is shown in FIG. 20. The package 680 is held by a holding means (e.g., the user holding the second tab 664 or a dispenser holding either or both the upper sheet and/or the lower sheet). The first tab 662 and/or pull cover 686 is pulled in a direction (as indicated by arrow R for illustration) substantially opposite that of the trailing end 694 (and the optional second tab 664) of the lower sheet which causes the upper sheet 682 to break apart at the weakened lines 700 thus forming an opening which is defined by transverse lines 708 (which extend across the width of the upper sheet). The adhesive strip 690 and the attached interior portion of the inner pull cover 704, the attached release liner 688 and the optional carrier 706 are pulled through the opening 708. The release liner begins to separate from the adhesive strip and continues separating until the adhesive strip fully detaches from the release liner. The adhesive strip is applied as described in other embodiments of this invention.

A detailed cross sectional view illustration of the adhesive strip or bandage and dispenser package of FIG. 19 with an first alternate pull cover is shown in FIG. 21. The package 770 is essentially similar to that shown in FIGS. 19 and 20 above, with a difference being that the pull cover 772 is formed from a separate sheet of material than the upper sheet 774. The upper sheet has an opening (which is defined by two transverse lines 780) which extends across the width of the upper sheet. The pull cover is laminated upon the inner pull cover 776 and releasably attached to the outer surface of the upper sheet using an adhesive or other bonding method as is know in the art and described elsewhere in this document. The pull cover extends transversely across the width of the upper sheet so that it fully encloses the opening. The pull cover also extends so as to form a first tab 778 which is suitable for grasping.

A detailed cross sectional view illustration of the adhesive strip or bandage and dispenser package of FIG. 19 having a second alternative embodiment of the pull cover is shown in FIG. 22. The package 782 is essentially similar to that shown in FIG. 21 above, with a difference being that the opening is defined by longitudinal sides 784 (only one side is shown) and intersecting transverse sides 786 (as opposed to transverse sides 780 only as shown in FIG. 21). The pull cover 788 is formed from a separate sheet of material than the upper sheet 790. The pull cover is laminated upon the inner pull cover 796 and releasably attached to the outer surface of the upper sheet using an adhesive or other bonding method as is know in the art and described elsewhere in this invention. The pull cover extends transversely across the width of the upper sheet so that it fully encloses the opening. The pull cover 792 also extends so as to form a first tab 794 which is suitable for grasping.

A detailed cross sectional view illustration of the adhesive strip or bandage and dispenser package of FIG. 19 having a third alternative embodiment of the pull cover is shown in FIG. 23. The package 796 is essentially similar to that shown in FIGS. 19 and 20 above, with a difference being that the pull cover 798 is releasably attached to the upper surface of the upper sheet 800 adjacent to the first end of 802 of the pull cover using an shear-type bond (e.g., a low tactile adhesive). The pull cover is releasably attached to the upper sheet adjacent to the second end 804 of the pull cover at weakened line 806 (e.g., scoring, perforating, etc.). The opening is defined on one side by the transverse side 808 and on the other side by the weakened line both of which extend across the width of the upper sheet. The pull cover is laminated upon the inner pull cover 810 as described above. The pull cover extends transversely across the width of the upper sheet so that it fully encloses the opening. The pull cover also extends so as to form a first tab 812 which is suitable for grasping.

In alternative embodiments, the weakened line is removed so that the pull cover extends to the leading end of the lower sheet. The pull cover is attached to the lower sheet using an adhesive. The opening is then defined by the transverse line and the other side by a releasable adhesive bond which joins the pull cover to the lower sheet.

Figure 24A:
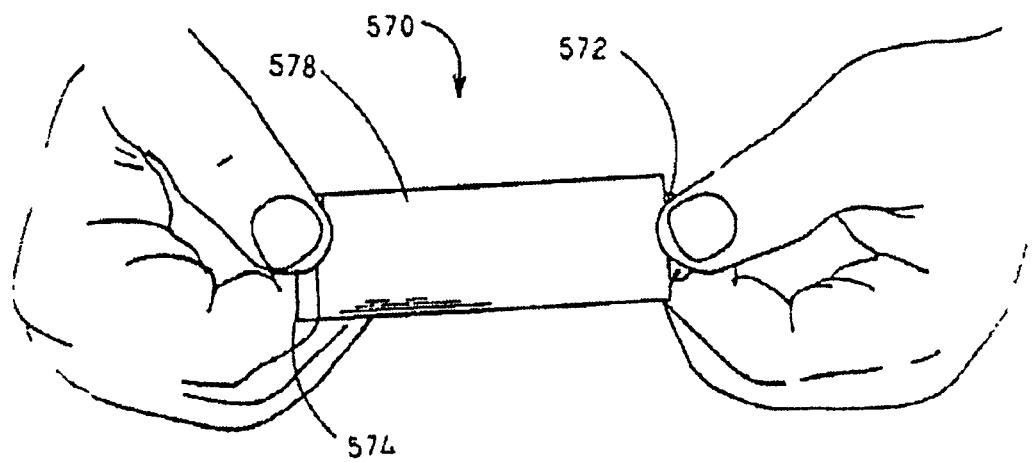
FIGS. 24A and 24B are perspective view illustrations of an individual bandage package of the present invention being opened and the adhesive strip being removed from the package.
Figure 24B:
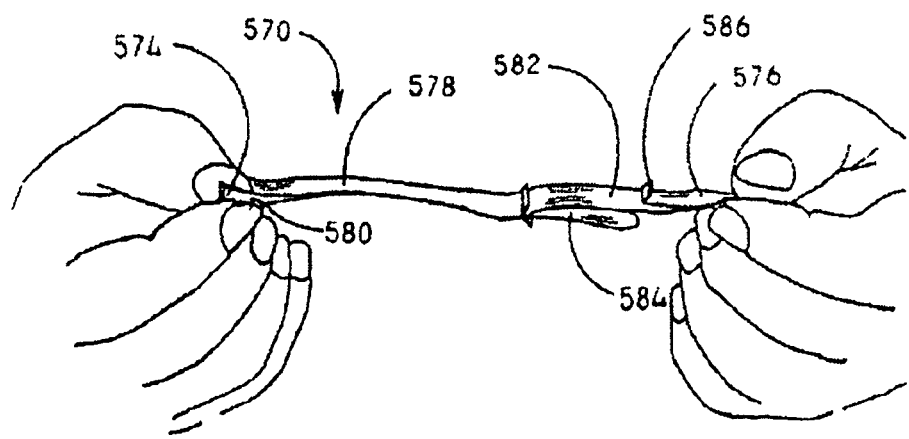

A perspective view illustration of an individual package of the present invention as it is opened and the adhesive strip being removed from the package is shown in FIGS. 24A and 24B. The package 570 is held by the first and second tabs 572, 574, respectively. The user then pulls the first and second tabs in opposite directions, which causes the pull cover 576 to break its bond with the upper sheet 578 and the lower sheet 580. The flexible strip (or bandage) 582 then separates from the release liner 584 beginning at the leading edge of the flexible strip (or bandage) and continues separating until the flexible strip (or bandage) fully detaches from the release liner. During the separation of the flexible strip (or bandage) from the release liner, the release liner folds over itself and is pulled out of the envelope formed by the upper and lower sheets. After the pull cover and the attached flexible strip (or bandage) are separated from the upper sheet, the lower sheet and the release liner, the flexible strip (or bandage) is applied to the desired surface with the aid of the pull cover, the first tab and any other optional holding means. The flexible strip (or bandage) is then applied to the desired surface.

Figure 24C:
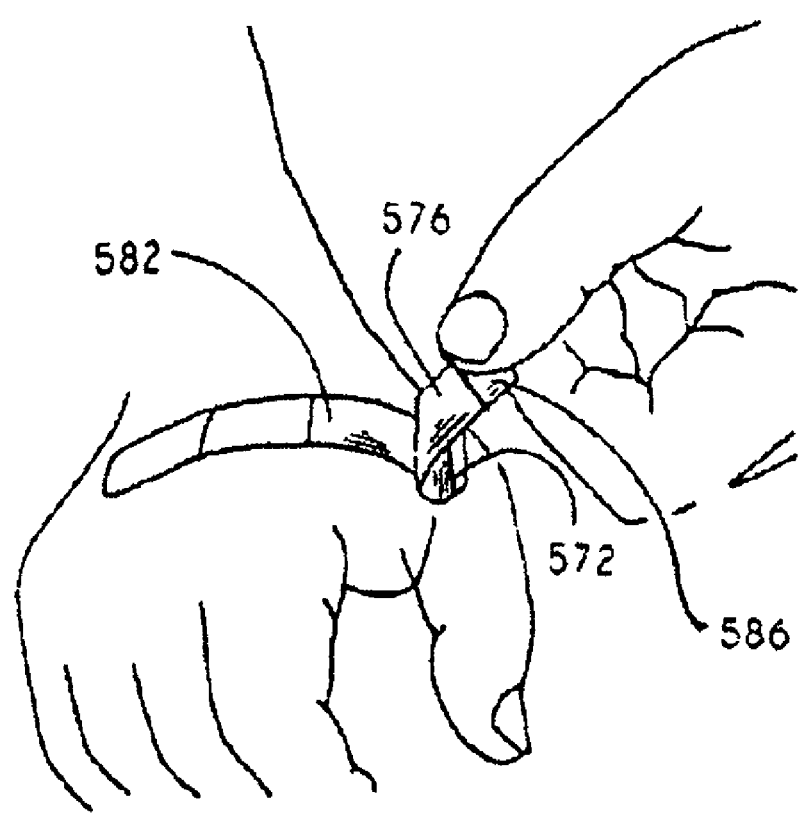
FIG. 24C is a perspective view illustration of a pull cover being removed from an adhesive strip of the present invention that has been applied to a user's hand.

A perspective view illustration of a pull cover being removed from an adhesive strip of the present invention that has been applied to a user's hand is shown in FIG. 24C. The pull cover 576 is removed by pulling the pull tab 586 so that the pull cover is pulled back over itself and separated from the bandage 582. The pull cover is then discarded. If a single package is used alone, the package is then discarded. Alternatively, if a dispenser pack is used, then the release liner is optionally separated from the remainder of the package and discarded.

The present invention provides several schemes for dispensing a plurality of flexible strips, adhesive strips, bandages, or other elements, as described elsewhere in this document, from a dispensing pack. These are illustrated in FIGS. 25 through 45B. The dispensing pack comprises a plurality of packages arranged in rows so as to form a dispensing pack. It should further be noted that the rows can be staggered, if desired. Each scheme will now be described in more detail.

Figure 25:
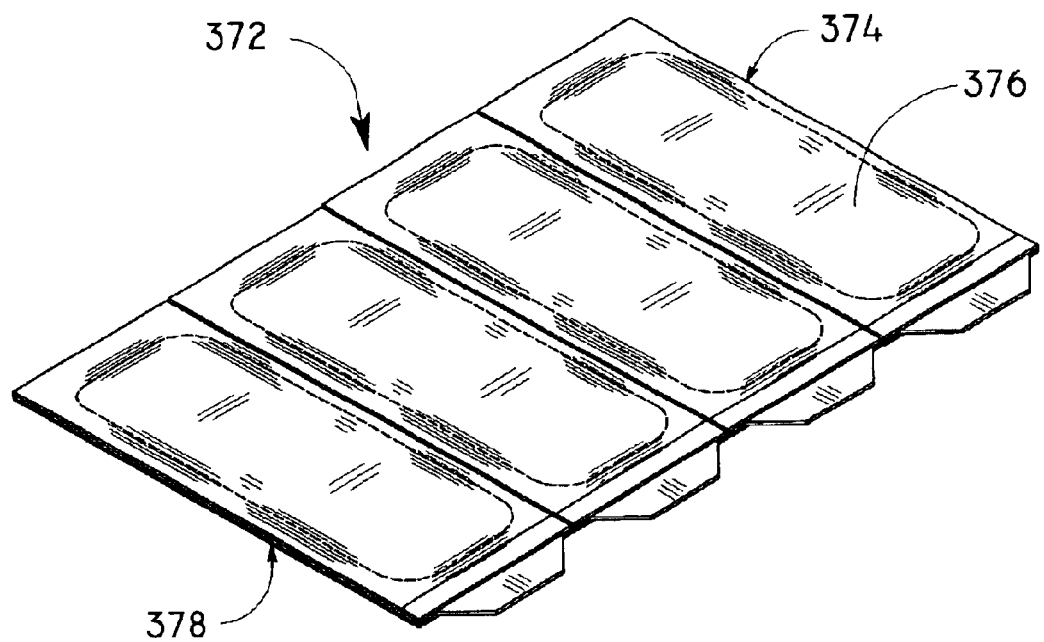
FIG. 25 is a perspective view illustration of a first embodiment of a dispensing pack.

A perspective view illustration of a first embodiment of a dispensing pack is shown in FIG. 25. A plurality of packages 374 are aligned along their longitudinal axis in the same or substantially the same plane (which may include a curved plane). A means for holding individual packages functions to hold the packages in close proximity to one another. A suitable means for holding individual packages in alignment comprises a continuous upper sheet 376 and/or lower sheet 378 long enough such that multiple packages can be mounted thereto. A rigidity-enhancing means is associated with either the lower sheet or the upper sheet. In an alternative embodiment, either the lower sheet or the upper sheet is constructed from a substantially rigid material. A means for holding the dispensing pack 372 is used to hold the dispensing pack in position for dispensing the adhesive strips. If a suitable means for holding the dispensing pack is employed, then the second tab may be omitted.

Figure 26:
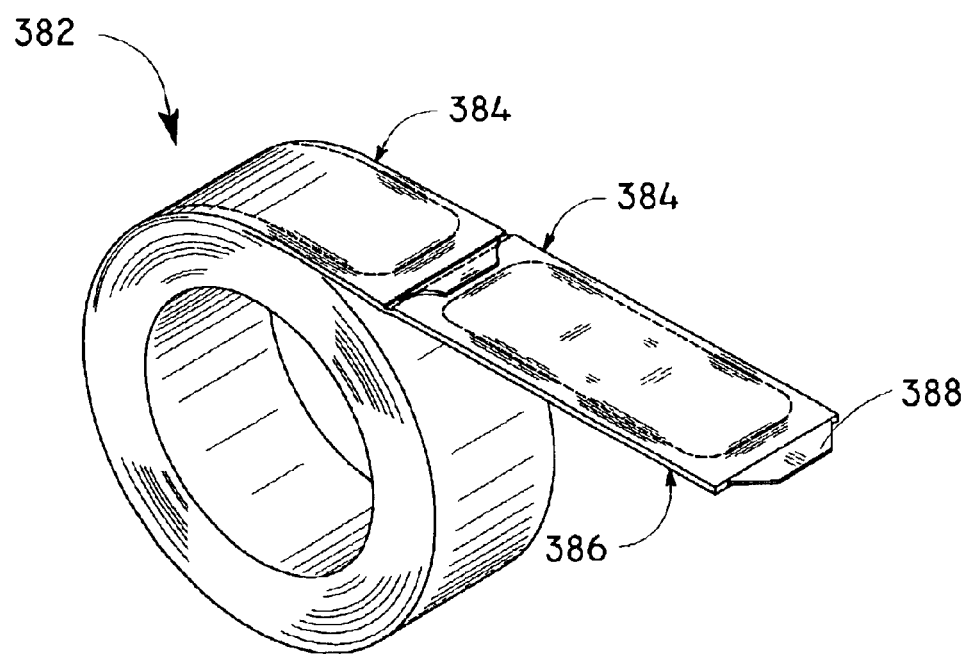
FIG. 26 is a perspective view illustration of a second embodiment of a dispensing pack.

A perspective view illustration of a second embodiment of a dispensing pack is shown in FIG. 26. The dispensing pack 382 comprises a continuous roll sheet of material upon which a plurality of packages 384 are aligned and attached along their lateral axis. The first tab 388 extends such that the user can easily grasp it. The lower sheet 386 is formed integrally from the continuous roll sheet material. The continuous roll dispensing pack can be placed within a dispenser adapted to support and contain the continuous roll dispensing pack.

Figure 27:
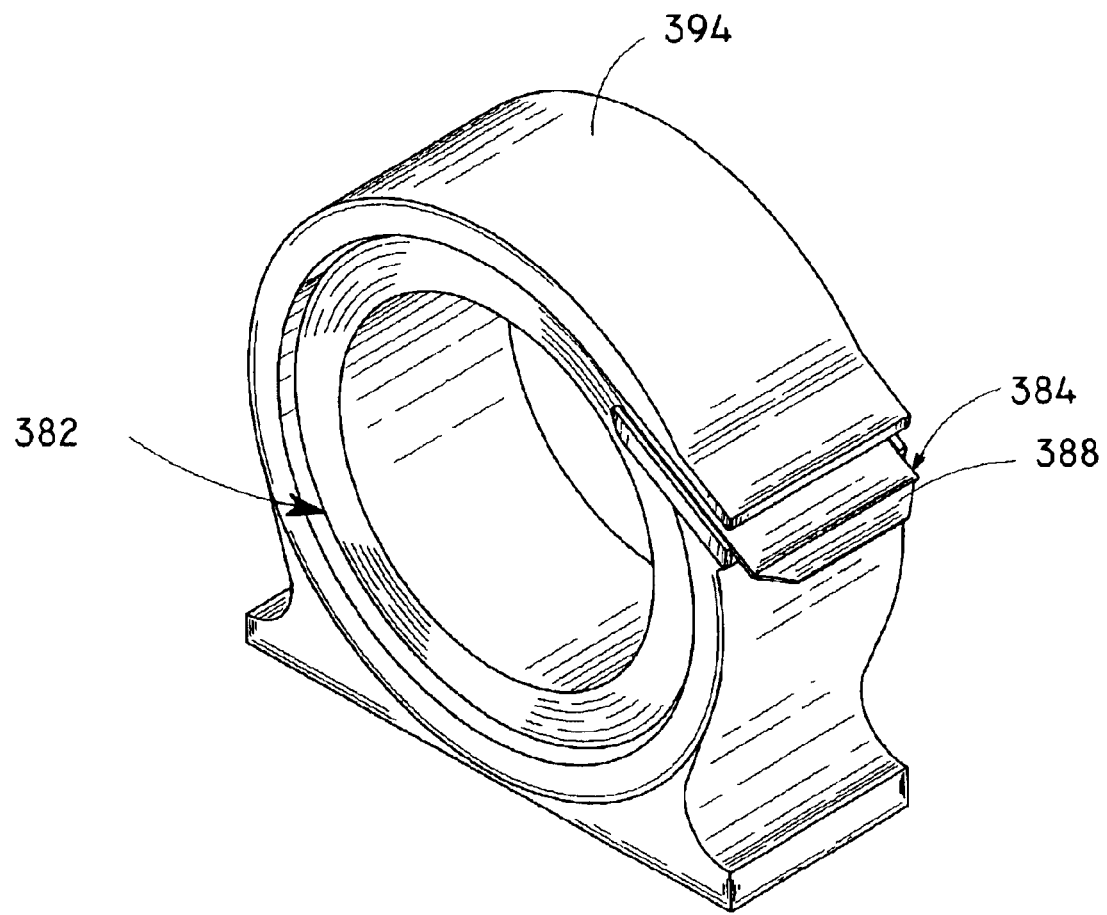
FIG. 27 is a perspective view illustration of a dispenser suitable for use with the continuous roll dispensing pack of FIGS. 26 and 28.
Figure 28:
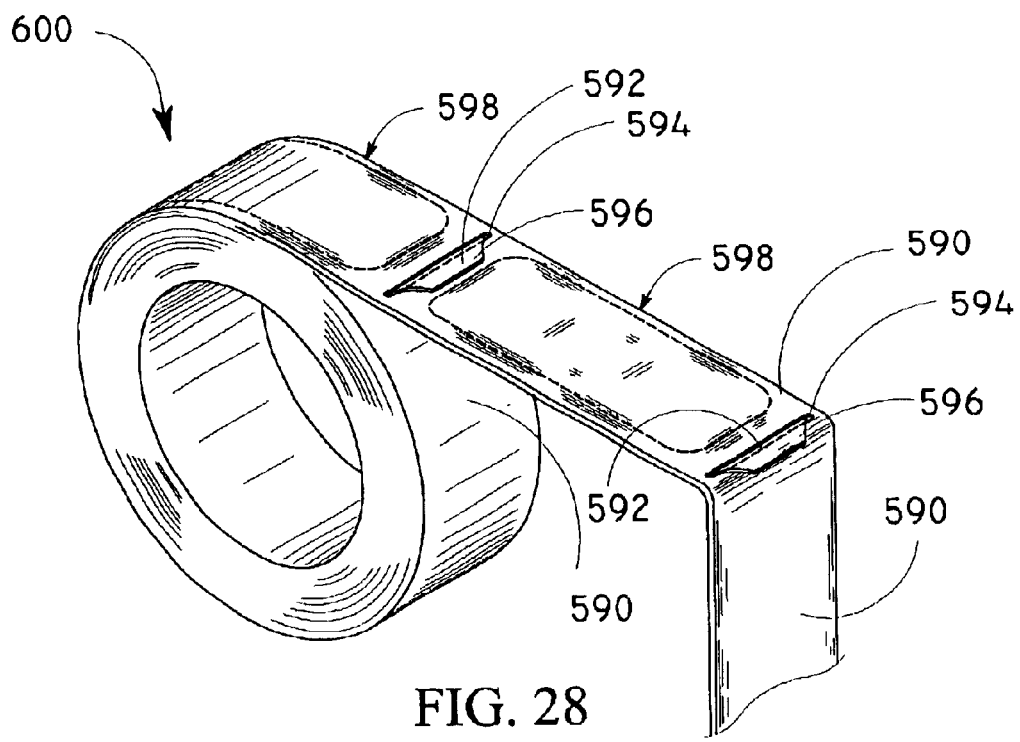
FIG. 28 is a perspective view illustration of the dispensing pack of FIG. 26 using a continuous upper and lower sheet.

A perspective view illustration of a dispenser suitable for use with the continuous roll dispensing pack (as illustrated in FIGS. 26 and 28) is shown in FIG. 27. The continuous roll dispensing pack 382 is placed within a dispenser 394 such that individual adhesive strips may be dispensed. The packages are torn off after use. The manufacture of dispensers are well known in the art.

A perspective view illustration of the dispensing pack of FIG. 26 using a continuous upper and lower sheet is seen in FIG. 28. This embodiment is similar to the embodiment illustrated in FIG. 26 with a difference being the use of a continuous upper sheet 590 rather than individual upper sheet. The dispensing pack 600 comprises a continuous upper sheet and a continuous lower sheet. A pull cover 592 is placed in a pull cover opening 594 so that the first tab 596 protrudes out of the pull cover opening to enable a user to easily grasp it. The pull cover, adhesive strip, release liner and optional carrier are narrower than the pull cover opening so that the pull cover, adhesive strip, release liner and optional carrier easily puss through the pull cover opening when the package 598 is opened and the adhesive strip therein is removed. Likewise, the pull cover opening should be of sufficient size so as to allow the pull cover, the adhesive strip, the release liner and the optional carrier to easily pass through it when the package is opened and the adhesive strip contained within the package is removed. An optional blocking member is used to control the thickness of the package. The upper sheet is formed from a thin, flexible, polymer which is resistant to tearing, but may also be formed from other materials as described elsewhere in this invention. An optional dispensing pack, such as that which is shown in FIG. 27 above, is used to dispense the individual bandages. Alternatively, the dispensing pack would have an optional take-up means, such as a spool or a reel, which would take-up the empty packages. Dispensers which use take-up reels are known in the art and are used in numerous types of dispensers such as correction-tape dispensers (such as Correct-Tape™) as well as in adhesive-film dispensers (such as the Easy-Stick roller™ manufactured by Manco, Inc., Avon, Ohio). Such dispensers are described in U.S. Pat. No. 4,851,076, to Manusch et at., entitled "Adhesive film applicator." If a take-up spool is used, then it is preferred that the lower sheets make an acute angle bend somewhere between the dispensing pack and the take-up spool. The pull covers then extend beyond the upper and lower sheets at the bend making it more convenient to grasp them.

In alternative embodiments, that section of the first tab which does not have to pass through the pull cover opening may be wider than the pull cover opening. Furthermore, if desired, the pull cover and/or first tab is shaped and sized such that the exterior portions are larger than the pull cover opening such that the exterior portions can be sealed around the perimeter of the pull cover opening so as to maintain sterility within the inner envelope wherein the adhesive strip is located.

Figure 29:
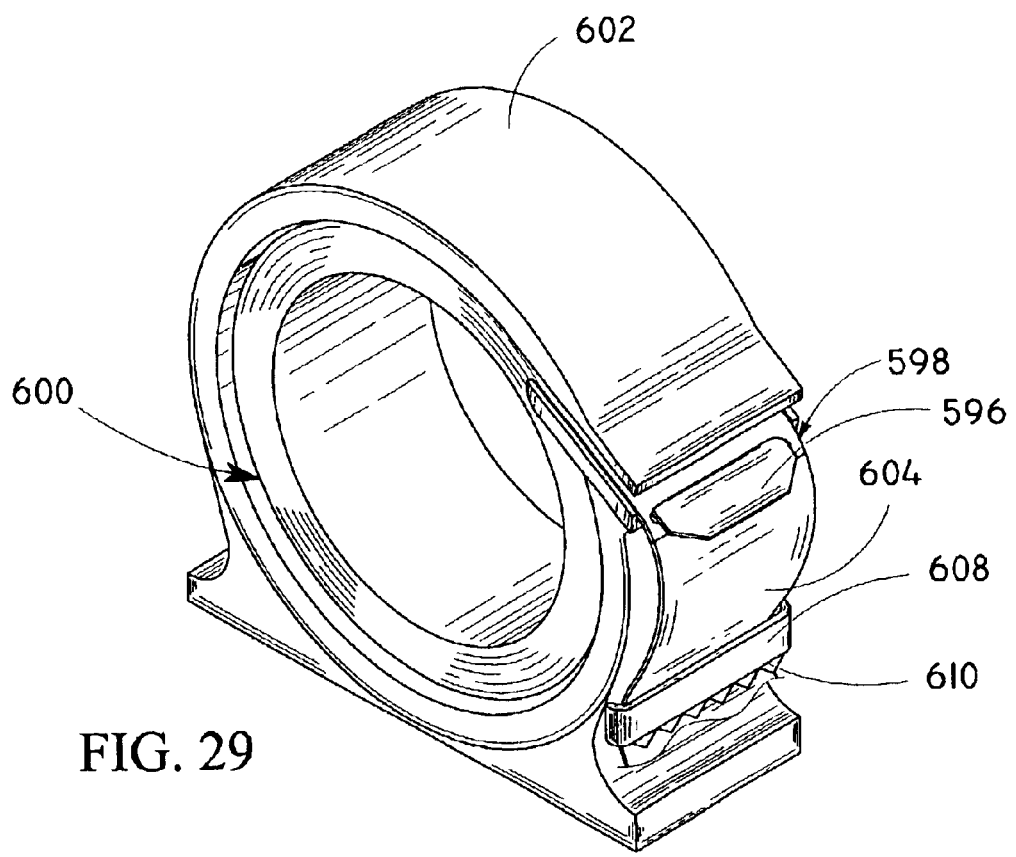
FIG. 29 is a perspective view illustration of an alternative dispenser that uses an external guide means suitable for use with the continuous roll dispensing packs of FIGS. 26 and 28.

A perspective view illustration of an alternative dispenser that uses an external guide means suitable for use with the continuous roll dispensing packs of FIGS. 26 and 28 is shown in FIG. 29. The continuous roll dispensing pack 600 is placed within a dispenser 602 such that individual adhesive strips can be dispensed by pulling on the individual first tabs 596. After an adhesive strip is dispensed, a new package is pulled into place and the empty packages 604 are directed through a guide means 608, and if desired, cut by pulling the empty packages against a cutting means 610. The cutting means may comprise a serrated metal strip. Alternatively, the continuous upper sheet and the continuous lower sheet are scored or perforated so that they can be easily torn. Dispensers are well known in the art. In alternative embodiments, the continuous roll dispensing pack can be placed within a supply spool/take-up spool dispenser (not shown).

Figure 30:
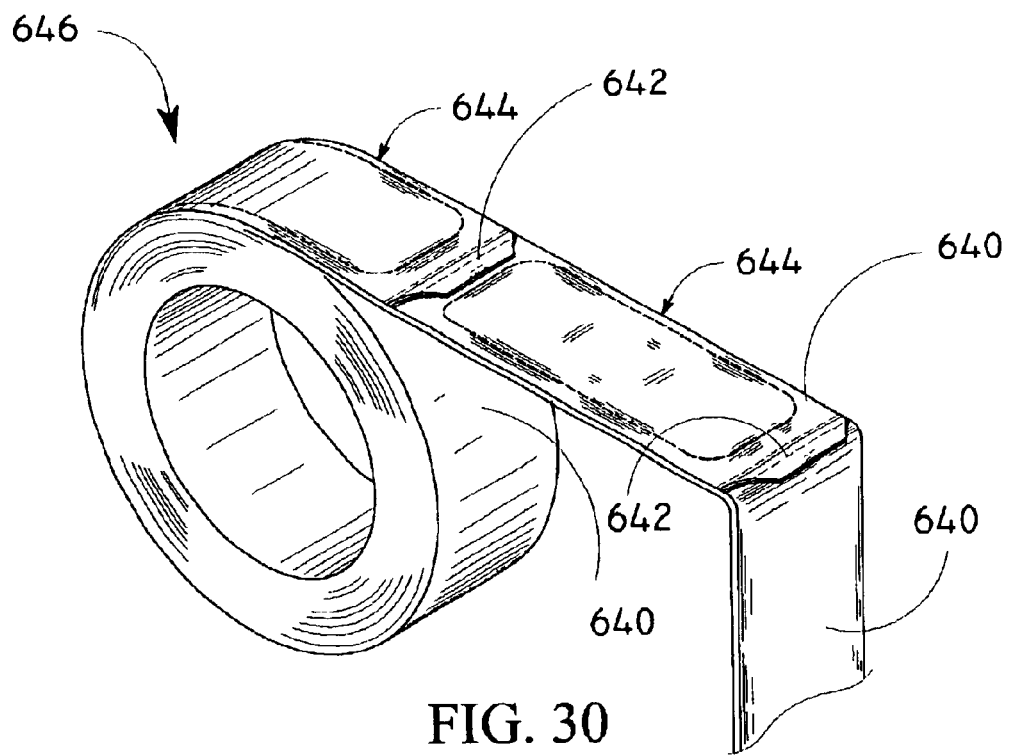
FIG. 30 is a perspective view illustration of the dispensing pack of FIG. 26 using a continuous upper sheet with an integral pull cover and a continuous lower sheet.

A perspective view illustration of the dispensing pack of FIG. 26 using a continuous upper sheet with an integral pull cover and a continuous lower sheet is shown in FIG. 30. This embodiment is similar to the embodiment illustrated in FIG. 26 with a difference being the use of a continuous upper sheet 640 having an integral pull cover 642 rather than individual upper sheets. The individual packages 644, which form the dispensing pack 646, are similar to those shown in FIG. 19 described hereinabove. An optional blocking member is used to control the package thickness. An optional dispensing pack, such as that which is shown in FIGS. 27 and 29 described supra, is used to dispense the individual bandages. Alternatively, the dispensing pack may have an optional take-up means, such as a spool or a reel, which takes up the empty packages.

Figure 31:
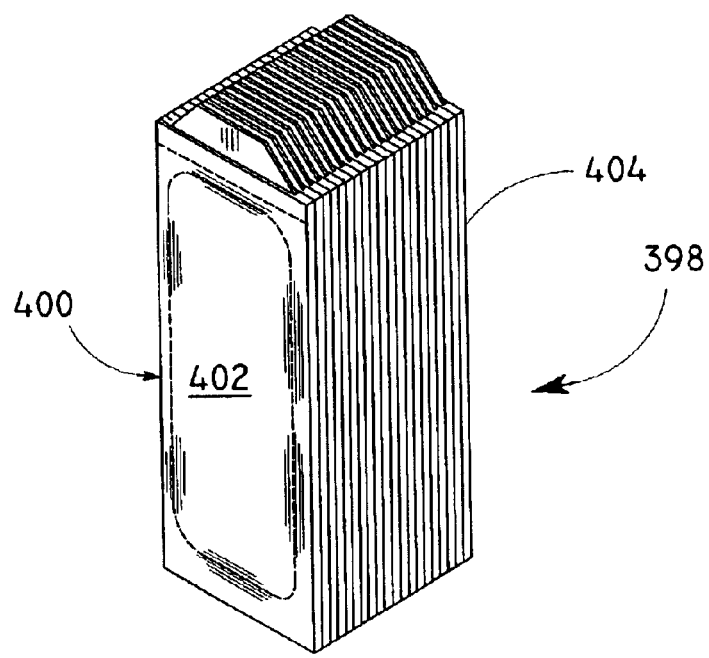
FIG. 31 is a perspective view illustration of a third embodiment of a dispensing pack.

A perspective view illustration of a third embodiment of a dispensing pack is shown in FIG. 31. The dispensing pack 398 is formed from a plurality of substantially superimposed packages 400, which are attached to or aligned with one another. The individual packages 400 are formed from one or more sheets of material either attached to each other, held adjacent to each other or folded in an accordion-like fashion so as to form a plurality of individual packages. In one embodiment, the dispensing pack is constructed from a single sheet of material folded in an accordion-like fashion, so as to form both the upper sheet 402 and the lower sheet 404 of the package. In another embodiment, the dispensing pack is formed from a single sheet of material that forms the lower sheet. The upper sheet is formed from individual sheets that are attached to the continuous sheet so as to form the package. In another embodiment, the dispensing pack is formed from two continuous sheets of material that are folded in an accordion-like fashion so as to form the packages. One sheet of material forms the upper sheet, while the other sheet forms the lower sheet. In another embodiment, the dispensing pack is formed from individual packages which are aligned with and stacked upon each other. In all embodiments of the dispensing pack 398 the individual sheets may be folded either along their longitudinal or lateral axis. In other alternative embodiments, in order to avoid substantial package deformation, the individual packages are held in close proximity by a holding means, which positions the packages in a desired location. Suitable holding means may comprise adhesive, staples or other means which position individual packages in a desired position (e.g., a piece of paper bonded to several individual packages to form a dispensing pack). In alternative embodiments, either or both the upper sheet and/or the lower sheet are extended. A plurality of packages are then superimposed upon each other and held in position by a staple which is inserted proximate to the second tab of the package.

Figure 32:
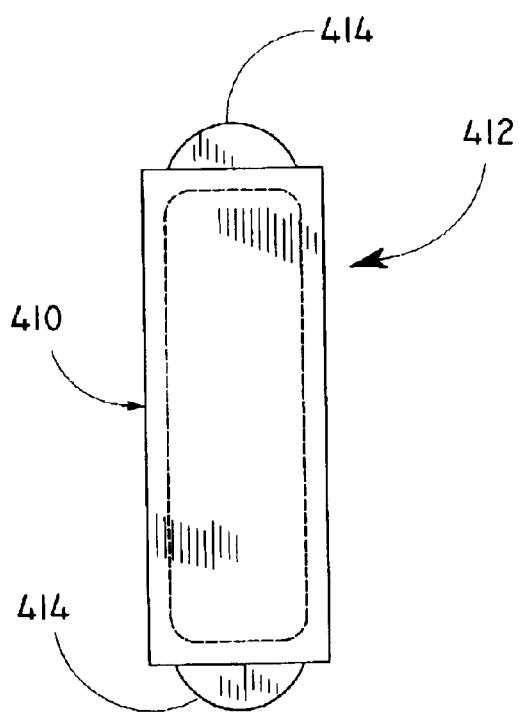
FIG. 32 is a front side view illustration of a fourth embodiment of a dispensing pack adapted to dispense adhesive strips from opposing sides.

A front side view illustration of a fourth embodiment of a dispensing pack adapted to dispense adhesive strips from opposing sides is shown in FIG. 32. The individual packages 410 that comprise the dispensing pack 412 are located with their pull covers 414 opposing each other such that the adhesive strips or bandages which are adjacent to each other are dispensed from opposite ends of the dispensing pack. Additionally, if different-sized adhesive strips or bandages are used, then to aid the user in discerning the size of the adhesive strip or bandage, the individual packages that make up the dispensing pack are located with the pull covers opposing each other such that different-sized adhesive strips or bandages are located on and dispensed from opposite ends of the dispensing pack.

Although the dispensing pack may, if desired, dispense individual adhesive strips without the aid of a suitable container means, it is preferable that the dispensing pack dispense adhesive strips while contained within a suitable container means, as illustrated and described hereinbelow.

Figure 33:
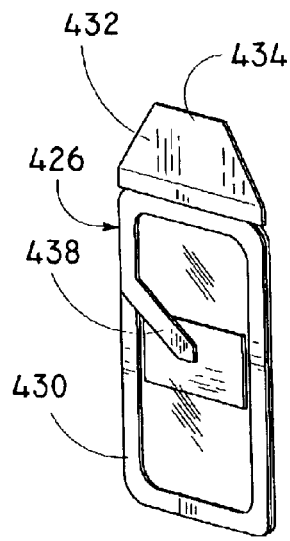
FIG. 33 is a perspective view illustration of the adhesive strip with a one-piece carrier and pull cover, as used in the dispensing pack of FIG. 34.
Figure 34:
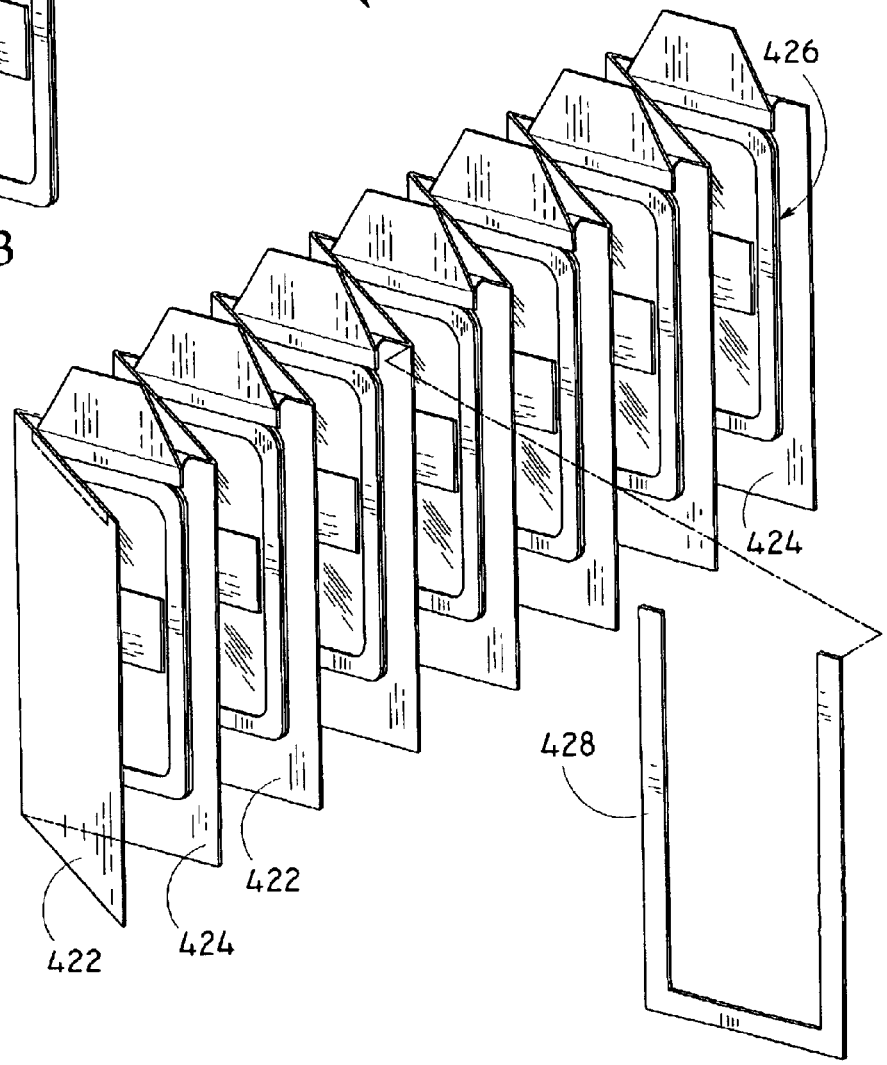
FIG. 34 is an exploded perspective view illustration of a dispensing pack incorporating an optional blocking member and one piece carrier and pull cover assembly.

A perspective view illustration of the adhesive strip with a one-piece carrier member and pull cover as used in the dispensing pack of FIG. 34 is shown in FIG. 33. The adhesive strip 426 has a carrier 430 bonded thereto. The carrier, pull cover 432, first tab 434 and pull tab 438 are formed integrally from the same sheet of material. A wound pad 436 is shown attached to the adhesive strip. In alternate embodiments, the pull cover is not necessarily formed from the same sheet of material as the optional carrier.

An exploded perspective view illustration of a dispensing pack with an optional blocking member and a one-piece carrier and pull-cover assembly is shown in FIG. 34. The dispensing pack 420 is constructed from a single sheet of material folded in an accordion-like fashion to form both the upper sheet 422 and the lower sheet 424 of the package. Without limitation, the pull cover 432 is releasably attached to the upper sheet and the lower sheet using a peel-stress-type bond which preferably uses appendages as is discussed elsewhere in this invention. Alternatively, the pull cover may be attached to the upper sheet using other suitable methods as are described elsewhere in this document.

The dispensing pack contains an adhesive strip (or bandage) 426 in every other fold. Alternatively, to increase packaging efficiency, the dispensing pack may comprise an adhesive strip (or bandage) in each fold. Additionally, the dispensing pack may also dispense adhesive strips (or bandages) of various sizes and shapes. The optional blocking member 428 (only one is shown for clarity) is used to control the shape and thickness of the dispensing pack. It can be used in any or all folds as desired. Blocking members are well known in the art. The second tab is optional and for the most part unnecessary. For example only, the adhesive strip is shown with a carrier 430. Adhesive strips, as described elsewhere in this invention, or other suitable adhesive strips, may also be used.

Figure 35:
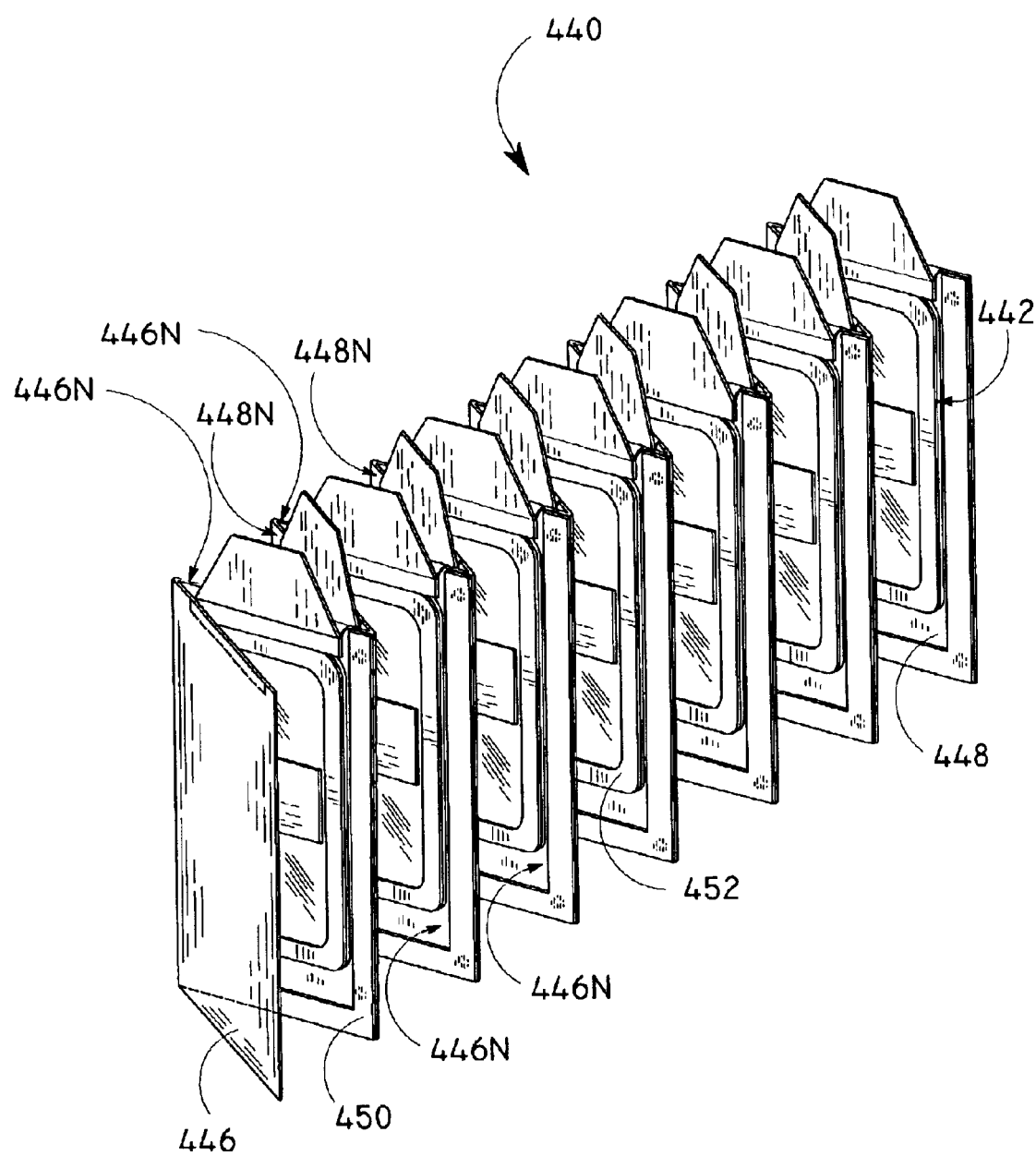
FIG. 35 is an exploded perspective view illustration of a dispensing pack with an optional blocking member and a one-piece carrier and pull-cover assembly with adhesive strips placed in each fold.

An exploded perspective view illustration of a dispensing pack with an optional blocking member and a one-piece carrier and pull-cover assembly with adhesive strips placed in each fold is shown in FIG. 35. This embodiment is similar to the embodiment illustrated in FIG. 34 with a difference being the insertion of an adhesive strip 442 (and attached release liner) in each fold rather than every other fold. The dispensing pack 440 is formed from a single sheet of material that is folded in an accordion-like fashion, so as to form both the upper sheet 446 and the lower sheet 448 of the package. Because of the efficiency of this embodiment, the adjacent interior packages share upper sheets 446N and lower sheets 448N, thus requiring approximately half the amount of material for manufacturing the upper sheets and lower sheets as compared with other embodiments which place adhesive strips in every other fold.

Without limitation, the pull cover is adapted to be releasably attached to the upper sheet using a peel-stress-type bond that preferably uses an appendage and is releasably attached to the lower sheet using a peel-stress-type bond that preferably uses an attachment tab. Alternatively, the pull cover can be attached to the upper sheet using other suitable methods as are described elsewhere in this document. The dispensing pack 440 comprises an adhesive strip (or bandage) 442 in every fold. Additionally, the dispensing pack 440 may also dispense adhesive strips (or bandages) of various sizes and shapes. The optional blocking member 450 is used to control the shape and thickness of the dispensing pack. It can be used in any or all folds as desired. Blocking members are well known in the art. For purposes of illustration, the adhesive strip is shown with a carrier 452. Adhesive strips, as described elsewhere in this invention, or other suitable adhesive strips, may also be used.

Figure 36:
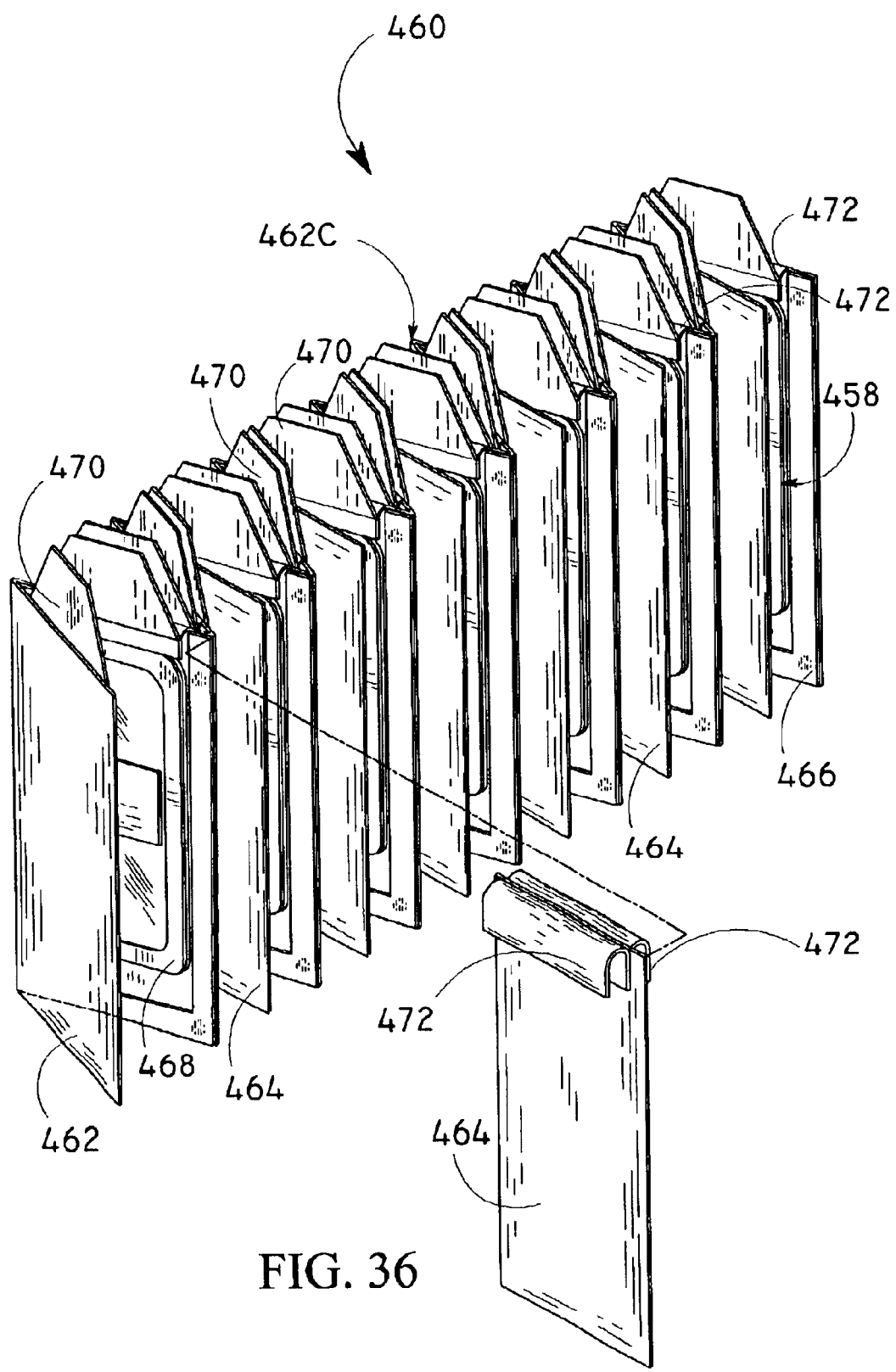
FIG. 36 is an exploded perspective view illustration of a dispensing pack with an optional blocking member and a one-piece carrier and pull-cover assembly with adhesive strips placed in each fold.

An exploded perspective view illustration of a dispensing pack with an optional blocking member and a one-piece carrier and pull-cover assembly with adhesive strips placed in each fold is shown in FIG. 36. This embodiment is similar to the embodiment illustrated in FIG. 35 with a difference being the insertion of two adhesive strips 458 (and the attached release liners) between each fold rather than one. The dispensing pack 460 comprises a single sheet of material (also known as the continuous lower sheet 462C) that is folded in an accordion-like fashion so as to form the lower sheets 462. The upper sheets 464 are formed from individual sheets that are placed between the folds of the continuous lower sheet 462C to form individual packages within the dispensing pack. The adjacent interior packages share upper sheets and lower sheets, thus greatly reducing the amount of material needed to produce the dispensing pack for any given number of adhesive strips. Without limitation, the pull cover 470 is releasably attached to the upper sheet and the lower sheet using a peel-stress-type bond which preferably uses attachment tabs 472 (not all of which are shown). Alternatively, the pull cover may be attached to the upper sheet using other suitable methods as are described elsewhere in this document. Additionally, the dispensing pack may also dispense adhesive strips (or bandages) of various sizes and shapes. The optional blocking member 466 is used to control the shape and thickness of the dispensing pack. It can be used in any or all folds as desired. Blocking members are well known in the art. For purposes of illustration, the adhesive strip is shown with a carrier 468. Adhesive strips, as described elsewhere in this invention, or other suitable adhesive strips, may also be used.

Figure 37:
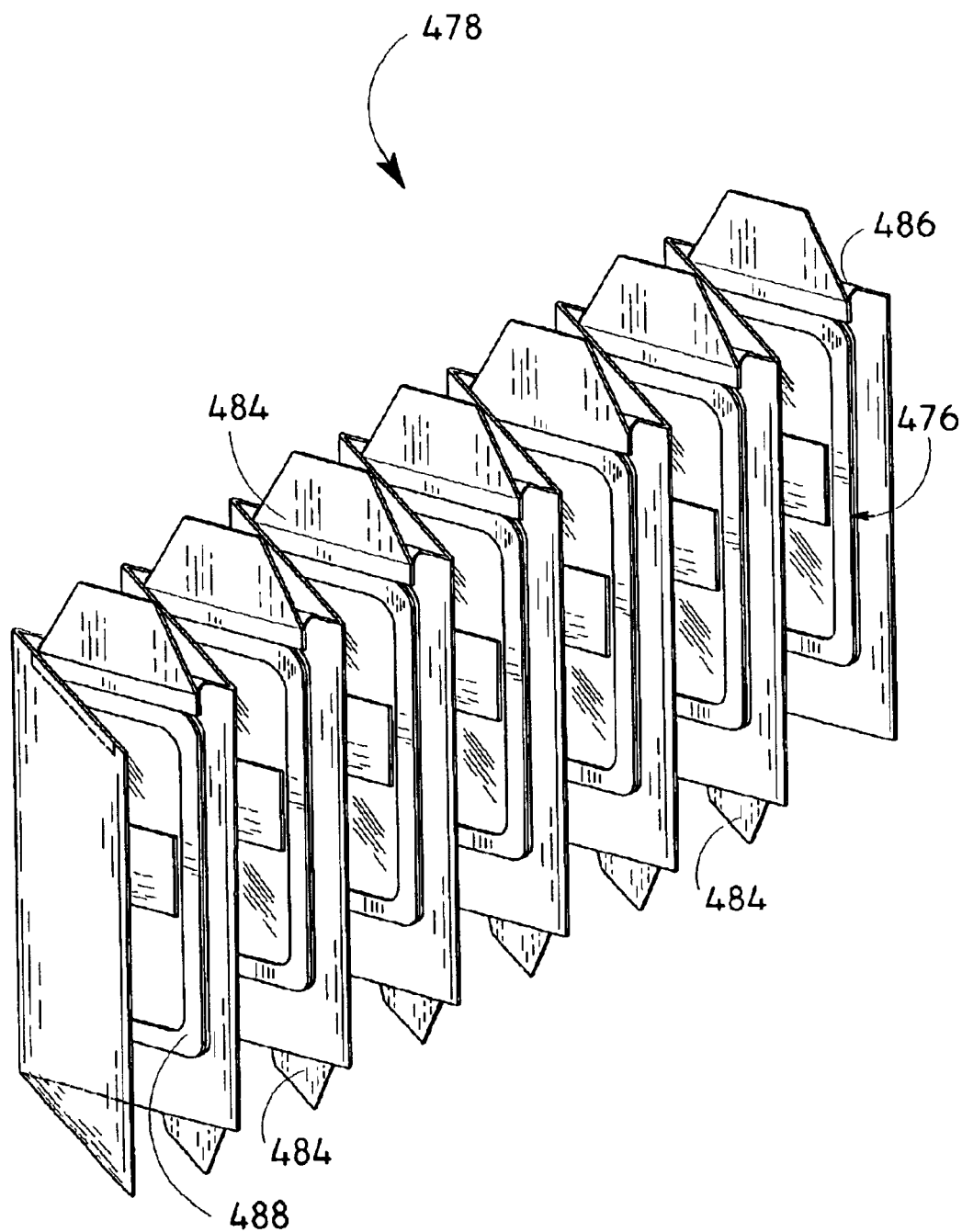
FIG. 37 is an exploded perspective view illustration of a dispensing pack which is adapted to dispense adhesive strips from opposing sides.

An exploded perspective view illustration of a dispensing pack which is adapted to dispense adhesive strips from opposing sides is shown in FIG. 37. This embodiment is similar to the embodiment illustrated in FIG. 34 with a difference being the insertion of an adhesive strip 476 (and attached release liner) in each fold rather than in every other fold. The individual adhesive strips (or bandages) 476 are located in folds such that the adhesive strips (or bandages) which are adjacent to each other are dispensed from opposite ends of the dispensing pack 478. The dispensing pack is constructed from a single sheet of material that is folded in an accordion-like fashion, so as to form both the upper sheet and the lower sheet of the package. Because of the efficiency of this embodiment, the adjacent interior packages share upper sheets and lower sheets, thus requiring approximately half the amount of material for manufacturing the upper sheets and lower sheets as compared with other embodiments which place adhesive strips in every other fold. Without limitation, the pull cover 484 is releasably attached to both the upper sheet and the lower sheet using a peel-stress-type bond that preferably uses an appendage. Alternatively, the pull cover may be attached to the upper sheet using other suitable methods us are described elsewhere in this document. Additionally, the dispensing pack may also dispense adhesive strips (or bandages) of various sizes and shapes. An optional blocking member (not shown) can be used to control the shape and thickness of the dispensing pack. It can be used in any or all folds as desired. Blocking members are well known in the art. For purposes of illustration only, the adhesive strip is shown with a carrier 488. Adhesive strips, as described elsewhere in this document, or other suitable adhesive strips, may also be used.

Figure 38:
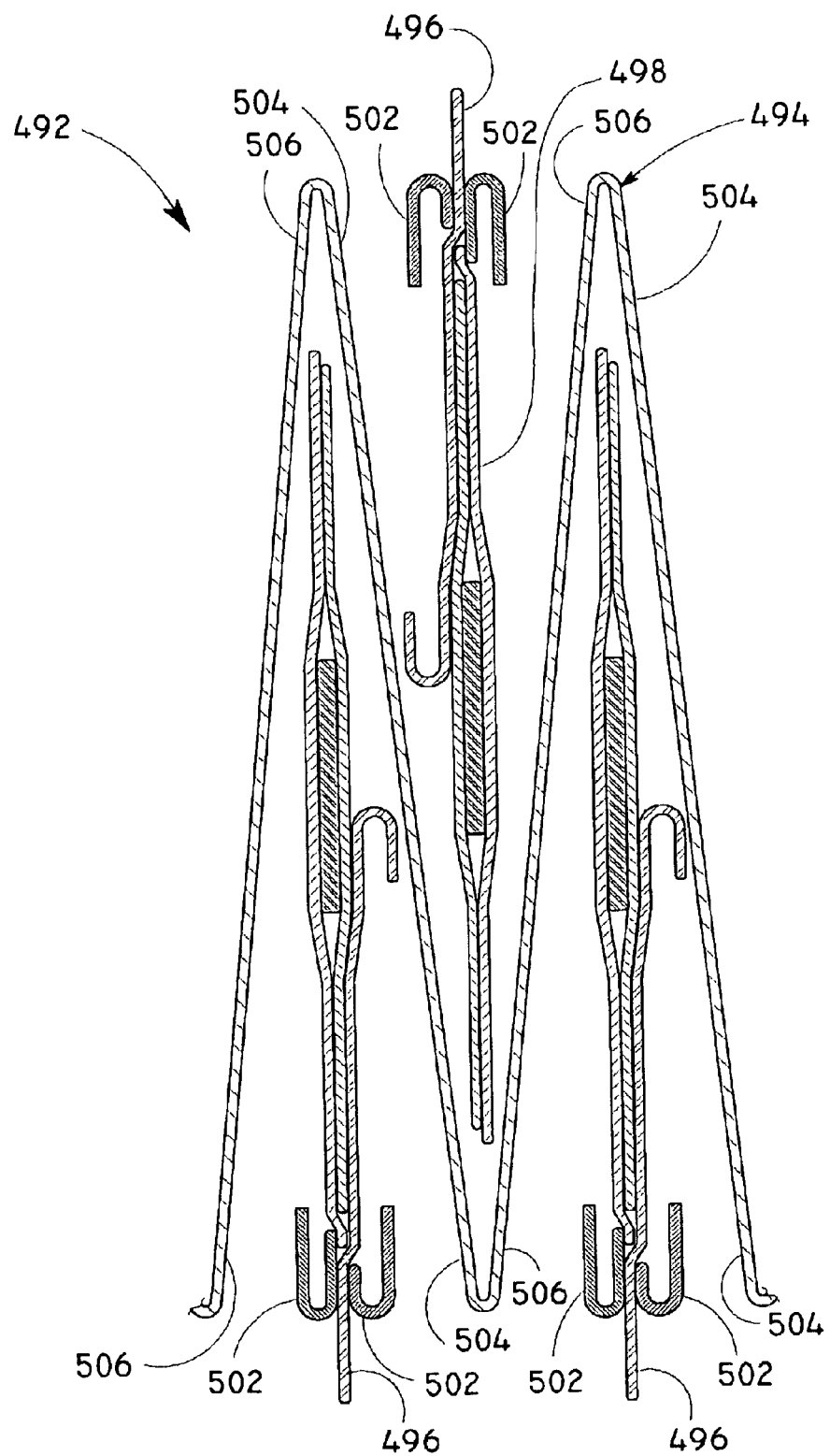
FIG. 38 is an exploded cross sectional view illustration of a dispensing pack with an optional blocking member and a one-piece carrier and pull-cover assembly.

An exploded perspective view illustration of a dispensing pack with an optional blocking member and a one-piece carrier and pull-cover assembly is shown in FIG. 38. The dispensing pack 492 is formed from a single sheet of material 494 that is folded in an accordion-like fashion (along its lateral axis), so as to form both the upper sheet 504 and the lower sheet 506 of the package. The pull cover 496 and adhesive strip 498 (with the release liner 500 attached) are placed in the folds and are held in place by an attachment means, such as the attachment tabs 502. The attachment tab is attached to the pull cover and the adjacent upper sheet and lower sheet as discussed elsewhere in this document. Alternatively, the pull cover may be attached to both the upper sheet and the lower sheet using other suitable methods as are described elsewhere in this document. The dispensing pack is sealed using a pressure-sensitive adhesive, thermal sealing or other suitable sealing methods, as discussed elsewhere in this document.

The dispensing pack contains an adhesive strip (or bandage) 498 in every fold. Alternatively, the dispensing pack may contain an adhesive strip (or bandage) in every other fold. Additionally, the dispensing pack may also dispense adhesive strips (or bandages) of various sizes and shapes. An optional blocking member (not shown) is used to control the shape and thickness of the dispensing pack. It may be used in any or all folds as desired. Blocking members are well known in the art. An optional adhesive pad is provided. In embodiments that place the adhesive strip in every other fold, the second tab is optional. In embodiments that use a dispensing packs, the second tab is not present. In alternate embodiments, the adhesive strip comprises a carrier member. Adhesive strips, as described elsewhere in this document, or other suitable adhesive strips, may also be used.

Figure 39:
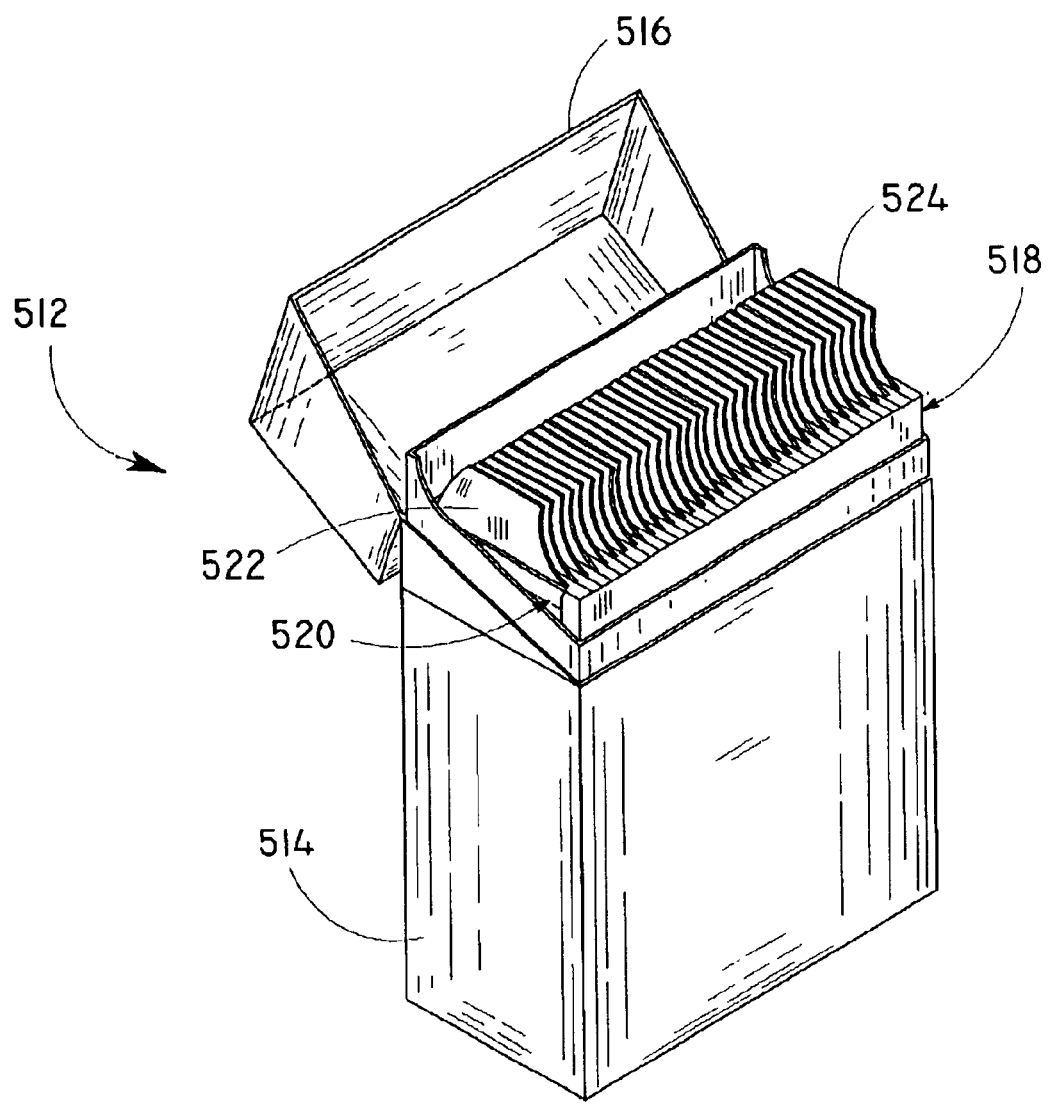
FIG. 39 is a perspective view illustration of a first embodiment of a container assembly mounted within a flip-top box.

A perspective view illustration of a first embodiment or a container means which uses a "flip-box" is shown in FIG. 39. The container 512 is a folding-top-type box (also known as a "flip-box") which comprises a body 514 and an attached lid 516. The container comprises one or more dispensing packs 518, wherein each dispensing pack comprises a plurality of packages 520 placed such that the pull covers 522 and adhesive strips are easily removed from the package. The lid is hingedly attached to the body of the container such that the pull covers (and/or first tabs 524) are easily grasped by the user when the lid 516 is opened. The dispensing pack is preferably attached to the body of the container using a heat glue or other suitable means (such as a locking-tab type mechanism). Such devices are commonly known as cigarette packages, and more particularly as "hard-packs," "crush-proof boxes," or "hinged-lid packages." See for example U.S. Pat. Nos. 4,852,734 and 3,874,581.

Figure 40:
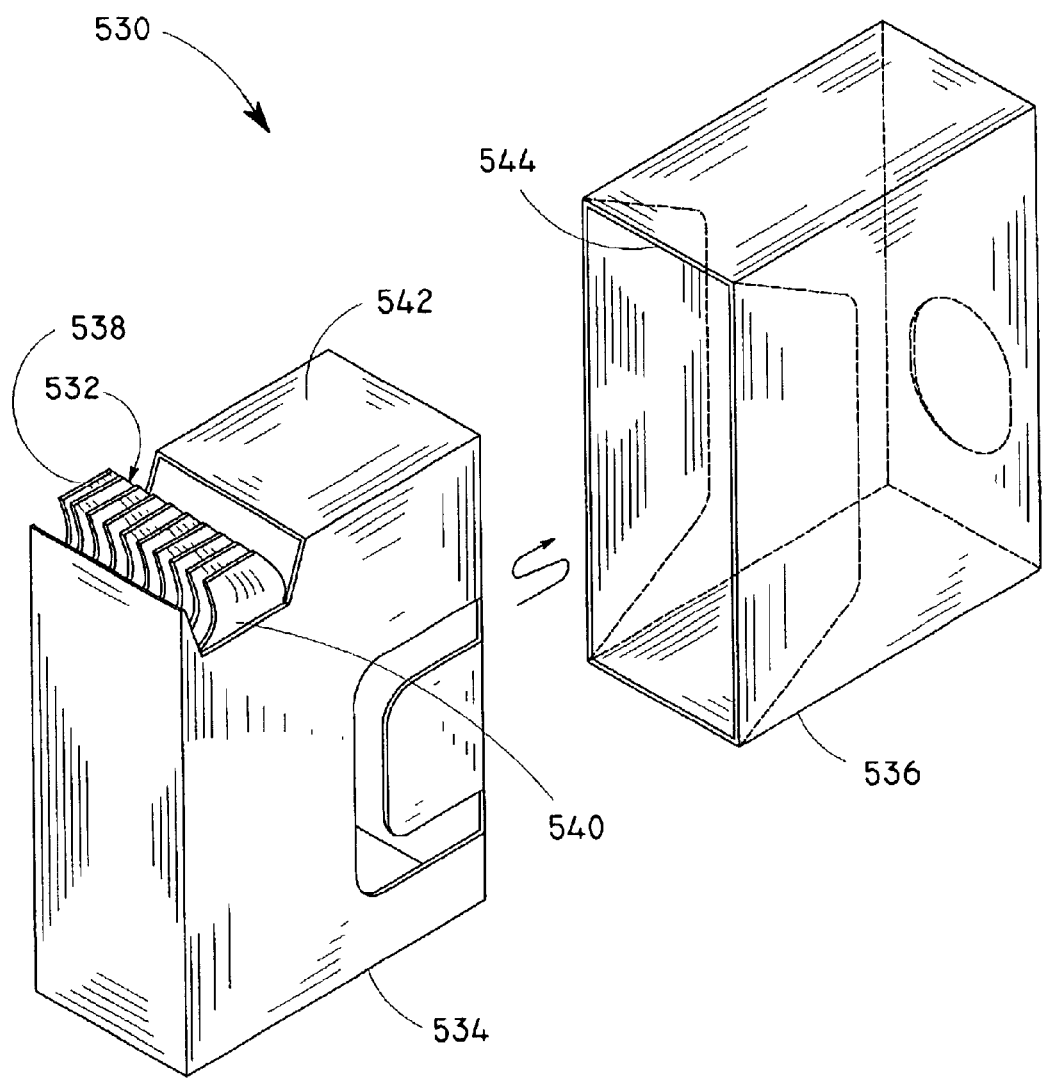
FIG. 40 is a perspective view illustration of a second embodiment of a container assembly incorporating a sliding-box.

A perspective view illustration of a second embodiment of a container assembly incorporating a sliding-box is shown in FIG. 40. The sliding-box-type container 530 (hereinafter sliding-box) comprises one or more dispensing packs 532. The sliding-box and its structure are well known in the art. See, for example, U.S. Pat. No. 5,080,227, to Focke, entitled "Pack made of thin cardboard, especially for cigarettes," incorporated herein by reference in its entirety. The sliding-box container comprises an inner section 534 (also known as a "box part") and an outer section 536 (also known as a "casing") both of which are slideably located relative to each other. The inner section holds the dispensing pack such that the individual first tabs 538 are easy to grasp. The dispensing pack is preferably attached to the inner section using a suitable means such as an adhesive (e.g. heat glue), or a locking-tab means. The inner section slides into a void located in the outer section. The inner section includes an opening that allows the user to grasp the first tab or the pull cover 540. In the preferred embodiment the first tabs and the pull covers are made from a flexible material, and either or both of them extend slightly beyond the top 542 of the inner section so that the first tabs are easy to grasp by the user. The first tabs and/or the pull covers preferably include an angle cut into the side that contacts the upper opposed end 544 of the outer section so that the first tabs and/or the pull covers fold slightly and allow the outer section to enclose the inner section when the slide-box type container is closed. In use, the inner section extends outward from the outer section enough so as to fully expose the individual first tabs and/or the pull covers of dispensing pack.

Figure 41:
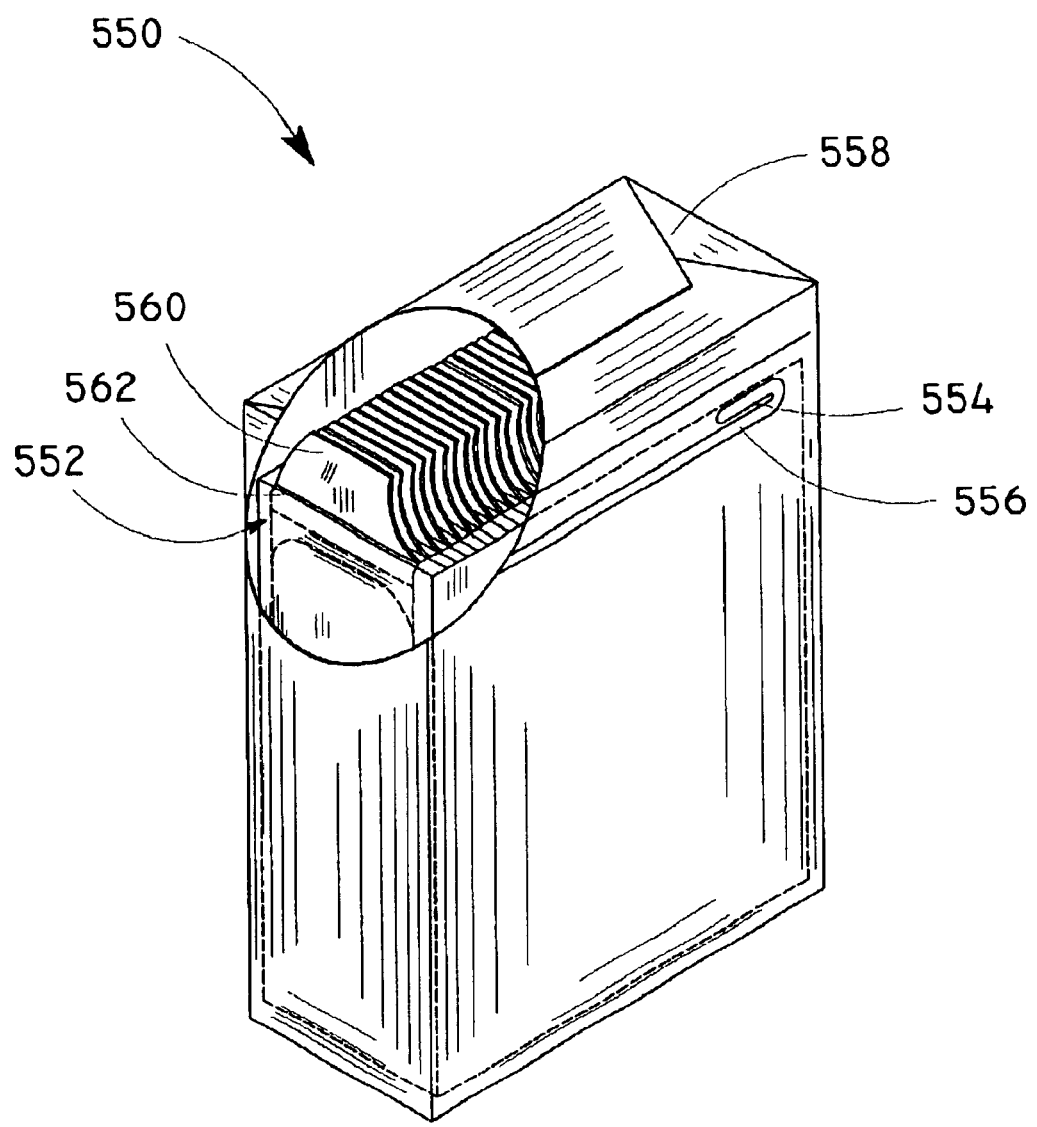
FIG. 41 is a semi-cutaway perspective view illustration of a third embodiment of a container assembly.

A semi-cutaway perspective view illustration of a third embodiment of a container assembly is shown in FIG. 41. The container 550 is a flexible cover that encloses the dispensing pack 552. Such packages are well known in the art and are often referred to as "soft-packs." The container comprises a tear tab 554 which works with a tear cord 556 located adjacent to the tear tab as shown. To open the package, the tear tab is pulled back over itself so that the container cover 558 is either opened or removed from the container which exposes the first tabs 560 and allows for the user to remove the pull cover 562 and adhesive strip from the dispensing pack.

A perspective view illustration or a fourth embodiment of a container assembly incorporating a flip-cover-type box with the cover being in the closed position is shown in FIG.

42A. The flip cover type (or matchbook-like) container 820 is wrapped around and encloses one or more dispensing packs 828. The container is constructed from a single sheet of material (e.g., thin cardboard) folded to form a back cover 824 and a re-sealable front cover 822. The dispensing pack is secured to the back cover using a fastener such as a staple 826 or other suitable means such as adhesive.

Figure 42A:
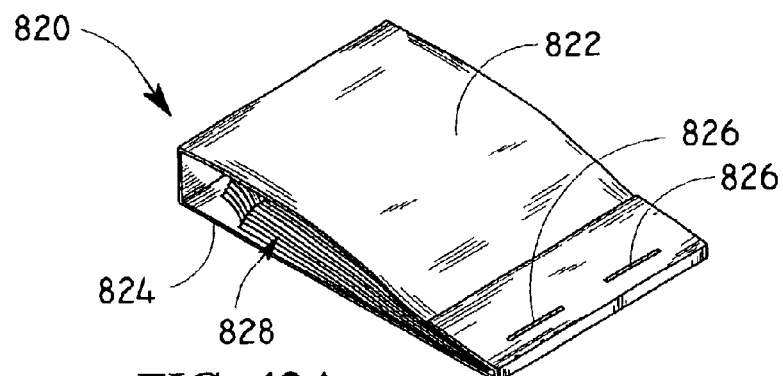
FIG. 42A is a perspective view illustration of a fourth embodiment of a container assembly incorporating a flip-cover-type box with the cover being in the closed position.
Figure 42B:
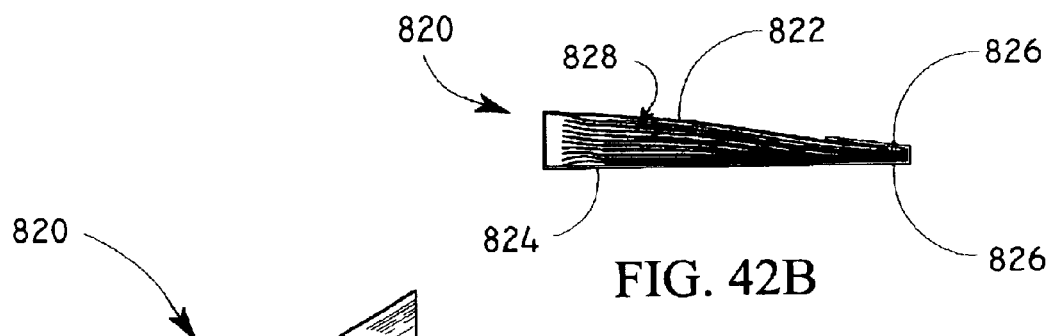
FIG. 42B is a side view illustration of the container assembly of FIG. 42A.

A side view illustration of the container assembly of FIG. 42A, is shown in FIG. 42B. The front cover 822 is retained in the closed position by a portion of the back cover 824 which wraps around and is attached to the dispensing pack.

Figure 42C:
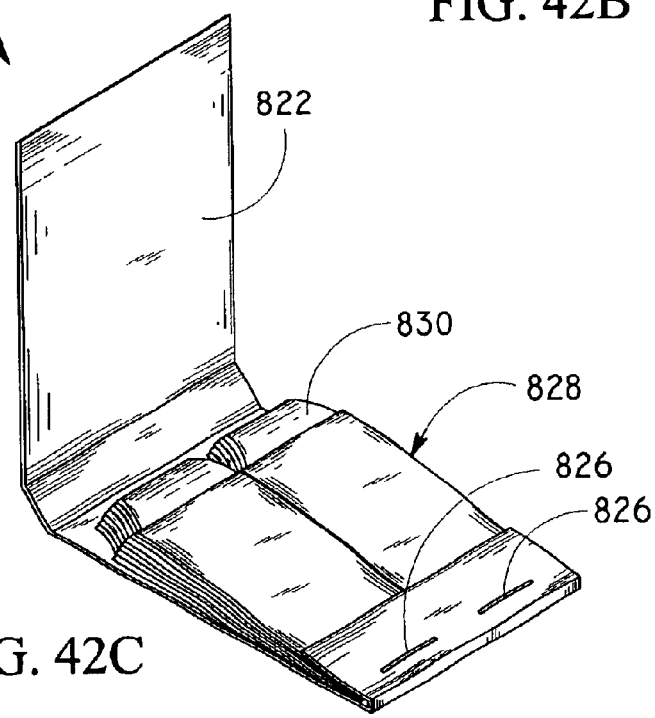
FIG. 42C is a perspective view illustration of the container assembly of FIG. 42A with the cover being in a semi-open position.

A perspective view illustration of the container assembly or FIG. 42A with the cover being in a semi-open position is shown in FIG. 42C. The front cover 822 is rotatably located relative to the back cover 824 such that the front cover is able to swing in excess of 180 degrees (and preferably swings about 270 degrees or more) form the front cover's closed position, so that the front cover does not come into contact with the adhesive strips as they are being removed from the dispensing pack. Additionally, the front cover is preferably adapted to allow easy access to the pull covers 830.

Figures 43A, 43B:
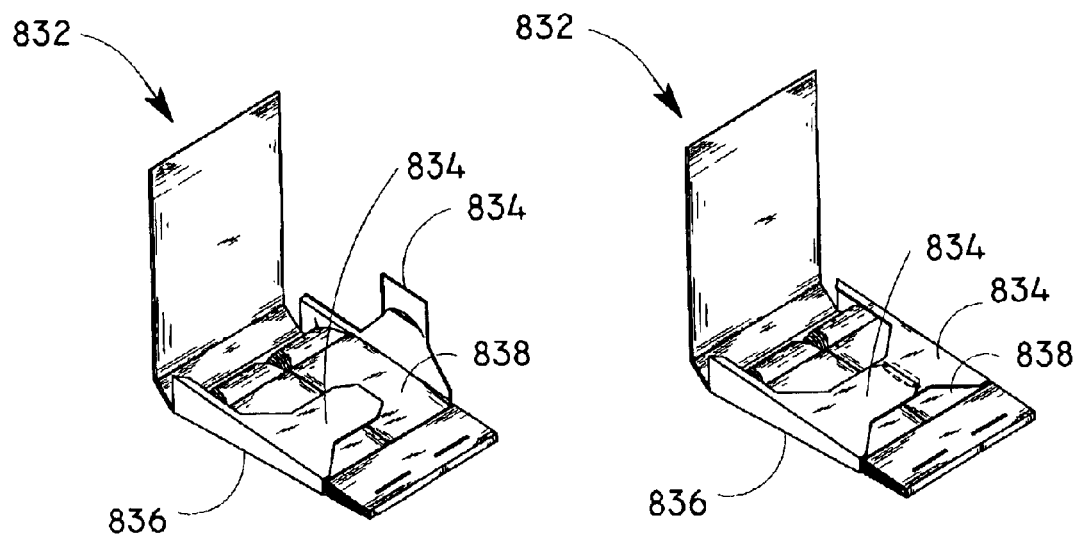
FIG. 43A is a perspective view illustration of a fifth embodiment of a container assembly incorporating a flip-cover-type box including side members, with the cover and one side member being in the semi-open position.
FIG. 43B is a perspective view illustration of the container assembly of FIG. 43A with side members secured to each other.

A perspective view illustration of a fifth embodiment of a container assembly incorporating a flip-cover-type box including side members, with the cover and one side member being in the semi-open position is shown in FIG. 43A. The flip cover type container 832 is substantially similar to the flip cover type container illustrated in FIGS. 42 through 42C described supra, with a difference being the addition of side members 834 which are articulated to the rear cover 836.

A perspective view illustration of the container assembly of FIG. 43A with side members secured to each other is shown in FIG. 43B. The side members 834 are folded around the dispensing packs 838 and are secured to each other using a suitable attachment means (e.g., a tab, adhesive, adhesive tape, staple, pressure bond, etc.) so that they conceal the dispensing pack contained within the container assembly 832. In alternative embodiments, side members are attached to the rear cover 836 using a weakened line (e.g., scoring or perforating) so that the side member can be removed after the container assembly is initially opened.

Figure 43C:
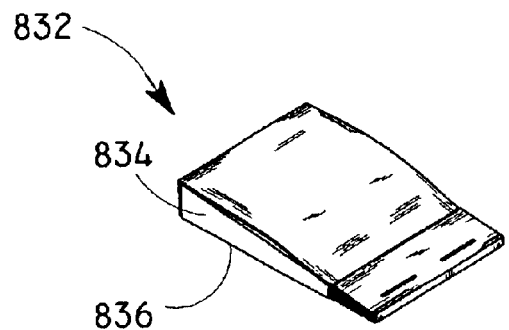
FIG. 43C is a perspective view illustration of the container assembly of FIG. 43A with the cover in the closed position.

A perspective view illustration of the container assembly of FIG. 43A with the cover in the closed position is shown in FIG. 43C. The side members 834 conceal and secure the dispensing packs 838 held within the container assembly 832 thus making the container assembly suitable for store-displays and merchandising fixtures without requiring additional packaging materials. The dispenser assembly 832 may optionally be oriented in the vertical position for hanging on display rails, storage rails or posts.

Figure 44A:
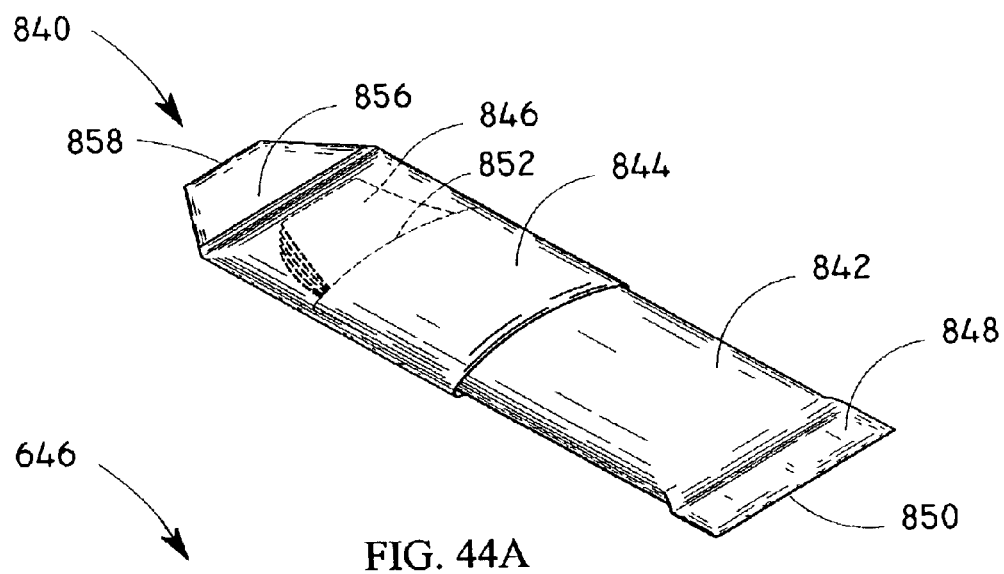
FIG. 44A is a perspective view illustration of a sixth embodiment of a container assembly incorporating a flexible outer wrapper having a body portion and a removable top portion.

A perspective view illustration of a sixth embodiment of a container assembly incorporating a flexible outer wrapper having a body portion and a removable top portion is shown in FIG. 44A. The container assembly 840 comprises a flexible body portion 842 and a removable top portion 844. The flexible body portion is formed from a flexible sheet of material (e.g., treated paper) wrapped around and securely attached to a plurality of packages to form a dispensing pack. The flexible body portion comprises an open end 852 and a closed end 850. The closed end of the body portion is flattened and attached to itself (using adhesive, etc.) to seal one end of the body portion and to form a first holding tab 848 which is suitable for grasping. The pull tabs 846 of the dispensing pack extend outward from the open end of the body portion so that they are easy to grasp. The dispensing pack is secured to the body portion using any suitable method (e.g., adhesive, staples, pressure, etc.).

The top portion comprises a flexible cylindrical member having an open end 854 and a closed end 856. The top portion is constructed from the same material as the body portion. The closed end of the top portion is flattened and attached to itself (using adhesive, etc.) so as to seal one end of the top portion and to form a second holding tab 858 which is suitable for grasping. The open end of the top portion has an inner circumference which is slightly larger than the exterior circumference of the body portion so that the cover portion can be slidably attached to the body portion. In alternative embodiments the top portion may have a slight conical form to better secure the top portion to the body portion.

In alternative embodiments, the closed end of the top portion comprises a weakened line (e.g., scoring, perforating or adhesive) so that the closed end can be opened. In use, the pull tabs are accessed by slidably repositioned the top portion along the longitudinal axis of the body portion so that the pull tabs of the dispensing pack extend outward from the now open closed end of the top portion.

Figure 44B:
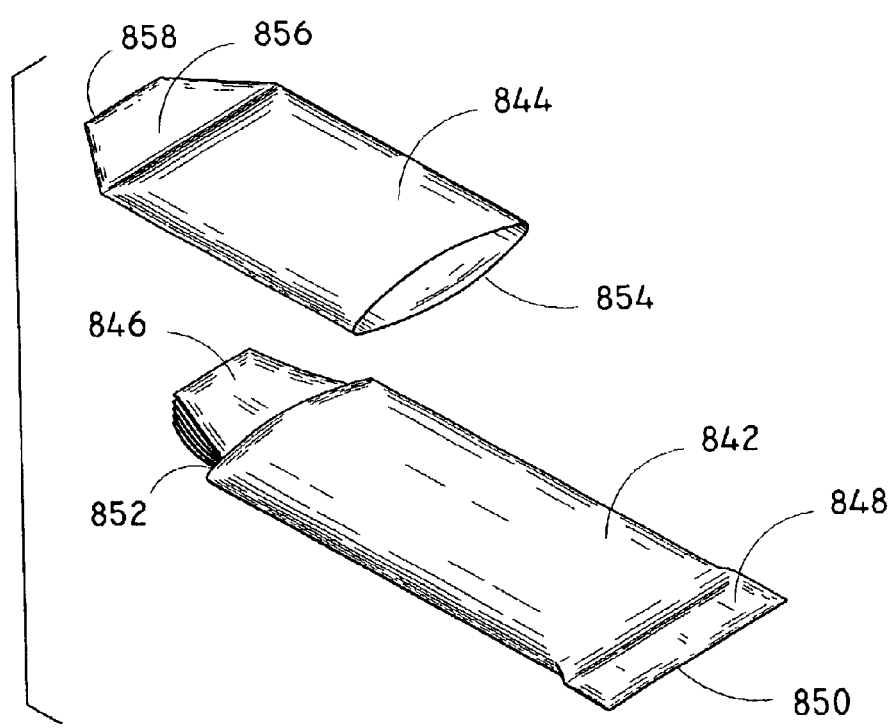
FIG. 44B is a perspective view illustration of the container assembly of FIG. 44A with the top portion removed.

A perspective view illustration of the container assembly of FIG. 44A with the top portion removed is shown in FIG. 44B. Removing the top portion exposes, and allows easy access to, the pull covers of the dispensing pack contained within the body portion.

Figure 45A:
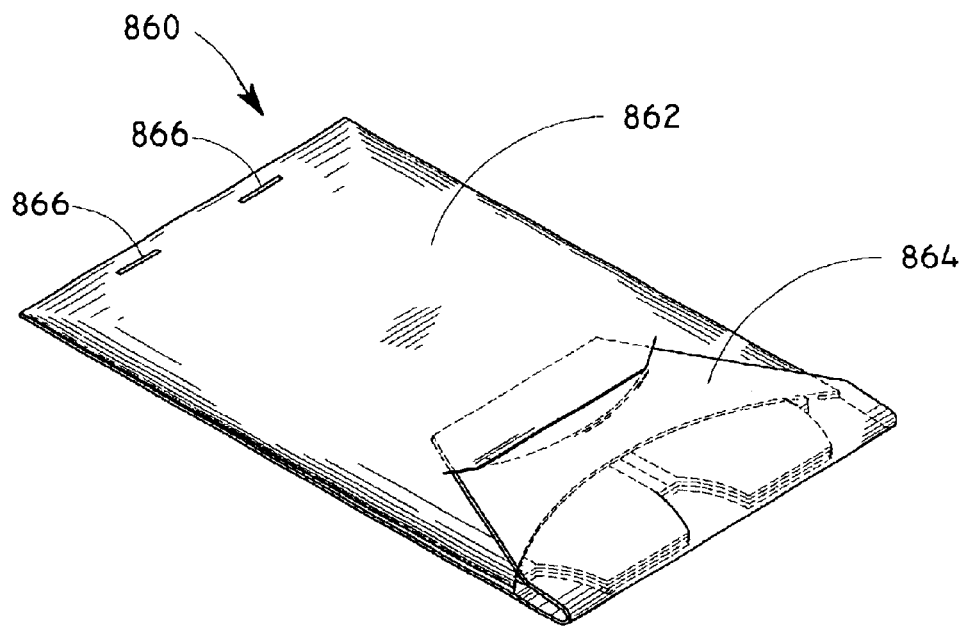
FIG. 45A is a perspective view illustration of a seventh embodiment of a container assembly incorporating a semi-rigid body portion and a re-sealable cover in the closed position.
Figure 45B:
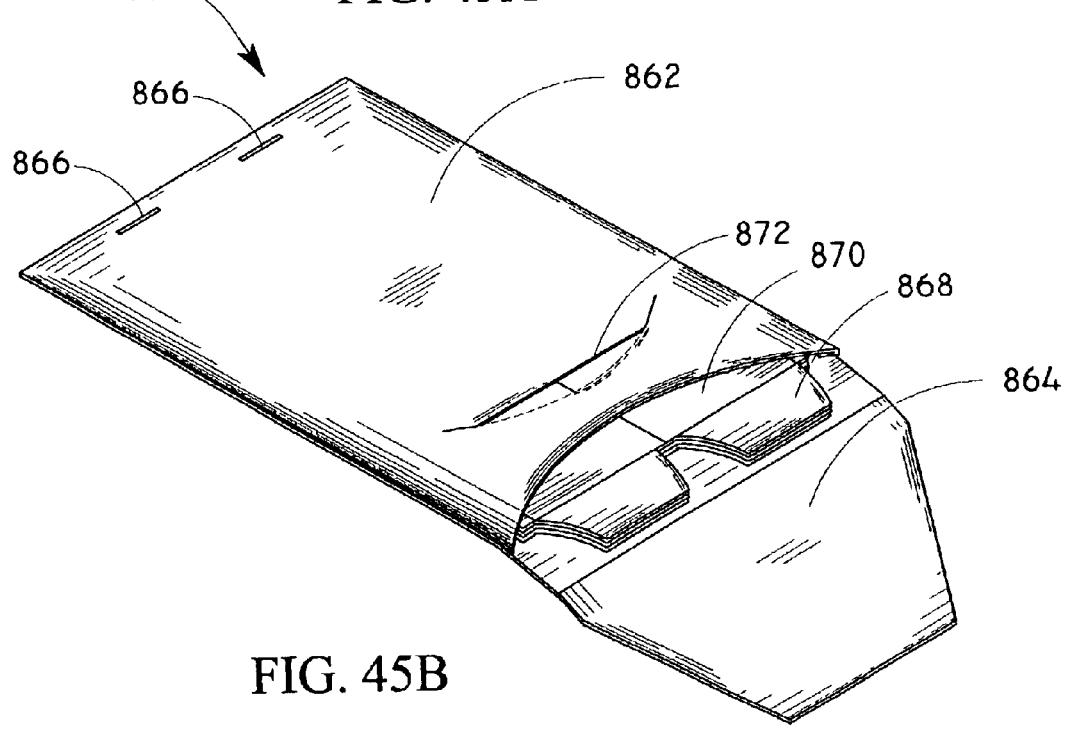
FIG. 45B is a perspective view illustration of the container assembly of FIG. 45A with the cover in the open position.

A perspective view illustration of a seventh embodiment of a container assembly incorporating a semi-rigid body portion and a re-sealable cover in the closed and open positions respectively, is shown in FIGS. 45A and 45B. The container 860 comprises a body 862 with a re-sealable cover 864. The container comprises one or more dispensing packs 870, wherein each dispensing pack contains a plurality of packages, situated such that the pull covers 868 and adhesive strips are easily removed from the package. The cover is articulated with the body of the container such that the pull covers (and/or first tabs) are easily grasped by the user when the cover is opened. The dispensing pack is attached to the body using an suitable method (e.g., staples 866, adhesive, pressure bonding, etc.). A slot 872 is provided to releasably secure the cover in the closed position. Alternatively, a re-sealable adhesive or other suitable method can be used. An optional U-shaped slit (not shown) is provided between the body and the cover to prevent the cover from folding back upon itself during removal of the adhesive strips from the dispensing pack.

Other alternative embodiments of the container means are envisioned for use with either the sheet or the roll form dispensing packs as shown and described above. For example, the roll form dispenser can be used in combination with a suitable dispenser such as shown in FIG. 3 of U.S. Pat. No. 5,891,078, to Turngren, entitled "Sterile adhesive bandage and associated methods," incorporated herein by reference in its entirety or with other suitable roll dispensers as are commonly known in the art.

It should be appreciated that the present invention, either alone, in a dispensing pack or with a dispensing pack and an optional container, is well suited for use by medical emergency personnel and others such as soldiers and pilots who have limited time to open a conventional package and remove a release liner, especially under urgent conditions or conditions which allow use of only a single hand. In other embodiments, the package may be constructed from waterproof materials so that it does not have to be enclosed in a container to maintain sterility.

The particular materials which may be employed in the practice of this invention are well known in the art. Preferably, the upper and lower sheets are constructed from paper of the same type as is now commonly used to wrap bandages or materials of similar nature. The release liner is preferably constructed from paper which is coated (or treated) on at least one side with a release material, the reverse side being suitable for adhering to the lower sheet. In many embodiments, the bandage itself is known and may be constructed from cloth, plastic, polyester, polyurethane, foam, film, fibrous webs, woven webs or any other suitable material or any combination thereof.

Furthermore, the flexible strip may be made from a combination of materials to obtain the desired properties. For example, the flexible strip, the absorbent pad or the adhesive coating on the surface of the flexible strip may be treated so as to possess antimicrobial properties. Such inventions are disclosed in the following: U.S. Pat. No. 4,728,323, to Matson, entitled "Antimicrobial wound dressings," U.S. Pat. No. 4,323,557, to Rosso, et al., entitled "pressure-sensitive adhesive containing iodine" and U.S. Pat. No. 4,310,509, to Berglund, et al., entitled "Pressure-sensitive adhesive having a broad spectrum antimicrobial therein" all of which are incorporated herein by reference in their entirety In addition, U.S. Pat. No. 5,976,117, to Dunshee, entitled "Wound dressing," incorporated herein by reference in its entirety, discloses a bandage which has at least two regions, one which is proximate to the wound and encourages cell regeneration and provides a space for wound exudate and a second region which substantially surrounds the first region comprising an antimicrobial agent in an amount that is at least sufficient to inhibit or essentially prevent migration of microorganisms to the first region from the external environment along the interface between the sheet material and the skin to which the sheet material has been adhered. Additionally, the absorbent pad (also known as a wound pad) or the flexible strip may be treated with a medicament or an antimicrobial film. Furthermore, the absorbent pad may be used for transdermal drug delivery or chemical indicators (used for monitoring). It will also be appreciated that the adhesive that is used in adhesive strips and bandages is preferably a dermatologically acceptable pressure-sensitive adhesive.

Other examples of adhesive strips include a means for securing catheter tubes, etc. or may be made from laminated materials that possess the desired properties.

Throughout this invention, it will be appreciated that the combination formed by the release liner and the releasably attached flexible strip, adhesive strip or bandage can be folded (transversely across its width) to minimize the space required by the package as well as the amount of packaging materials used to manufacture the package. If an adhesive strip and attached release liner are folded over then it is preferred that the combination not be too rigid in order that the bandage can be removed from the package without an undue amount of force. If using a rigidity enhancing carrier or other laminates upon the adhesive strip then care should be taken so that the laminates do not delaminate from each other. If using an adhesive strip then the adhesive strip is preferably folded at or near its midpoint. Whereas, if using a bandage then the bandage is preferably folded at a location that is somewhere between the wound pad and the end that is furthest from the leading edge of the bandage (before folding).

The user is further directed to the aforementioned U.S. Pat. Nos. 5,160,315 and 4,472,480 (incorporated herein by reference in their entirety) which describe the selection of release liners and carrier sheets as well as the methods of bonding them to an adhesive strip. Furthermore, the user is directed to the Handbook of Pressure-Sensitive Adhesive Technology by Satas and Associates Publisher as well as the 3M Product Selection Guide, Label Stocks, Laminating Adhesives and Printable Tapes, Mar. 1, 1996. The user is further directed to the Pressure Sensitive Tape Council, Northbrook, Ill., http://www.pstc.org, and to AIMCAL, Fort Mill, S.C., http://www.aimcal.org.

Certain additional advantages and features of this invention may be apparent to those skilled in the art upon studying the disclosure, or may be experienced by persons employing the novel structure of the present package and dispenser, chief of which is that it minimizes the risk of touching and contaminating the absorbent pad. Other advantages are quicker dispensing, easier application and reduction of the number of individual components requiring disposal.

While the invention has been described with a limited number of embodiments, it will be appreciated that changes may be made without departing from the scope of the original claimed invention, and it is intended that all matter contained in the foregoing specification and drawings be taken as illustrative and not in an exclusive sense.

What is claimed is:

1. A bandage package apparatus, comprising:
   a lower sheet having an upper surface and a lower surface;
   a release liner attached to said lower sheet;
   an adhesive strip having an upper surface and a lower surface, said lower surface of said adhesive strip being releasably attached to said release liner;
   an upper sheet having an upper surface and a lower surface, said upper sheet being attached to said lower sheet;
   a pull cover releasably attached to said adhesive strip, said upper sheet and said lower sheet, wherein said upper sheet and said lower sheet are releasably attached to each other along their outer perimeter except for a portion where they are attached to said pull cover; and
   a first tab located at an exterior end of said pull cover and extending beyond the outer periphery of at least one of said upper sheet and said lower sheet, said first tab adapted to be grasped by a user, wherein the act of pulling said first tab causes the separation of said release liner from said adhesive strip and also causes the removal of said adhesive strip from said package.

2. The apparatus according to claim 1, further comprising a second tab suitable for grasping and attached to the combination formed by said upper sheet and said lower sheet such that said second tab is located opposite said first tab.

3. The apparatus according to claim 1, wherein said pull cover is releasably attached to said upper sheet using a peel-stress type bond.

4. The apparatus according to claim 1, wherein said pull cover is releasably attached to said lower sheet using a peel-stress type bond.

5. The apparatus according to claim 1, further comprising an appendage on said lower sheet and an appendage on said upper sheet, said pull cover being releasably attached to said appendages.

6. The apparatus according to claim 1, further comprising an absorbent pad attached to said lower surface of said adhesive strip.

7. The apparatus according to claim 1, further comprising a pull tab attached to said pull cover and adapted to be suitable for grasping.

8. The apparatus according to claim 7, wherein said pull tab is attached to said pull cover such that a portion of said adhesive strip is positioned therebetween.

9. A bandage package apparatus, comprising:

a lower sheet having an upper surface, a lower surface and an appendage;

a release liner attached to said lower sheet;

a bandage having an upper surface and a lower surface, said lower surface of said bandage being releasably attached to said release liner;

an upper sheet having an upper surface, a lower surface and an appendage, said upper sheet being attached to said lower sheet;

a pull cover releaseably attached to said appendage of said upper sheet, said appendage of said lower sheet and said bandage, wherein said upper sheet and said lower sheet are releasably attached to each other along their outer perimeter except for a portion where they are attached to said pull cover, said pull cover adapted to form an envelope for enclosing and retaining said bandage within said package;

a first tab located at an exterior end of said pull cover and extending beyond the outer periphery of at least one of said lower sheet, said first tab adapted to be suitable for grasping;

a pull tab adapted to he grasped by a user, said pull tab being associated with said pull cover; and wherein the act of pulling said first tab causes the separation of said pull cover from said upper sheet and said lower sheet, the separation of said release liner from said bandage and the removal of said adhesive strip from said package.

10. The apparatus according to 9, further comprising a second tab suitable for grasping and attached to the combination formed by said upper sheet and said lower sheet such that said second tab is located opposite said first tab.

* * * * *